United States Patent
Langer et al.

(10) Patent No.: US 12,031,977 B2
(45) Date of Patent: Jul. 9, 2024

(54) EX VIVO SYSTEM FOR DETERMINING MULTIPLE DRUG-DRUG TRANSPORTER INTERACTIONS AND METHODS OF USE THEREOF

(71) Applicants: Massachusetts Institute of Technology, Cambridge, MA (US); The Brigham and Women's Hospital, Inc., Boston, MA (US)

(72) Inventors: Robert S. Langer, Newton, MA (US); Carlo Giovanni Traverso, Newton, MA (US); Yunhua Shi, Belmont, MA (US); Vance Soares, Boston, MA (US); Daniel Reker, Durham, NC (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 517 days.

(21) Appl. No.: 17/118,267

(22) Filed: Dec. 10, 2020

(65) Prior Publication Data
US 2021/0231645 A1    Jul. 29, 2021

Related U.S. Application Data

(60) Provisional application No. 62/946,336, filed on Dec. 10, 2019.

(51) Int. Cl.
G01N 33/50 (2006.01)
(52) U.S. Cl.
CPC ..... *G01N 33/5088* (2013.01); *G01N 33/5044* (2013.01)
(58) Field of Classification Search
CPC .................. G01N 33/5088; G01N 33/5044
See application file for complete search history.

(56) References Cited

U.S. PATENT DOCUMENTS

| | | | |
|---|---|---|---|
| 6,309,635 B1 | 10/2001 | Ingber et al. | |
| 7,390,653 B2 | 6/2008 | Akers et al. | |
| 8,298,822 B2 | 10/2012 | Kruse et al. | |
| 8,642,339 B2 | 2/2014 | Sato et al. | |
| 8,748,180 B2 | 6/2014 | Shuler et al. | |
| 9,127,254 B2 | 9/2015 | Cohen et al. | |
| 2010/0047853 A1 | 2/2010 | Kuo et al. | |
| 2014/0302491 A1 | 10/2014 | Nadauld et al. | |
| 2015/0329829 A1 | 11/2015 | Shen et al. | |
| 2018/0002672 A1 | 1/2018 | Allbritton et al. | |
| 2019/0064153 A1 | 2/2019 | Traverso et al. | |

FOREIGN PATENT DOCUMENTS

| | | |
|---|---|---|
| EP | 1896572 B1 | 2/2013 |
| JP | 2013009598 A | 1/2013 |
| WO | 2002/061424 A2 | 8/2002 |
| WO | 2014069995 A1 | 5/2014 |
| WO | 2014082096 A1 | 5/2014 |
| WO | 2016/123474 A1 | 8/2016 |
| WO | 2018/175861 A1 | 9/2018 |

OTHER PUBLICATIONS

Li, J-M et al. (2015), International Journal of Nanomedicine. 10:3147-3162.*
Amin, M.L., "P-glycoprotein Inhibition for Optimal Drug Delivery," Drug Target Insights, vol. 7: 27-34 (2013).
Aniceto, N., et al., Simultaneous Prediction of four ATP-binding Cassette Transporters' Substrates Using Multi-label QSAR. Mol Inform, vol. 35: 514-528 (2016).
Assimakopoulos et al. "Enterocytes' tight junctions: from molecules to diseases." World journal of gastrointestinal pathophysiology 2(6): 123-130 (2011).
Autrup, H. et al., Explant Culture of Rat Colon: A Model System for Studying Metabolism of Chemical Carcinogens, In Vitro, vol. 14(10): 868-877 (1978).
Balimane, P.V. et al., "Cell culture-based models for intestinal permeability: a critique," Drug Discov Today, vol. 10: 335-343 (2005).
Costa M.O. et al., "Development and evaluation of a porcine in vitro colon organ culture technique", In Vitro Cellular & Developmental Biology—Animal, vol. 52 (9):942-952 (2016).
Dedhia, P.H., "Reviews in Basic and Clinical Gastroenterology and Hepatology, Organoid Models of Human Gastrointestinal Development and Disease," Gastroenterology, vol. 150:1098-1112 (2016).
Deiss et al. "Platform for high-throughput testing of the effect of soluble compounds on 3D cell cultures." Analytical Chemistry, vol. 85 (17):8085-8094 (2013).
Deward, A.D. et al., "Cellular Heterogeneity in the Mouse Esophagus Implicates the Presence of a Nonquiescent Epithelial Stem Cell Population," Cell Reports, vol. 9: 701-711 (2014).
Dimarco, R. et al., "Engineering of Three-Dimensional Microenvironments to Promote Contractile Behavior in Primary Intestinal Organoids," Integr Biol., vol. 6(2): 127-142 (2014).
Dimarco, R. et al., "Protein-engineered scaffolds for in vitro 3D culture of primary adult intestinal organoids," Biomaterials Science, vol. 3:1376-1385 (2015).
Haimeur, A., et al., "The MRP-related and BCRP/ABCG2 multidrug resistance proteins: biology, substrate specificity and regulation," Curr Drug Metab., vol. 5: 21-53 (2004).
Haslam, Iain S. et al., "Pancreatoduodenectomy as a source of human small intestine for Ussing chamber investigations and comparative studies with rat tissue," Biopharm. Drug Dispos., vol. 32: 210-221 (2011).
Henze, L.J., et al., "The pig as a preclinical model for predicting oral bioavailability and in vivo performance of pharmaceutical oral dosage forms: a PEARRL review," J Pharm Pharmacol., vol. 71(4):581-602(2019).
Ingels, F.M. et al., Biological, pharmaceutical, and analytical considerations with respect to the transport media used in the absorption screening system, Caco-2, J Pharm Sci. vol. 92: 1545-1558 (2003).
International Preliminary Report on Patentability, PCT/US2018/023982, dated Sep. 24, 2019, 12 pages.

(Continued)

Primary Examiner — Robert S Landsman
(74) Attorney, Agent, or Firm — McCarter & English, LLP

(57) ABSTRACT

Methods and compositions for determining multiplex interactions between drugs and drug transporters using an intestinal tissue explant are provided.

10 Claims, 12 Drawing Sheets

Specification includes a Sequence Listing.

(56) References Cited

OTHER PUBLICATIONS

International Search Report and Written Opinion, PCT/US2018/023982, dated Jul. 31, 2018, 17 pages.

Invitation to Pay Additional Fees, and, Where Applicable Protest Fees, PCT/US2018/023982, dated Mar. 23, 2018, 15 pages.

Johnson, Z.L. & Chen, J., "Structural Basis of Substrate Recognition by the Multidrug Resistance Protein MRP1," Cell, vol. 168:1075-1085 e1079 (2017).

Kik, M.J. et al., "Pathological effects of Phaseolus vulgaris isolectins on pig jejunal mucosa in organ culture," Gut, vol. 32(8):886-892 (1991).

Kim, Y. et al., "Molecular structure of human P-glycoprotein in the ATP-bound, outward-facing conformation," Science, vol. 359: 915-919 (2018).

Kuratnik, A. et al., "Intestinal organoids as tissue surrogates for toxicological and pharmacological studies," Biochemical Pharmacology, vol. 85:1721-1726 (2013).

Macartney, K. et al., "Primary Murine Small Intestinal Epithelial Cells, Maintained in Long-Term Culture, Are Susceptible to Rotavirus Infection," Journal of Virology, vol. 74(12):5597-5603 (2000).

Medema, J.P. et al., "Microenvironmental regulation of stem cells in intestinal homeostasis and cancer," Nature, vol. 474: 318-326 (2011).

Montanari, F. et al., "Prediction of drug-ABC-transporter interaction—Recent advances and future challenges," Adv Drug Deliv Rev. vol. 86: 17-26 (2015).

Ootani, A. et al., "Sustained in vitro intestinal epithelial culture within a Wnt-dependent stem cell niche," Nat Med., vol. 15(6): 701-706 (2009).

Polentarutti, Britta I. et al., "Evaluation of Viability of Excised Rat Intestinal Segments in the Ussing Chamber: Investigation of Morphology, Electrical Parameters, and Permeability Characteristics," Pharmaceutical Research, vol. 16 (3): 446-454 (1999).

Pratt, J., et al., "Use of zinc finger nuclease technology to knock out efflux transporters in C2BBe1 cells," Curr Protoc Toxicol., Chapter 23, Unit 23: 22 pages (2012).

Randall et al. "Explant culture of gastrointestinal tissue: a review of methods and applications," Cell Biology and Toxicology, 267-284 (2011).

Ranga, A. et al., "Drug discovery through stem cell-based organoid models ," Advanced Drug Delivery Reviews, vol. 69-70: 19-28 (2014).

Rozehnal, V. et al., "Human small intestinal and colonic tissue mounted in the Ussing chamber as a tool for characterizing the intestinal absorption of drugs," European Journal of Pharmaceutical Sciences, vol. 46: 367-373 (2012).

Sampson, K.E., et al., "Zinc finger nuclease-mediated gene knockout results in loss of transport activity for P-glycoprotein, BCRP, and MRP2 in Caco-2 cells," Drug Metab Dispos., vol. 43, 199-207 (2015).

Sato , T. et al., "Long-term Expansion of Epithelial Organoids From Human Colon, Adenoma, Adenocarcinoma, and Barrett's Epithelium," Gastroenterology, vol. 141, 141:1762-1772 (2011).

Schoellhammer, C.M. & Traverso, G. Low-frequency ultrasound for drug delivery in the gastrointestinal tract. Expert Opin Drug Deliv 13, 1045-1048 (2016).

Schoellhammer, C.M., et al. Ultrasound-Mediated Delivery of RNA to Colonic Mucosa of Live Mice. Gastroenterology 152, 1151-1160 (2017).

Sedykh, A., et al., "Human intestinal transporter database: QSAR modeling and virtual profiling of drug uptake, efflux and interactions," Pharm Res., vol. 30: 996-1007 (2013).

Shah, P et al., "A microfluidics-based in vitro model of the gastrointestinal human-microbe interface", Nature Communications, vol. 7:11535: 16 pages (2016).

Shamir, E.R., et al., "Three-dimensional organotypic culture: experimental models of mammalian biology and disease," Nature Reviews, Molecular Cell Biology, vol. 15: 647-664 (2014).

Sjöberg, A. et al., "Comprehensive study on regional human intestinal permeability and prediction of fraction absorbed of drugs using the Ussing chamber technique," European Journal of Pharmaceutical Sciences, vol. 48: 166-180 (2013).

Tsilingiri, K. et al., "Probiotic and postbiotic activity in health and disease: Comparison on a novel polarised ex-vivo organ culture model," Gut, vol. 61(7):1007-1015 (2012).

Vadstrup, K. et al., "Validation and Optimization of an Ex Vivo Assay of Intestinal Mucosal Biopsies in Crohn's Disease: Reflects Inflammation and Drug Effects," PLOS ONE, vol. 11(5):e0155335, 18 pages (2016).

Von Erlach, T., et al. "Robotically handled whole-tissue culture system for the screening of oral drug formulations," Nat Biomed Eng, vol. 4(5):544-559(2020).

Wang, Y. et al., "A microengineered collagen scaffold for generating a polarized crypt-villus architecture of human small intestinal epithelium," Biomaterials, vol. 128:44-55 (2017).

International Search Report and Written Opinion, PCT/US2020/064329, dated Mar. 23, 2021, 18 pages.

Seyoum, A. et al., "Human Primary Cell-Based Organotypic Microtissues for Modeling Small Intestinal Drug Absorption," Pharmaceutical Research, vol. 35(4):1-18 (2018).

Stevens, L.J. et al., "A higher throughput and physiologically relevant two-compartmental human ex vivo intestinal tissue system for studying gastrointestinal processes," European Journal of Pharmaceutical Sciences, vol. 13:10 pages (2019).

\* cited by examiner

SEQUENCE LISTING

<160> NUMBER OF SEQ ID NOS: 108

<210> SEQ ID NO 1
<211> LENGTH: 21
<212> TYPE: DNA
<213> ORGANISM: Artificial Sequence
<220> FEATURE:
<223> OTHER INFORMATION: Synthetic: P-gp_F

<400> SEQUENCE: 1
ccgaatcgaa agagcaggga a                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic: P-gp_R

<400> SEQUENCE: 2
atctcctgcc gcatgatagc                                                20

<210> SEQ ID NO 3
<211> LENGTH: 20
<212> TYPE: DNA
<213> ORGANISM: Artificial Sequence
<220> FEATURE:

<223> OTHER INFORMATION: Synthetic: MRP2_F

<400> SEQUENCE: 3
aacacccata ggccggattg                                           20

<210> SEQ ID NO 4
<211> LENGTH: 20
<212> TYPE: DNA
<213> ORGANISM: Artificial Sequence
<220> FEATURE:
<223> OTHER INFORMATION: Synthetic: MRP2_R

<400> SEQUENCE: 4
aaaggcacgg ataacaggca                                           20

<210> SEQ ID NO 5
<211> LENGTH: 20
<212> TYPE: DNA
<213> ORGANISM: Artificial Sequence
<220> FEATURE:
<223> OTHER INFORMATION: Synthetic: BCRP_F

<400> SEQUENCE: 5
aaaggaacac caatggcctg                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic: BCRP_R

<400> SEQUENCE: 6
gggtcccaga atggcattga                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic: SNAT2_F

<400> SEQUENCE: 7
tgtgggcagt ggaatccttg                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic: SNAT2_R

<400> SEQUENCE: 8
ggccactggt gtatcccaaa                                           20

<210> SEQ ID NO 9
<211> LENGTH: 20
<212> TYPE: DNA
<213> ORGANISM: Artificial Sequence
<220> FEATURE:
<223> OTHER INFORMATION: Synthetic: PET1_F

<400> SEQUENCE: 9
ttgtggctct gtgctacctg                                           20

-continued

```
<210> SEQ ID NO 10
<211> LENGTH: 20
<212> TYPE: DNA
<213> ORGANISM: Artificial Sequence
<220> FEATURE:
<223> OTHER INFORMATION: Synthetic: PET1_R

<400> SEQUENCE: 10
acacacaggg ctttatcccg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic: MCT1_F

<400> SEQUENCE: 11
tgggggcttg ctgttaaact                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic: MCT1_R

<400> SEQUENCE: 12
atggtcacca atcccacagc                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic: ABCC3_F

<400> SEQUENCE: 13
accagcaagg ctacatcgtc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic: ABCC3_R

<400> SEQUENCE: 14
gatcacgcac aggaaccaga                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic: OCT1_F

<400> SEQUENCE: 15
cgttcttaga cctgttccgc a                                            21

<210> SEQ ID NO 16
<211> LENGTH: 20
<212> TYPE: DNA
<213> ORGANISM: Artificial Sequence
<220> FEATURE:
<223> OTHER INFORMATION: Synthetic: OCT1_R
```

<400> SEQUENCE: 16
aagcggtcga tgatgaggag                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic: OSTa_F

<400> SEQUENCE: 17
agcttctgag agcattgggc                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic: OSTa_R

<400> SEQUENCE: 18
tgcacatcgc gaaaaacgag                                           20

<210> SEQ ID NO 19
<211> LENGTH: 18
<212> TYPE: DNA
<213> ORGANISM: Artificial Sequence
<220> FEATURE:
<223> OTHER INFORMATION: Synthetic: Pgp_qPCR_F

<400> SEQUENCE: 19
tgctggttgc tgcttaca                                             18

<210> SEQ ID NO 20
<211> LENGTH: 23
<212> TYPE: DNA
<213> ORGANISM: Artificial Sequence
<220> FEATURE:
<223> OTHER INFORMATION: Synthetic: Pgp_qPCR_R

<400> SEQUENCE: 20
gcctatctcc tgtcgcatta tag                                       23

<210> SEQ ID NO 21
<211> LENGTH: 22
<212> TYPE: DNA
<213> ORGANISM: Artificial Sequence
<220> FEATURE:
<223> OTHER INFORMATION: Synthetic: MRP2_qPCR_F

<400> SEQUENCE: 21
ccttggtcta cacacggtaa tc                                        22

<210> SEQ ID NO 22
<211> LENGTH: 22
<212> TYPE: DNA
<213> ORGANISM: Artificial Sequence
<220> FEATURE:
<223> OTHER INFORMATION: Synthetic: MRP2_qPCR_R

<400> SEQUENCE: 22
ggacaagtgg atctgacatg ag                                        22

<210> SEQ ID NO 23
<211> LENGTH: 20

<212> TYPE: DNA
<213> ORGANISM: Artificial Sequence
<220> FEATURE:
<223> OTHER INFORMATION: Synthetic: BCRP_qPCR_F

<400> SEQUENCE: 23
tccgaccacc atgacaaatc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic: BCRP_qPCR_R

<400> SEQUENCE: 24
ccagacacac cacggataaa                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic: SNAT2_qPCR_F

<400> SEQUENCE: 25
cgcagccgta gaagaatgat                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic: SNAT2_qPCR_R

<400> SEQUENCE: 26
cgtctcaacg tggtcgtaaa                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic: PEPT1_qPCR_F

<400> SEQUENCE: 27
tgcagatccc gcagtatttc                                               20

<210> SEQ ID NO 28
<211> LENGTH: 22
<212> TYPE: DNA
<213> ORGANISM: Artificial Sequence
<220> FEATURE:
<223> OTHER INFORMATION: Synthetic: PEPT1_qPCR_R

<400> SEQUENCE: 28
gttggaagga gcctgagaat ag                                            22

<210> SEQ ID NO 29
<211> LENGTH: 21
<212> TYPE: DNA
<213> ORGANISM: Artificial Sequence
<220> FEATURE:
<223> OTHER INFORMATION: Synthetic: MCT1_qPCR_F

<400> SEQUENCE: 29

```
-continued tactgggcat gtggcataat c                                              21

<210> SEQ ID NO 30
<211> LENGTH: 20
<212> TYPE: DNA
<213> ORGANISM: Artificial Sequence
<220> FEATURE:
<223> OTHER INFORMATION: Synthetic: MCT1_qPCR_R

<400> SEQUENCE: 30
ctgctgcttc tctgctttct                                                20

<210> SEQ ID NO 31
<211> LENGTH: 22
<212> TYPE: DNA
<213> ORGANISM: Artificial Sequence
<220> FEATURE:
<223> OTHER INFORMATION: Synthetic: ABCC3_qPCR_F

<400> SEQUENCE: 31
gtcctggaca aagggacaat ag                                             22

<210> SEQ ID NO 32
<211> LENGTH: 21
<212> TYPE: DNA
<213> ORGANISM: Artificial Sequence
<220> FEATURE:
<223> OTHER INFORMATION: Synthetic: ABCC3_qPCR_R

<400> SEQUENCE: 32
tttaggcaag tccagcatct c                                              21

<210> SEQ ID NO 33
<211> LENGTH: 24
<212> TYPE: DNA
<213> ORGANISM: Artificial Sequence
<220> FEATURE:
<223> OTHER INFORMATION: Synthetic: OST-a_qPCR_F

<400> SEQUENCE: 33
gatccagaca ggactcagat aaag                                           24

<210> SEQ ID NO 34
<211> LENGTH: 21
<212> TYPE: DNA
<213> ORGANISM: Artificial Sequence
<220> FEATURE:
<223> OTHER INFORMATION: Synthetic: OST-a_qPCR_R

<400> SEQUENCE: 34
gatatgcagt gggagggtaa g                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic: OCT1_qPCR_F

<400> SEQUENCE: 35
gtcagtatgg ctgggtgtat g                                              21

<210> SEQ ID NO 36
<211> LENGTH: 21
<212> TYPE: DNA
<213> ORGANISM: Artificial Sequence
```

```
<220> FEATURE:
<223> OTHER INFORMATION: Synthetic: OCT1_qPCR_R

<400> SEQUENCE: 36
gttcacacag gactggaaga g                                              21

<210> SEQ ID NO 37
<211> LENGTH: 58
<212> TYPE: DNA
<213> ORGANISM: Artificial Sequence
<220> FEATURE:
<223> OTHER INFORMATION: Synthetic: P-gp_shRNA_334_F

<400> SEQUENCE: 37
ccggatgaca gtgtacgcct attatctcga gataataggc gtacactgtc attttttg    58

<210> SEQ ID NO 38
<211> LENGTH: 58
<212> TYPE: DNA
<213> ORGANISM: Artificial Sequence
<220> FEATURE:
<223> OTHER INFORMATION: Synthetic: P-gp_shRNA_334_R

<400> SEQUENCE: 38
aattcaaaaa atgacagtgt acgcctatta tctcgagata ataggcgtac actgtcat    58

<210> SEQ ID NO 39
<211> LENGTH: 58
<212> TYPE: DNA
<213> ORGANISM: Artificial Sequence
<220> FEATURE:
<223> OTHER INFORMATION: Synthetic: P-gp_shRNA_962_F

<400> SEQUENCE: 39
ccggtggtcc tctcaaatga atatactcga gtatattcat ttgagaggac cattttttg   58

<210> SEQ ID NO 40
<211> LENGTH: 58
<212> TYPE: DNA
<213> ORGANISM: Artificial Sequence
<220> FEATURE:
<223> OTHER INFORMATION: Synthetic: P-gp_shRNA_962_R

<400> SEQUENCE: 40
aattcaaaaa tggtcctctc aaatgaatat actcgagtat attcatttga gaggacca    58

<210> SEQ ID NO 41
<211> LENGTH: 58
<212> TYPE: DNA
<213> ORGANISM: Artificial Sequence
<220> FEATURE:
<223> OTHER INFORMATION: Synthetic: P-gp_shRNA_1391_F

<400> SEQUENCE: 41
ccggtaaggt atctgcggga aattactcga gtaatttccc gcagatacct tattttttg  58

<210> SEQ ID NO 42
<211> LENGTH: 58
<212> TYPE: DNA
<213> ORGANISM: Artificial Sequence
<220> FEATURE:
<223> OTHER INFORMATION: Synthetic: P-gp_shRNA_1391_R

<400> SEQUENCE: 42
aattcaaaaa taaggtatct gcgggaaatt actcgagtaa tttcccgcag atacctta    58
```

<210> SEQ ID NO 43
<211> LENGTH: 58
<212> TYPE: DNA
<213> ORGANISM: Artificial Sequence
<220> FEATURE:
<223> OTHER INFORMATION: Synthetic: MRP2_shRNA_292_F

<400> SEQUENCE: 43
ccggggcagc ttattcatgt atatactcga gtatatacat gaataagctg ccttttttg    58

<210> SEQ ID NO 44
<211> LENGTH: 58
<212> TYPE: DNA
<213> ORGANISM: Artificial Sequence
<220> FEATURE:
<223> OTHER INFORMATION: Synthetic: MRP2_shRNA_292_R

<400> SEQUENCE: 44
aattcaaaaa ggcagcttat tcatgtatat actcgagtat atacatgaat aagctgcc     58

<210> SEQ ID NO 45
<211> LENGTH: 58
<212> TYPE: DNA
<213> ORGANISM: Artificial Sequence
<220> FEATURE:
<223> OTHER INFORMATION: Synthetic: MRP2_shRNA_1681_F

<400> SEQUENCE: 45
ccggggatca agatcctgaa atattctcga gaatatttca ggatcttgat ccttttttg    58

<210> SEQ ID NO 46
<211> LENGTH: 58
<212> TYPE: DNA
<213> ORGANISM: Artificial Sequence
<220> FEATURE:
<223> OTHER INFORMATION: Synthetic: MRP2_shRNA_1681_R

<400> SEQUENCE: 46
aattcaaaaa ggatcaagat cctgaaatat tctcgagaat atttcaggat cttgatcc     58

<210> SEQ ID NO 47
<211> LENGTH: 58
<212> TYPE: DNA
<213> ORGANISM: Artificial Sequence
<220> FEATURE:
<223> OTHER INFORMATION: Synthetic: MRP2_shRNA_3239_F

<400> SEQUENCE: 47
ccgggggatt agcacaaggt atattctcga gaatatacct tgtgctaatc ccttttttg    58

<210> SEQ ID NO 48
<211> LENGTH: 58
<212> TYPE: DNA
<213> ORGANISM: Artificial Sequence
<220> FEATURE:
<223> OTHER INFORMATION: Synthetic: MRP2_shRNA_3239_R

<400> SEQUENCE: 48
aattcaaaaa gggattagca caaggtatat tctcgagaat ataccttgtg ctaatccc     58

<210> SEQ ID NO 49
<211> LENGTH: 58
<212> TYPE: DNA
<213> ORGANISM: Artificial Sequence
<220> FEATURE:
<223> OTHER INFORMATION: Synthetic: BCRP_shRNA_1268_F

<400> SEQUENCE: 49
ccgggcgtcc gtagcccaga taattctcga gaattatctg ggctacggac gcttttttg    58

<210> SEQ ID NO 50
<211> LENGTH: 58
<212> TYPE: DNA
<213> ORGANISM: Artificial Sequence
<220> FEATURE:
<223> OTHER INFORMATION: Synthetic: BCRP_shRNA_1268_R

<400> SEQUENCE: 50
aattcaaaaa gcgtccgtag cccagataat tctcgagaat tatctgggct acggacgc    58

<210> SEQ ID NO 51
<211> LENGTH: 58
<212> TYPE: DNA
<213> ORGANISM: Artificial Sequence
<220> FEATURE:
<223> OTHER INFORMATION: Synthetic: BCRP_shRNA_1436_F

<400> SEQUENCE: 51
ccgggtggag aagaaactct ttatactcga gtataaagag tttcttctcc acttttttg    58

<210> SEQ ID NO 52
<211> LENGTH: 58
<212> TYPE: DNA
<213> ORGANISM: Artificial Sequence
<220> FEATURE:
<223> OTHER INFORMATION: Synthetic: BCRP_shRNA_1436_R

<400> SEQUENCE: 52
aattcaaaaa gtggagaaga aactctttat actcgagtat aaagagtttc ttctccac    58

<210> SEQ ID NO 53
<211> LENGTH: 58
<212> TYPE: DNA
<213> ORGANISM: Artificial Sequence
<220> FEATURE:
<223> OTHER INFORMATION: Synthetic: BCRP_shRNA_960_F

<400> SEQUENCE: 53
ccggacttct tcctggacgt cattactcga gtaatgacgt ccaggaagaa gtttttttg    58

<210> SEQ ID NO 54
<211> LENGTH: 58
<212> TYPE: DNA
<213> ORGANISM: Artificial Sequence
<220> FEATURE:
<223> OTHER INFORMATION: Synthetic: BCRP_shRNA_960_R

<400> SEQUENCE: 54
aattcaaaaa acttcttcct ggacgtcatt actcgagtaa tgacgtccag gaagaagt    58

<210> SEQ ID NO 55
<211> LENGTH: 58
<212> TYPE: DNA
<213> ORGANISM: Artificial Sequence
<220> FEATURE:
<223> OTHER INFORMATION: Synthetic: SNAT2_shRNA_251_F

<400> SEQUENCE: 55
ccggcctttg aatgtcagt atttactcga gtaaatactg acattccaaa ggtttttg    58

<210> SEQ ID NO 56

```
<211> LENGTH: 58
<212> TYPE: DNA
<213> ORGANISM: Artificial Sequence
<220> FEATURE:
<223> OTHER INFORMATION: Synthetic: SNAT2_shRNA_251_R

<400> SEQUENCE: 56
aattcaaaaa cctttggaat gtcagtattt actcgagtaa atactgacat tccaaagg     58

<210> SEQ ID NO 57
<211> LENGTH: 58
<212> TYPE: DNA
<213> ORGANISM: Artificial Sequence
<220> FEATURE:
<223> OTHER INFORMATION: Synthetic: SNAT2_shRNA_625_F

<400> SEQUENCE: 57
ccggttgtca ctgctgagga atttactcga gtaaattcct cagcagtgac aattttg      58

<210> SEQ ID NO 58
<211> LENGTH: 58
<212> TYPE: DNA
<213> ORGANISM: Artificial Sequence
<220> FEATURE:
<223> OTHER INFORMATION: Synthetic: SNAT2_shRNA_625_R

<400> SEQUENCE: 58
aattcaaaaa ttgtcactgc tgaggaattt actcgagtaa attcctcagc agtgacaa     58

<210> SEQ ID NO 59
<211> LENGTH: 58
<212> TYPE: DNA
<213> ORGANISM: Artificial Sequence
<220> FEATURE:
<223> OTHER INFORMATION: Synthetic: SNAT2_shRNA_738_F

<400> SEQUENCE: 59
ccggtgtgga agttgctata ataatctcga gattattata gcaacttcca cattttg      58

<210> SEQ ID NO 60
<211> LENGTH: 58
<212> TYPE: DNA
<213> ORGANISM: Artificial Sequence
<220> FEATURE:
<223> OTHER INFORMATION: Synthetic: SNAT2_shRNA_738_R

<400> SEQUENCE: 60
aattcaaaaa tgtggaagtt gctataataa tctcgagatt attatagcaa cttccaca     58

<210> SEQ ID NO 61
<211> LENGTH: 58
<212> TYPE: DNA
<213> ORGANISM: Artificial Sequence
<220> FEATURE:
<223> OTHER INFORMATION: Synthetic: PEPT1_shRNA_787_F

<400> SEQUENCE: 61
ccgggactgg gccaaggaga aatatctcga gatatttctc cttggcccag tcttttg      58

<210> SEQ ID NO 62
<211> LENGTH: 58
<212> TYPE: DNA
<213> ORGANISM: Artificial Sequence
<220> FEATURE:
<223> OTHER INFORMATION: Synthetic: PEPT1_shRNA_787_R

<400> SEQUENCE: 62
```
aattcaaaaa gactgggcca aggagaaata tctcgagata tttctccttg gcccagtc    58

<210> SEQ ID NO 63
<211> LENGTH: 58
<212> TYPE: DNA
<213> ORGANISM: Artificial Sequence
<220> FEATURE:
<223> OTHER INFORMATION: Synthetic: PEPT1_shRNA_1296_F

<400> SEQUENCE: 63
ccggcaacaa actgacaagt ataaactcga gtttatactt gtcagtttgt tgtttttg    58

<210> SEQ ID NO 64
<211> LENGTH: 58
<212> TYPE: DNA
<213> ORGANISM: Artificial Sequence
<220> FEATURE:
<223> OTHER INFORMATION: Synthetic: PEPT1_shRNA_1296_R

<400> SEQUENCE: 64
aattcaaaaa caacaaactg acaagtataa actcgagttt atacttgtca gtttgttg    58

<210> SEQ ID NO 65
<211> LENGTH: 58
<212> TYPE: DNA
<213> ORGANISM: Artificial Sequence
<220> FEATURE:
<223> OTHER INFORMATION: Synthetic: PEPT1_shRNA_1968_F

<400> SEQUENCE: 65
ccggcctcgc cgtctgcata atattctcga gaatattatg cagacggcga ggttttttg    58

<210> SEQ ID NO 66
<211> LENGTH: 58
<212> TYPE: DNA
<213> ORGANISM: Artificial Sequence
<220> FEATURE:
<223> OTHER INFORMATION: Synthetic: PEPT1_shRNA_1968_R

<400> SEQUENCE: 66
aattcaaaaa cctcgccgtc tgcataatat tctcgagaat attatgcaga cggcgagg    58

<210> SEQ ID NO 67
<211> LENGTH: 58
<212> TYPE: DNA
<213> ORGANISM: Artificial Sequence
<220> FEATURE:
<223> OTHER INFORMATION: Synthetic: MCT1_shRNA_256_F

<400> SEQUENCE: 67
ccggagtatc ctggtgaata aatatctcga gatatttatt caccaggata ctttttg    58

<210> SEQ ID NO 68
<211> LENGTH: 58
<212> TYPE: DNA
<213> ORGANISM: Artificial Sequence
<220> FEATURE:
<223> OTHER INFORMATION: Synthetic: MCT1_shRNA_256_R

<400> SEQUENCE: 68
aattcaaaaa agtatcctgg tgaataaata tctcgagata tttattcacc aggatact    58

<210> SEQ ID NO 69
<211> LENGTH: 58
<212> TYPE: DNA

```
<213> ORGANISM: Artificial Sequence
<220> FEATURE:
<223> OTHER INFORMATION: Synthetic: MCT1_shRNA_631_F

<400> SEQUENCE: 69
ccggccaacc actgcagaca aatatctcga gatatttgtc tgcagtggtt ggttttttg    58

<210> SEQ ID NO 70
<211> LENGTH: 58
<212> TYPE: DNA
<213> ORGANISM: Artificial Sequence
<220> FEATURE:
<223> OTHER INFORMATION: Synthetic: MCT1_shRNA_631_R

<400> SEQUENCE: 70
aattcaaaaa ccaaccactg cagacaaata tctcgagata tttgtctgca gtggttgg    58

<210> SEQ ID NO 71
<211> LENGTH: 58
<212> TYPE: DNA
<213> ORGANISM: Artificial Sequence
<220> FEATURE:
<223> OTHER INFORMATION: Synthetic: MCT1_shRNA_1130_F

<400> SEQUENCE: 71
ccggggtggc tcagctcagt attatctcga gataatactg agctgagcca ccttttttg    58

<210> SEQ ID NO 72
<211> LENGTH: 58
<212> TYPE: DNA
<213> ORGANISM: Artificial Sequence
<220> FEATURE:
<223> OTHER INFORMATION: Synthetic: MCT1_shRNA_1130_R

<400> SEQUENCE: 72
aattcaaaaa ggtggctcag ctcagtatta tctcgagata atactgagct gagccacc    58

<210> SEQ ID NO 73
<211> LENGTH: 58
<212> TYPE: DNA
<213> ORGANISM: Artificial Sequence
<220> FEATURE:
<223> OTHER INFORMATION: Synthetic: ABCC3_shRNA_1095_F

<400> SEQUENCE: 73
ccggcagcat cctgatcaga tttatctcga gataaatctg atcaggatgc tgttttttg    58

<210> SEQ ID NO 74
<211> LENGTH: 58
<212> TYPE: DNA
<213> ORGANISM: Artificial Sequence
<220> FEATURE:
<223> OTHER INFORMATION: Synthetic: ABCC3_shRNA_1095_R

<400> SEQUENCE: 74
aattcaaaaa cagcatcctg atcagattta tctcgagata aatctgatca ggatgctg    58

<210> SEQ ID NO 75
<211> LENGTH: 58
<212> TYPE: DNA
<213> ORGANISM: Artificial Sequence
<220> FEATURE:
<223> OTHER INFORMATION: Synthetic: ABCC3_shRNA_2329_F

<400> SEQUENCE: 75
ccggattgga gagaagggca ttaatctcga gattaatgcc cttctctcca atttttttg    58
```

<210> SEQ ID NO 76
<211> LENGTH: 58
<212> TYPE: DNA
<213> ORGANISM: Artificial Sequence
<220> FEATURE:
<223> OTHER INFORMATION: Synthetic: ABCC3_shRNA_2329_R

<400> SEQUENCE: 76
aattcaaaaa attggagaga agggcattaa tctcgagatt aatgcccttc tctccaat    58

<210> SEQ ID NO 77
<211> LENGTH: 58
<212> TYPE: DNA
<213> ORGANISM: Artificial Sequence
<220> FEATURE:
<223> OTHER INFORMATION: Synthetic: ABCC3_shRNA_1098_F

<400> SEQUENCE: 77
ccggcatcct gatcagattt atttcctcga ggaaataaat ctgatcagga tgttttttg    58

<210> SEQ ID NO 78
<211> LENGTH: 58
<212> TYPE: DNA
<213> ORGANISM: Artificial Sequence
<220> FEATURE:
<223> OTHER INFORMATION: Synthetic: ABCC3_shRNA_1098_R

<400> SEQUENCE: 78
aattcaaaaa catcctgatc agatttattt cctcgaggaa ataaatctga tcaggatg    58

<210> SEQ ID NO 79
<211> LENGTH: 58
<212> TYPE: DNA
<213> ORGANISM: Artificial Sequence
<220> FEATURE:
<223> OTHER INFORMATION: Synthetic: OST-a_shRNA_273_F

<400> SEQUENCE: 79
ccgggaagat attggaagtc aattactcga gtaattgact ccaatatct tcttttg    58

<210> SEQ ID NO 80
<211> LENGTH: 58
<212> TYPE: DNA
<213> ORGANISM: Artificial Sequence
<220> FEATURE:
<223> OTHER INFORMATION: Synthetic: OST-a_shRNA_273_R

<400> SEQUENCE: 80
aattcaaaaa gaagatattg gaagtcaatt actcgagtaa ttgacttcca atatcttc    58

<210> SEQ ID NO 81
<211> LENGTH: 58
<212> TYPE: DNA
<213> ORGANISM: Artificial Sequence
<220> FEATURE:
<223> OTHER INFORMATION: Synthetic: OST-a_shRNA_818_F

<400> SEQUENCE: 81
ccggtcatcc ctgacggcat ctatactcga gtatagatgc cgtcagggat gattttg    58

<210> SEQ ID NO 82
<211> LENGTH: 58
<212> TYPE: DNA
<213> ORGANISM: Artificial Sequence
<220> FEATURE:

<223> OTHER INFORMATION: Synthetic: OST-a_shRNA_818_R

<400> SEQUENCE: 82
aattcaaaaa tcatccctga cggcatctat actcgagtat agatgccgtc agggatga    58

<210> SEQ ID NO 83
<211> LENGTH: 58
<212> TYPE: DNA
<213> ORGANISM: Artificial Sequence
<220> FEATURE:
<223> OTHER INFORMATION: Synthetic: OST-a_shRNA_988_F

<400> SEQUENCE: 83
ccggctattc caggtgctcc ttattctcga gaataaggag cacctggaat agttttg    58

<210> SEQ ID NO 84
<211> LENGTH: 58
<212> TYPE: DNA
<213> ORGANISM: Artificial Sequence
<220> FEATURE:
<223> OTHER INFORMATION: Synthetic: OST-a_shRNA_988_R

<400> SEQUENCE: 84
aattcaaaaa ctattccagg tgctccttat tctcgagaat aaggagcacc tggaatag    58

<210> SEQ ID NO 85
<211> LENGTH: 58
<212> TYPE: DNA
<213> ORGANISM: Artificial Sequence
<220> FEATURE:
<223> OTHER INFORMATION: Synthetic: OCT1_shRNA_956_F

<400> SEQUENCE: 85
ccgggagaaa cactcaagca ataaactcga gtttattgct tgagtgtttc tcttttg    58

<210> SEQ ID NO 86
<211> LENGTH: 58
<212> TYPE: DNA
<213> ORGANISM: Artificial Sequence
<220> FEATURE:
<223> OTHER INFORMATION: Synthetic: OCT1_shRNA_956_R

<400> SEQUENCE: 86
aattcaaaaa gagaaacact caagcaataa actcgagttt attgcttgag tgtttctc    58

<210> SEQ ID NO 87
<211> LENGTH: 58
<212> TYPE: DNA
<213> ORGANISM: Artificial Sequence
<220> FEATURE:
<223> OTHER INFORMATION: Synthetic: OCT1_shRNA_739_F

<400> SEQUENCE: 87
ccggacacac tgatcacaga atttgctcga gcaaattctg tgatcagtgt gttttttg    58

<210> SEQ ID NO 88
<211> LENGTH: 58
<212> TYPE: DNA
<213> ORGANISM: Artificial Sequence
<220> FEATURE:
<223> OTHER INFORMATION: Synthetic: OCT1_shRNA_739_R

<400> SEQUENCE: 88
aattcaaaaa acacactgat cacagaattt gctcgagcaa attctgtgat cagtgtgt    58

-continued

```
<210> SEQ ID NO 89
<211> LENGTH: 58
<212> TYPE: DNA
<213> ORGANISM: Artificial Sequence
<220> FEATURE:
<223> OTHER INFORMATION: Synthetic: OCT1_shRNA_1688_F

<400> SEQUENCE: 89
ccgggcccag agacaacatg atttactcga gtaaatcatg ttgtctctgg gctttttg     58

<210> SEQ ID NO 90
<211> LENGTH: 58
<212> TYPE: DNA
<213> ORGANISM: Artificial Sequence
<220> FEATURE:
<223> OTHER INFORMATION: Synthetic: OCT1_shRNA_1688_R

<400> SEQUENCE: 90
aattcaaaaa gcccagagac aacatgattt actcgagtaa atcatgttgt ctctgggc     58

<210> SEQ ID NO 91
<211> LENGTH: 23
<212> TYPE: DNA
<213> ORGANISM: Artificial Sequence
<220> FEATURE:
<223> OTHER INFORMATION: Synthetic: Pgp_sense
<220> FEATURE:
<221> NAME/KEY: misc_feature
<222> LOCATION: (22)..(23)
<223> OTHER INFORMATION: dT

<400> SEQUENCE: 91
augacagugu acgccuauua utt                                            23

<210> SEQ ID NO 92
<211> LENGTH: 23
<212> TYPE: DNA
<213> ORGANISM: Artificial Sequence
<220> FEATURE:
<223> OTHER INFORMATION: Synthetic: Pgp_anti
<220> FEATURE:
<221> NAME/KEY: misc_feature
<222> LOCATION: (22)..(23)
<223> OTHER INFORMATION: dT

<400> SEQUENCE: 92
auaauaggcg uacacuguca utt                                            23

<210> SEQ ID NO 93
<211> LENGTH: 23
<212> TYPE: DNA
<213> ORGANISM: Artificial Sequence
<220> FEATURE:
<223> OTHER INFORMATION: Synthetic: MRP2_sense
<220> FEATURE:
<221> NAME/KEY: misc_feature
<222> LOCATION: (22)..(23)
<223> OTHER INFORMATION: dT

<400> SEQUENCE: 93
ggcagcuuau ucauguauau att                                            23

<210> SEQ ID NO 94
<211> LENGTH: 23
<212> TYPE: DNA
<213> ORGANISM: Artificial Sequence
<220> FEATURE:
<223> OTHER INFORMATION: Synthetic: MRP2_anti
<220> FEATURE:
```

```
<221> NAME/KEY: misc_feature
<222> LOCATION: (22)..(23)
<223> OTHER INFORMATION: dT

<400> SEQUENCE: 94
uauauacaug aauaagcugc ctt                                              23

<210> SEQ ID NO 95
<211> LENGTH: 23
<212> TYPE: DNA
<213> ORGANISM: Artificial Sequence
<220> FEATURE:
<223> OTHER INFORMATION: Synthetic: BCRP_sense
<220> FEATURE:
<221> NAME/KEY: misc_feature
<222> LOCATION: (22)..(23)
<223> OTHER INFORMATION: dT

<400> SEQUENCE: 95
acuucuuccu ggacgucauu att                                              23

<210> SEQ ID NO 96
<211> LENGTH: 23
<212> TYPE: DNA
<213> ORGANISM: Artificial Sequence
<220> FEATURE:
<223> OTHER INFORMATION: Synthetic: BCRP_anti
<220> FEATURE:
<221> NAME/KEY: misc_feature
<222> LOCATION: (22)..(23)
<223> OTHER INFORMATION: dT

<400> SEQUENCE: 96
uaaugacguc caggaagaag utt                                              23

<210> SEQ ID NO 97
<211> LENGTH: 23
<212> TYPE: DNA
<213> ORGANISM: Artificial Sequence
<220> FEATURE:
<223> OTHER INFORMATION: Synthetic: SNAT2_sense
<220> FEATURE:
<221> NAME/KEY: misc_feature
<222> LOCATION: (22)..(23)
<223> OTHER INFORMATION: dT

<400> SEQUENCE: 97
uugucacugc ugaggaauuu att                                              23

<210> SEQ ID NO 98
<211> LENGTH: 23
<212> TYPE: DNA
<213> ORGANISM: Artificial Sequence
<220> FEATURE:
<223> OTHER INFORMATION: Synthetic: SNAT2_anti
<220> FEATURE:
<221> NAME/KEY: misc_feature
<222> LOCATION: (22)..(23)
<223> OTHER INFORMATION: dT

<400> SEQUENCE: 98
uaaauuccuc agcagugaca att                                              23

<210> SEQ ID NO 99
<211> LENGTH: 23
<212> TYPE: DNA
<213> ORGANISM: Artificial Sequence
<220> FEATURE:
<223> OTHER INFORMATION: Synthetic: PEPT1_sense
```

```
<220> FEATURE:
<221> NAME/KEY: misc_feature
<222> LOCATION: (22)..(23)
<223> OTHER INFORMATION: dT

<400> SEQUENCE: 99
caacaaacug acaaguauaa att                                              23

<210> SEQ ID NO 100
<211> LENGTH: 23
<212> TYPE: DNA
<213> ORGANISM: Artificial Sequence
<220> FEATURE:
<223> OTHER INFORMATION: Synthetic: PEPT1_anti
<220> FEATURE:
<221> NAME/KEY: misc_feature
<222> LOCATION: (22)..(23)
<223> OTHER INFORMATION: dT

<400> SEQUENCE: 100
uuuauacuug ucaguuuguu gtt                                              23

<210> SEQ ID NO 101
<211> LENGTH: 23
<212> TYPE: DNA
<213> ORGANISM: Artificial Sequence
<220> FEATURE:
<223> OTHER INFORMATION: Synthetic: MCT1_sense
<220> FEATURE:
<221> NAME/KEY: misc_feature
<222> LOCATION: (22)..(23)
<223> OTHER INFORMATION: dT

<400> SEQUENCE: 101
gguggcucag cucaguauua utt                                              23

<210> SEQ ID NO 102
<211> LENGTH: 23
<212> TYPE: DNA
<213> ORGANISM: Artificial Sequence
<220> FEATURE:
<223> OTHER INFORMATION: Synthetic: MCT1_anti
<220> FEATURE:
<221> NAME/KEY: misc_feature
<222> LOCATION: (22)..(23)
<223> OTHER INFORMATION: dT

<400> SEQUENCE: 102
auaauacuga gcugagccac ctt                                              23

<210> SEQ ID NO 103
<211> LENGTH: 23
<212> TYPE: DNA
<213> ORGANISM: Artificial Sequence
<220> FEATURE:
<223> OTHER INFORMATION: Synthetic: ABCC3_sense
<220> FEATURE:
<221> NAME/KEY: misc_feature
<222> LOCATION: (22)..(23)
<223> OTHER INFORMATION: dT

<400> SEQUENCE: 103
cagcauccug aucagauuua utt                                              23

<210> SEQ ID NO 104
<211> LENGTH: 23
<212> TYPE: DNA
<213> ORGANISM: Artificial Sequence
<220> FEATURE:
```

```
<223> OTHER INFORMATION: Synthetic: ABCC3_anti
<220> FEATURE:
<221> NAME/KEY: misc_feature
<222> LOCATION: (22)..(23)
<223> OTHER INFORMATION: dT

<400> SEQUENCE: 104
auaaaucuga ucaggaugcu gtt                                              23

<210> SEQ ID NO 105
<211> LENGTH: 23
<212> TYPE: DNA
<213> ORGANISM: Artificial Sequence
<220> FEATURE:
<223> OTHER INFORMATION: Synthetic: OST-a_sense
<220> FEATURE:
<221> NAME/KEY: misc_feature
<222> LOCATION: (22)..(23)
<223> OTHER INFORMATION: dT

<400> SEQUENCE: 105
gaagauauug gaagucaauu att                                              23

<210> SEQ ID NO 106
<211> LENGTH: 23
<212> TYPE: DNA
<213> ORGANISM: Artificial Sequence
<220> FEATURE:
<223> OTHER INFORMATION: Synthetic: OST-a_anti
<220> FEATURE:
<221> NAME/KEY: misc_feature
<222> LOCATION: (22)..(23)
<223> OTHER INFORMATION: dT

<400> SEQUENCE: 106
uaauugacuu ccaauaucuu ctt                                              23

<210> SEQ ID NO 107
<211> LENGTH: 23
<212> TYPE: DNA
<213> ORGANISM: Artificial Sequence
<220> FEATURE:
<223> OTHER INFORMATION: Synthetic: OCT1_sense
<220> FEATURE:
<221> NAME/KEY: misc_feature
<222> LOCATION: (22)..(23)
<223> OTHER INFORMATION: dT

<400> SEQUENCE: 107
acacacugau cacagaauuu gtt                                              23

<210> SEQ ID NO 108
<211> LENGTH: 23
<212> TYPE: DNA
<213> ORGANISM: Artificial Sequence
<220> FEATURE:
<223> OTHER INFORMATION: Synthetic: OCT1_anti
<220> FEATURE:
<221> NAME/KEY: misc_feature
<222> LOCATION: (22)..(23)
<223> OTHER INFORMATION: dT

<400> SEQUENCE: 108
caaauucugu gaucagugug utt                                              23
```

EX VIVO SYSTEM FOR DETERMINING MULTIPLE DRUG-DRUG TRANSPORTER INTERACTIONS AND METHODS OF USE THEREOF

RELATED APPLICATIONS

This application claims the benefit of U.S. Provisional Application Ser. No. 62/946,336, filed on Dec. 10, 2019. The entire contents of the above-referenced application is incorporated herein by this reference.

STATEMENT AS TO FEDERALLY SPONSORED RESEARCH

This invention was made with Government support under Grant No. R01 EB000244 awarded by the National Institute of Health. The government has certain rights in the invention.

REFERENCE TO SEQUENCE LISTING

The instant application contains a Sequence Listing which has been submitted electronically in ASCII format via EFS-Web and is hereby incorporated by reference in its entirety. Said ASCII copy, created Apr. 15, 2021, is named "MITN-070 Sequence-Listing.txt" and is 22793 bytes in size.

BACKGROUND

Drug transporters are membrane proteins that have been recognized as major determinants of the pharmacokinetics, biodistribution, and efficacy of drugs. A major focus in drug discovery and development is to understand the transportome and the interaction between drugs and their transporters, specifically in the context of their role in determining intestinal absorption of orally administered medications. Current systems used to study transporter-drug interactions include engineered cell monolayers and vesicular assays (Fekete, Z. et al. J. Membr Biol, vol 248: 967-977 (2015); International Transporter Consortium, et al. Nat Rev Drug Discov, vol 9: 215-236 (2010); Pratt, J. et al. Curr Protoc Toxicol, Chapter 23, Unit 23 22 (2012); Sampson, K. E. et al. Drug Metab Dispos, vol, 43: 199-207 (2015)). Such simplified models often fail to accurately capture the complex and dynamic cellular context and do not capture differences in transporter expression levels or the cellular heterogeneity of native tissues (Balimane, P. V. et al. Drug Discov Today, vol 10: 335-343 (2005); Ingels, F. M. et al., J Pharm Sci, vol 92: 1545-4558 (2003); Fagerholm, U. J Pharm Pharmacol, vol. 59: 905-916 (2007); Sun, D. et al., Pharm Res, vol. 19: 1400-1416 (2002); Teskin, Z. S. et al. AAPS J, vol 12: 238-241 (2010)). Knockout and humanized mice can act as models with higher physiological relevance, but low throughput and high cost limit their broader application (International Transporter Consortium, et al. Nat Rev Drug Discov, vol 9: 215-236 (2010); Musther, H. et al. Eur J Pharm Sci, vol 57: 280-291 (2014)). Accordingly, there remains a need for a system that enables the controlled and fine-tuned manipulation of individual expression levels to study the complex interplay between transporters and their joint impact on the bioavailability of medications.

SUMMARY OF THE DISCLOSURE

In some aspects, the disclosure provides an ex vivo system for use in determining multiplex interactions between a candidate drug and two or more drug transporters in an intestinal tissue explant, the system comprising:
(i) an intestinal tissue explant in planar contact with a substrate, wherein the intestinal tissue explant comprises intestinal epithelium from a large, non-human, mammalian gastrointestinal tract, wherein the intestinal epithelium comprises epithelial cells having a polarity in the tissue explant and two or more drug transporters, and wherein the tissue explant provides a luminal surface and a basolateral surface; and
(ii) two or more agents for use in reducing or eliminating expression of the two or more drug transporters in the intestinal tissue explant, wherein the two or more drug transporters are on the luminal surface of the tissue explant and selected from: p-glycoprotein (p-gp), breast cancer resistance protein (BCRP), multidrug resistance 2 (MRP2), monocarboxylate transporter 1 (MCT1), and peptide transporter 1 (PEPT1),
wherein the system provides for multiplex interactions between the candidate drug and the two or more drug transporters to be determined by contacting the intestinal tissue explant with the candidate drug before and after expression of the two or more drug transporters is reduced or eliminated in the intestinal tissue explant.

In other aspects, the disclosure provides a kit comprising an ex vivo system for use in determining multiplex interactions between a candidate drug and two or more drug transporters in an intestinal tissue explant, the kit comprising:
(i) an intestinal tissue explant comprising intestinal epithelium from a large, non-human, mammalian gastrointestinal tract, wherein the intestinal epithelium comprises epithelial cells having a polarity in the tissue explant and two or more intact drug transporters, wherein the tissue explant provides a luminal surface and a basolateral surface, and wherein the polarity of the epithelial cells is maintained in the tissue explant;
(ii) two or more agents for use in reducing or eliminating expression of at least two drug transporters selected from: p-gp, BCRP, MRP2, MCT1, and PEPT1; and
(iii) instructions for use of the system to determine multiplex interactions between the candidate drug and the two or more drug transporters, wherein the instructions comprise contacting the intestinal tissue explant with the candidate drug before and after expression of the two or more drug transporters is reduced or eliminated in the intestinal tissue explant.

In other aspects, the disclosure provides a method for determining multiplex interactions between a candidate drug and two or more drug transporters, comprising:
(i) obtaining an intestinal tissue explant comprising intestinal epithelium from a large, non-human, mammalian gastrointestinal tract, wherein the tissue explant provides a luminal surface and a basolateral surface, wherein the intestinal epithelium comprises epithelial cells having a polarity in the tissue explant and two or more intact drug transporters located at the luminal surface of the tissue explant and is selected from the group: p-gp, BCRP, MRP2, MCT1, and PEPT1, and wherein the polarity of the epithelial cells is maintained in the tissue explant;
(ii) contacting the tissue explant with two or more agents for reducing or eliminating expression of the two or more drug transporters to generate a modified tissue explant;
(iii) contacting the tissue explant of (i) or the modified tissue explant of (ii) with the candidate drug;

(iv) determining adsorption of the candidate drug by detecting the presence of the drug at the luminal surface and at the basolateral surface, wherein presence of the drug at the basolateral surface indicates ability of the drug to be absorbed through the tissue explant; and (v) comparing absorption between the tissue explant, modified or unmodified, thereby determining multiplex interactions between the candidate drugs and the two or more drug transporters.

In further aspects, the disclosure provides a method for determining multiplex interactions between a candidate drug and two or more drug transporters, comprising:

(i) obtaining an intestinal tissue explant comprising intestinal epithelium from a large, non-human, mammalian gastrointestinal tract, wherein the tissue explant provides a luminal surface and a basolateral surface, wherein the intestinal epithelium comprises epithelial cells having a polarity in the tissue explant and two or more intact drug transporters located at the luminal surface of the tissue explant and is selected from the group: p-gp, BCRP, MRP2, MCT1, and PEPT1, and wherein the polarity of the epithelial cells is maintained in the tissue explant;

(ii) contacting the tissue explant with two or more siRNA molecules for reducing or eliminating expression of the two or more drug transporters to generate a modified tissue explant, wherein the siRNA molecules are formulated in a solution for ultrasound delivery;

(iii) contacting the tissue explant of (i) or the modified tissue explant of (ii) with the candidate drug;

(iv) determining adsorption of the candidate drug by detecting the presence of the drug at the luminal surface and at the basolateral surface, wherein presence of the drug at the basolateral surface indicates ability of the drug to be absorbed through the tissue explant; and (v) comparing absorption between the tissue explant, modified or unmodified, thereby determining multiplex interactions between the candidate drugs and the two or more drug transporters.

In some aspects, (ii) comprises contacting the tissue explant with ultrasound to deliver the siRNA molecules.

In some aspects, the method comprises contacting the intestinal tissue explant with the two or more agents individually or in combination to determine multiplex interactions.

In any of the foregoing or related aspects, the two or more drug transporters comprise (i) p-gp and BCRP; (ii) p-gp and MRP2; (iii) BCRP and MRP2; or (iv) p-gp, BCRP and MRP2.

In any of the foregoing or related aspects, the two or more agents comprise two or more inhibitory RNA molecules. In some aspects, the two or more inhibitory RNA molecules are two or more siRNA molecules. In some aspects, the two or more siRNA molecules target (i) p-gp and BCRP; (ii) p-gp and MRP2; (iii) BCRP and MRP2; or (iv) p-gp, BCRP and MRP2. In some aspects, the two or more siRNA molecules are selected from the group consisting of:

(i) a p-gp targeting siRNA molecule comprising a sense strand comprising the nucleotide sequence set forth in SEQ ID NO: 91 and an antisense strand comprising the nucleotide sequence set forth in SEQ ID NO: 92;

(ii) a MRP2 targeting siRNA molecule comprising a sense strand comprising the nucleotide sequence set forth in SEQ ID NO: 93 and an antisense strand comprising the nucleotide sequence set forth in SEQ ID NO: 94;

(iii) a BCRP targeting siRNA molecule comprising a sense strand comprising the nucleotide sequence set forth in SEQ ID NO: 95 and an antisense strand comprising the nucleotide sequence set forth in SEQ ID NO: 96;

(iv) a PEPT1 targeting siRNA molecule comprising a sense strand comprising the nucleotide sequence set forth in SEQ ID NO: 99 and an antisense strand comprising the nucleotide sequence set forth in SEQ ID NO: 100; and (v) a MCT1 targeting siRNA molecule comprising a sense strand comprising the nucleotide sequence set forth in SEQ ID NO: 101 and an antisense strand comprising the nucleotide sequence set forth in SEQ ID NO: 102.

In some aspects, any of the ex vivo systems or kits described herein comprise:

(i) a p-gp targeting siRNA molecule comprising a sense strand comprising the nucleotide sequence set forth in SEQ ID NO: 91 and an antisense strand comprising the nucleotide sequence set forth in SEQ ID NO: 92;

(ii) a MRP2 targeting siRNA molecule comprising a sense strand comprising the nucleotide sequence set forth in SEQ ID NO: 93 and an antisense strand comprising the nucleotide sequence set forth in SEQ ID NO: 94; and (iii) a BCRP targeting siRNA molecule comprising a sense strand comprising the nucleotide sequence set forth in SEQ ID NO: 95 and an antisense strand comprising the nucleotide sequence set forth in SEQ ID NO: 96.

In some aspects, any of the methods described herein comprise contacting the intestinal tissue explant with:

(i) a p-gp targeting siRNA molecule comprising a sense strand comprising the nucleotide sequence set forth in SEQ ID NO: 91 and an antisense strand comprising the nucleotide sequence set forth in SEQ ID NO: 92;

(ii) a MRP2 targeting siRNA molecule comprising a sense strand comprising the nucleotide sequence set forth in SEQ ID NO: 93 and an antisense strand comprising the nucleotide sequence set forth in SEQ ID NO: 94; and (iii) a BCRP targeting siRNA molecule comprising a sense strand comprising the nucleotide sequence set forth in SEQ ID NO: 95 and an antisense strand comprising the nucleotide sequence set forth in SEQ ID NO: 96.

In some aspects, any of the methods described herein comprise contacting the intestinal tissue explant with:

(i) a p-gp targeting siRNA molecule comprising a sense strand comprising the nucleotide sequence set forth in SEQ ID NO: 91 and an antisense strand comprising the nucleotide sequence set forth in SEQ ID NO: 92;

(ii) a MRP2 targeting siRNA molecule comprising a sense strand comprising the nucleotide sequence set forth in SEQ ID NO: 93 and an antisense strand comprising the nucleotide sequence set forth in SEQ ID NO: 94; and (iii) a BCRP targeting siRNA molecule comprising a sense strand comprising the nucleotide sequence set forth in SEQ ID NO: 95 and an antisense strand comprising the nucleotide sequence set forth in SEQ ID NO: 96, individually and in any combination thereof.

In any of the foregoing or related aspects, an siRNA molecule is formulated in a solution for ultrasound delivery to the intestinal tissue explant. In some aspects, the siRNA molecule is formulated in PBS for ultrasound delivery.

In any of the foregoing or related aspects, an siRNA molecule is specific for porcine nucleic acids. In some aspects, an siRNA molecule is specific for a porcine genomic target. In some aspects, an siRNA molecule is specific for a porcine mRNA target.

In other aspects, the two or more agents comprise two or more gRNA molecules for use with a CRISPR/Cas system to eliminate expression of the two or more drug transporters.

In yet other aspects, the two or more agents are two or more small molecules that inhibit activity of the two or more drug transporters. In some aspects, the two or more small molecules is selected from the group:
  (i) a p-gp small molecule inhibitor selected from colchicine, irinotecan, loperamicine, nicardipine and ranitidine;
  (ii) a BCRP small molecule inhibitor selected from 4-methylumelliferone sulfate, daunorubicin, mitoxantrone, pitavastatin, and rosuvastatin;
  (iii) a MRP2 small molecule inhibitor selected from etoposide, irinotecan, olmesartan, para-aminohippurate, and valsartsn;
  (iv) a MCT1 small molecule inhibitor selected from paraquat, ganciclovir, and acyclovir; and
  (v) a PEPT1 small molecule inhibitor selected from amoxicillin, cefadroxil, enalapril, valacyclovir, and cephalexin.

In some aspects, the agents for reducing or eliminating expression of two or more drug transporters comprises any combinations of the agents disclosed herein.

In some aspects, the ex vivo systems and kits described herein further comprise a machine learning algorithm to identify interactions between the candidate drug and two or more drug transporters. In some aspects, the methods described herein further comprise using a machine learning algorithm to identify interactions between the candidate drug and more than two drug transporters.

In some aspects, the disclosure provides a method for investigating known multiplex interactions between a candidate drug and two or more drug transporters, comprising:
  (i) obtaining an intestinal tissue explant comprising intestinal epithelium from a large, non-human, mammalian gastrointestinal tract, wherein the intestinal epithelium comprises epithelial cells having a polarity in the tissue explant and the two or more drug transporters, wherein the tissue explant provides a luminal surface and a basolateral surface, and wherein the polarity of the epithelial cells is maintained in the tissue explant;
  (ii) contacting the tissue explant with two or more agents for reducing or eliminating expression of the two or more drug transporters to generate a modified tissue explant, wherein the two or more drug transporters are reduced or eliminated individually or in combination;
  (iii) contacting the tissue explant of (i) or the modified tissue explant of (ii) with the candidate drug;
  (iv) determining adsorption of the candidate drug by detecting the presence of the drug at the luminal surface and at the basolateral surface, wherein presence of the drug at the basolateral surface indicates ability of the drug to be absorbed through the tissue explant; and
  (v) comparing absorption between the tissue explant, modified or unmodified, thereby investigating the known multiplex interactions between the candidate drug and two or more drug transporters.

In some aspects, the disclosure provides a method for investigating known multiplex interactions between a candidate drug and two or more drug transporters, comprising:
  (i) obtaining an intestinal tissue explant comprising intestinal epithelium from a large, non-human, mammalian gastrointestinal tract, wherein the intestinal epithelium comprises epithelial cells having a polarity in the tissue explant and the two or more drug transporters, wherein the tissue explant provides a luminal surface and a basolateral surface, and wherein the polarity of the epithelial cells is maintained in the tissue explant;
  (ii) contacting the tissue explant with two or more siRNA molecules for reducing or eliminating expression of the two or more drug transporters to generate a modified tissue explant, wherein the two or more drug transporters are reduced or eliminated individually or in combination, and wherein the siRNA molecules are formulated in a solution for ultrasound delivery;
  (iii) contacting the tissue explant of (i) or the modified tissue explant of (ii) with the candidate drug;
  (iv) determining adsorption of the candidate drug by detecting the presence of the drug at the luminal surface and at the basolateral surface, wherein presence of the drug at the basolateral surface indicates ability of the drug to be absorbed through the tissue explant; and
  (v) comparing absorption between the tissue explant, modified or unmodified, thereby investigating the known multiplex interactions between the candidate drug and two or more drug transporters. In some aspects, step (ii) comprises contacting the tissue with ultrasound to deliver the siRNA molecules.

In some aspects, the two or more drug transporters are efflux transporters, influx transporters, or a combination of both. In some aspects, the two or more drug transporters are present on the luminal surface of the intestinal tissue explant, the basolateral surface of the intestinal tissue explant, or both. In some aspects, efflux transporters present on the luminal surface of the intestinal tissue explant are selected from p-gp, BCRP and MRP2. In some aspects, efflux transporters present on the basolateral surface of the intestinal tissue explant comprise ABCC3. In some aspects, influx transporters present on the luminal surface of the intestinal tissue explant are selected from MCT1, SNAT2 and PEPT1. In some aspects, influx transporters present on the basolateral surface of the intestinal tissue explant comprises OCT1. In some aspects, the two or more drug transporters comprises a bi-directional transporter. In some aspects, the bi-directional transporter is OSTa/b. In some aspects, the two or more drug transporters is selected from any combination of: of p-gp, BCRP, MRP2, MCT1, SNAT2, PEPT1, ABCC3, OCT1, and OSTa/b. In some aspects, the two or more drug transporters comprise p-gp, BCRP and MRP2.

In some aspects, the method comprises a machine learning algorithm to determine the known multiplex interaction.

In other aspects, the disclosure provides a method for determining the effect of two or more drugs utilizing a drug transporter of interest on absorption of at least one of the drugs through an intestinal tissue explant, comprising:
  (i) obtaining an intestinal tissue explant comprising intestinal epithelium from a large, non-human, mammalian gastrointestinal tract, wherein the intestinal epithelium comprises epithelial cells having a polarity in the tissue explant and at least one intact drug transporter, wherein the tissue explant provides a luminal surface and a basolateral surface, and wherein the polarity of the epithelial cells is maintained in the tissue explant;
  (ii) contacting the tissue explant with a first drug known to interact with the drug transporter of interest and a second drug known to interact with the drug transporter of interest;
  (iii) determining adsorption of the first drug by detecting the presence of the drug at the luminal surface and at the basolateral surface, wherein the presence of the drug at the basolateral surface indicates absorption of the drug through the tissue explant; and (iv) comparing the absorption of the first drug in the presence and absence of the second drug, thereby determining the effect of two or more drugs utilizing the drug transporter of interest on absorption of the first drug through an intestinal tissue explant.

In some aspects, before (ii) the method comprises contacting the tissue explant with an agent the reduces or eliminates expression of the drug transporter of interest. In some aspects, the agent is an inhibitory RNA molecule. In some aspects, the inhibitory RNA molecule is an siRNA molecule. In some aspects, the agent is a small molecule that inhibits the drug transporter of interest. In some aspects, the agent is a gRNA molecule for use with a CRISPR/Cas system to eliminate the drug transporter of interest.

In some aspects, the drug transporter of interest is an efflux transporter. In some aspects, the efflux transporter is present on the luminal side of the tissue explant. In some aspects, the efflux transporter is selected from p-gp, BCRP and MRP2. In some aspects, the efflux transporter is present on the basolateral side of the tissue explant. In some aspects, the efflux transporter is ABCC3. In some aspects, the drug transporter of interest is an influx transporter. In some aspects, the influx transporter is present on the luminal side of the tissue explant. In some aspects, the influx transporter is selected from MCT1, SNAT2 and PEPT1. In some aspects, the influx transporter is present on the basolateral side of the tissue explant. In some aspects, the influx transporter is OCT1. In some aspects, the drug transporter of interest is a bi-directional transporter. In some aspects, the bi-directional transporter is OSTa/b.

In some aspects, the method comprises using a machine learning algorithm to identify the second drug known to interact with the drug transporter of interest. In some aspects, the machine learning algorithm provides information on possible transporter-substrate relationships.

In any of the foregoing or related aspects, the intestinal tissue explant is in planar contact with a substrate. In some aspects, the substrate comprises a plurality of microwells. In some aspects, the substrate comprises 6, 12, 24, 48, 96, 384 or 1536 microwells. In some aspects, each microwell is completely covered by the intestinal tissue explant. In some aspects, the substrate comprises a first plate comprising the plurality of microwells and a second plate, wherein the tissue explant is between the first and second plates. In some aspects, the second plate comprises a plurality of microwells. In some aspects, the plurality of microwells of the first plate are through holes, and wherein the plurality of microwells of the second plate are receiving chambers. In some aspects, the first and second plates apply pressure to the tissue explant to minimize well-to-well leakage.

In any of the foregoing or related aspects, the intestinal tissue explant:

(i) comprises small intestine epithelium, circular muscular layer and intestinal villi;

(ii) is derived from the ileum, jejunum, stomach, duodenum, esophagus, buccal, lingual or colon of the gastrointestinal tract of the gastrointestinal tract;

(iii) comprises fully intact extracellular matrix, optionally wherein the fully intact extracellular matrix comprises lamina propria and/or lamina muscularis;

(iv) forms a mucus layer in culture;

(v) does not require an exogenous growth factor to be maintained in culture, optionally wherein the exogenous growth factor is Wnt3a;

(vi) comprise intestinal enterocytes, optionally wherein intestinal enterocytes are identified by the presence of villin, e-cadherin, keratin 20, and/or fatty acid binding protein 1 (FABP1);

(vii) comprises tight junctions;

(viii) comprises mucin secreting goblet cells, optionally wherein mucin secreting goblet cells are identified by the presence of mucin 2 (Muc2) and/or caudal type homeobox 2 (CDX2);

(ix) comprises intestinal stem cells, optionally wherein intestinal stem cells are identified by the presence of leucine-rich repeat-containing G-protein coupled receptor 5 (LGR5) and/or olfactomedin 4 (OLFM4);

(x) comprises intestinal endocrine cells, optionally wherein intestinal endocrine cells are identified by the presence of glucagon-like peptide-1 (GLP-1), further optionally wherein intestinal endocrine cells are L cells;

(xi) comprises microfold cells, optionally wherein microfold cells are identified by the presence of vimentin;

(xii) comprises mucosubstances, optionally wherein the mucosubstances are glycoproteins, glycolipids or mucins;

(xiii) comprises neural cells, optionally wherein neural cells are identified by the presence of nestin;

(xiv) maintains a constant level of secreted Wnt3a;

(xv) comprises intact crypts; or (xvi) any combination of (i)-(xv).

In any of the foregoing or related aspects, the tissue explant is derived from a porcine gastrointestinal tract.

BRIEF DESCRIPTION OF FIGURES

FIG. 5A shows western-blots and FIG. 5B shows the relative expression level of each target after siRNA dosing calculated using the band density ratio compared to control on a single image taken from one gel without further processing using Image J. Multiple gels were prepared in parallel to arrive at replicates.

DETAILED DESCRIPTION

Figure 1:
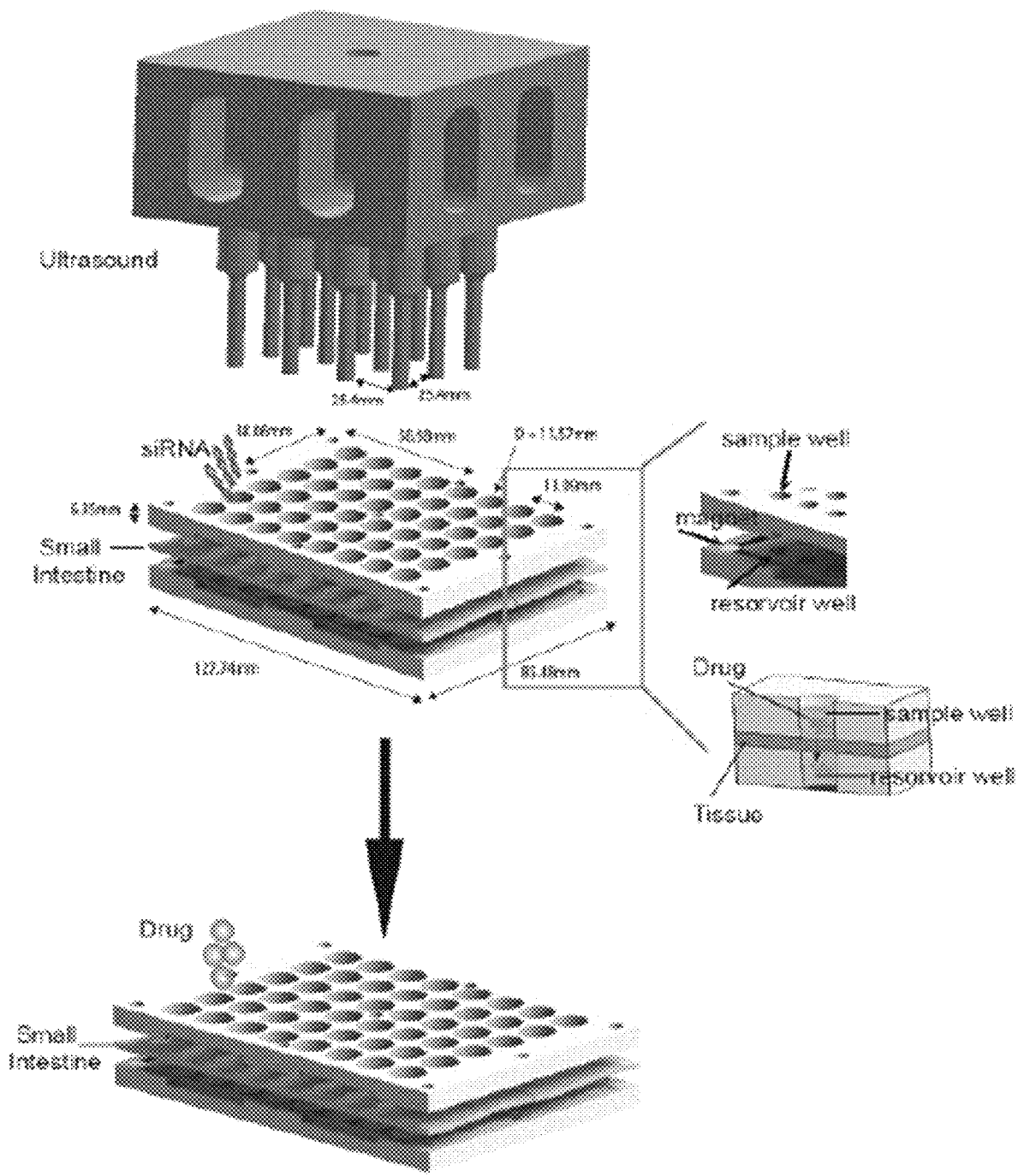
FIG. 1 is a schematic showing placement of an intestinal tissue explant between two magnetic plates, with the top plate having a sample through well and a bottom plate having a reservoir well. siRNA targeting a drug transporter is delivered via ultrasound and then the tissue explant is contacted with a drug of interest to analyze the impact of knocking-down the drug transporter on perfusion of the drug.

In some aspects, the present disclosure provides systems, kits and methods for investigating multiplex interactions between drugs and drug-transporters in an intestinal tissue explant. The systems, kits and methods of the present disclosure provide means to investigate interactions between a single drug candidate and more than one drug transporter, as well as interactions between two or more drugs that interact with the same drug transporter. Drug transporters are major determinants of the absorption, kinetics, and elimination of life saving therapeutics. Some drugs are substrates for multiple drug transporters, leading to complex transporter-drug interaction patterns that can drastically reduce bioavailability, increase the risk of drug resistance, and exponentially increase the number of drug-drug interactions.

The present disclosure is based, at least in part, on the discovery that multiplex drug interactions can be investigated by knocking down expression of two or more drug transporters in an intestinal tissue explant. As demonstrated herein, inhibitory RNA molecules (e.g., siRNA) targeting drug transporters expressed in porcine intestinal tissue were designed to efficiently knock down expression of two or more drug transporters and provide for investigation of drug interactions with the modified tissue. Without being bound by theory, the inhibitory RNA molecules described herein were designed to operate together, knocking down expression of two or more drug transporters simultaneously, thereby solving a problem often associated with such oligonucleotides which often interact with each other (e.g., dimerize), thus preventing their intended activity. As shown herein, the inhibitory RNA molecules reduced expression of p-gp, BCRP and MRP2 alone or in combination.

Based on the successful use of inhibitory RNA molecules to modulate expression of two or more drug transporters, the systems described herein were used to study substrates known to interact with two or more drug transporters. Specifically, a data set of substrates known to interact with p-gp, BCRP, MRP2, or any combination thereof, were analyzed and validated in the intestinal tissue explant described herein. As shown herein, reducing expression of a single drug transporter or multiple drug transporters simultaneously allows for the investigation of drug-drug transporter interactions. Accordingly, the present disclosure provides a platform that allows for determining the effects of multiple drug transporters on a single compound and characterizing the transportome. Further, it is presently shown that a machine learning model is useful to identify substrates of drug transporters, and interactions of such substrates with the intestinal tissue explant assayed as described herein.

The present disclosure is also based, at least in part, on the ability to examine interactions between multiple drugs utilizing the same drug transporter. Without being bound by theory, drugs that share at least one known transporter may impact transport kinetics for each drug in the human intestine which may have significant clinical impacts. As shown herein, the intestinal tissue explant is useful to validate known interactions between more than one drug. It was also shown that a machine learning model is useful to identify multiple drugs utilizing the same drug transporter, and such interactions assayed in the intestinal tissue explant. Specifically, interactions between doxycycline, a substrate for BCRP and MRP2, and other substrates for these transporters (warfarin, tacrolimus, digoxin and levetiracetam) were analyzed. It was found that all of the substrates tested, except warfarin, showed increased absorption upon co-treatment with doxycycline. Such interactions were not previously known, highlighting the importance of investigating drug-drug interactions. Accordingly, the disclosure provides systems, kits and methods which utilize an intestinal tissue explant as a platform to investigate drug-drug interactions and how these interactions impact intestinal absorption kinetics.

Further, the intestinal tissue explant described herein is suitable for high-throughput screening, allowing for efficient analysis of multiplex interactions.

It is believed using the intestinal tissue explant to investigate multiplex interactions is important for preclinical drug development and clinical decision making.

Investigating and Determining Multiplex Interactions

In some aspects, the disclosure provides methods and compositions for investigating or determining multiplex interactions between (i) a candidate drug and two or more drug transporters, and/or (ii) two drugs utilizing the same drug transporter. In some embodiments, such interactions are analyzed using an intestinal tissue explant described herein, wherein the intestinal tissue explant comprises at least one drug transporter.

Drug transportation is mediated by ATP-binding cassette (ABC) transporter and solute carrier (SLC) transporter families. These intestinal transporters are located in the brush border membrane as well as basolateral membrane. Each transporter exhibits its own substrate specificity, and some have broader specificities than others. In addition, the distribution and characteristics of the intestinal transporters exhibit regional differences along the intestine, implying diverse physiologic functions and in some cases pathologic responses. The International Transporter Consortium describe a limited number of transporters based on clinical evidence that they influence drug disposition and/or side effects (Nat Rev Drug Discov, 2010 March; 9(3): 215-236, herein incorporated by reference in its entirety).

In some embodiments, multiplex interactions of at least one drug transporter are determined using the compositions and methods described herein. In some embodiments, multiplex interactions of two or more drug transporters are determined using the compositions and methods described herein. In some embodiments, multiplex interactions between more than one drug transporter and more than one drug are determined using the compositions and methods described herein.

In some embodiments, the drug transporter is an efflux transporter. In some embodiments, an efflux transporter is located on the luminal surface of a tissue explant described herein. In some embodiments, the efflux transporter is p-glycoprotein (p-gp), breast cancer resistance protein (BCRP), or multidrug resistance-associated protein 2 (MRP-2). In some embodiments, an efflux transporter is located on the basolateral surface of a tissue explant described herein. In some embodiments, the efflux transporter is canalicular multispecific organic anion transporter 2 (ABCC3).

In some embodiments, the drug transporter is an influx transporter. In some embodiments, an influx transporter is located on the luminal surface of a tissue explant described herein. In some embodiments, the influx transporter is monocarboxylate transporter 1 (MCT1), sodium-dependent neutral amino acid transporter 2 (SNAT2) or peptide transporter 1 (PEPT1). In some embodiments, an influx transporter is located on the basolateral surface of a tissue explant described herein. In some embodiments, the influx transporter is organic cation transporter 1 (OCT1).

In some embodiments, the drug transporter is a bi-directional transporter. In some embodiments, the bi-directional transporter is organic solute transporter subunit alpha (OST-alpha).

In some embodiments, multiplex interactions between a candidate drug and two or more drug transporters is determined using an ex vivo system comprising (i) an intestinal tissue explant described herein, comprising two or more drug transporters; and (ii) two or more agents for use in reducing or eliminating the two or more drug transporters, wherein the intestinal tissue explant is contacted with the candidate drug before and after expression of the two or more drug transporters is reduced or eliminated in the intestinal tissue explant to determine multiplex interactions. In some embodiments, multiplex interactions are determined by contacting the intestinal tissue explant with the candidate drug before and after expression of a single drug transporter is reduced or eliminated individually, and then in combination with the two or more drug transporters. For example, in embodiments wherein the two or more drug transporters are p-gp, BCRP and MRP2, the intestinal tissue explant is contacted with the candidate drug before and after expression of (i) p-gp; (ii) BCRP; (iii) MRP2; (iv) p-gp and BCRP; (v) p-gp and MRP2; (vi) BCRP and MRP2; and (vii) p-gp, BCRP and MRP2, is reduced or eliminated in the tissue explant. Reducing or eliminating expression of the two or more drug transporters both individually and in combination/simultaneously allows for investigation of multiplex interactions.

In some embodiments, an expected or known interaction between a candidate drug and two or more drug transporters is validated using the ex vivo system described herein. In some embodiments, an expected or known interaction is determined based on what is known in the art. In some embodiments, an expected or known interaction is determined using machine learning models, as described herein.

In some embodiments, the disclosure provides a method for determining multiplex interactions between a candidate drug and two or more drug transporters, comprising:
 (i) obtaining an intestinal tissue explant comprising two or more drug transporters;
 (ii) contacting the tissue explant with agents for reducing or eliminating expression of the two or more drug transporters, individually and in combination, to generate a modified tissue explant;
 (iii) contacting the tissue explant of (i) and the modified tissue explant of (ii) with the candidate drug;
 (iv) determining absorption of the candidate drug; and
 (v) comparing absorption between the modified and unmodified tissue explant, thereby determining multiplex interactions between the candidate drugs and the two or more drug transporters.

In some embodiments, the disclosure provides a method for determining multiplex interactions between a candidate drug and two or more drug transporters, comprising:
 (i) obtaining an intestinal tissue explant comprising two or more drug transporters selected from the group: p-gp, BCRP, MRP2, MCT1, and PEPT1;
 (ii) contacting the tissue explant with agents for reducing or eliminating expression of the two or more drug transporters, individually and in combination, to generate a modified tissue explant;
 (iii) contacting the tissue explant of (i) and the modified tissue explant of (ii) with the candidate drug;

(iv) determining absorption of the candidate drug; and
(v) comparing absorption between the modified and unmodified tissue explant, thereby determining multiplex interactions between the candidate drugs and the two or more drug transporters.

In some embodiments, the disclosure provides a method for determining multiplex interactions between a candidate drug and two or more drug transporters, comprising:
(i) obtaining an intestinal tissue explant comprising (a) p-gp and BCRP; (b) p-gp and MRP2; (c) BCRP and MRP2; or (d) p-gp, BCRP and MRP2;
(ii) contacting the tissue explant with agents for reducing or eliminating expression of the two or more drug transporters selected from (a)-(d), individually and in combination, to generate a modified tissue explant;
(iii) contacting the tissue explant of (i) and the modified tissue explant of (ii) with the candidate drug;
(iv) determining absorption of the candidate drug; and
(v) comparing absorption between the modified and unmodified tissue explant, thereby determining multiplex interactions between the candidate drugs and the two or more drug transporters.

In some embodiments, the disclosure provides a method for determining multiplex interactions between a candidate drug and two or more drug transporters, comprising:
(i) obtaining an intestinal tissue explant comprising (a) p-gp and BCRP; (b) p-gp and MRP2; (c) BCRP and MRP2; or (d) p-gp, BCRP and MRP2;
(ii) contacting the tissue explant with agents for reducing or eliminating expression of the two or more drug transporters selected from (a)-(d), individually and in combination, to generate a modified tissue explant, wherein the agents are:
  (a) a p-gp targeting siRNA molecule comprising a sense strand comprising the nucleotide sequence set forth in SEQ ID NO: 91 and an antisense strand comprising the nucleotide sequence set forth in SEQ ID NO: 92;
  (b) a MRP2 targeting siRNA molecule comprising a sense strand comprising the nucleotide sequence set forth in SEQ ID NO: 93 and an antisense strand comprising the nucleotide sequence set forth in SEQ ID NO: 94; and
  (c) a BCRP targeting siRNA molecule comprising a sense strand comprising the nucleotide sequence set forth in SEQ ID NO: 95 and an antisense strand comprising the nucleotide sequence set forth in SEQ ID NO: 96;
(iii) contacting the tissue explant of (i) and the modified tissue explant of (ii) with the candidate drug;
(iv) determining absorption of the candidate drug; and
(v) comparing absorption between the modified and unmodified tissue explant, thereby determining multiplex interactions between the candidate drugs and the two or more drug transporters.

In some aspects, the disclosure provides a method for determining the effect of two or more drugs utilizing a drug transporter of interest on absorption of at least one of the drugs through an intestinal tissue explant, comprising:
(i) obtaining an intestinal tissue explant comprising the drug transporter of interest;
(ii) contacting the tissue explant with a first drug known to interact with the drug transporter of interest and a second drug known to interact with the drug transporter of interest;
(iii) determining adsorption of the first drug; and
(iv) comparing the absorption of the first drug in the presence and absence of the second drug,
thereby determining the effect of two or more drugs utilizing the drug transporter of interest on absorption of the first drug through an intestinal tissue explant.

In some aspects, the disclosure provides a method for determining the effect of two or more drugs utilizing a drug transporter of interest on absorption of at least one of the drugs through an intestinal tissue explant, comprising:
(i) obtaining an intestinal tissue explant comprising the drug transporter of interest;
(ii) contacting the tissue explant with an agent that reduces or eliminates expression of the drug transporter of interest to generate a modified tissue explant;
(iii) contacting the tissue explant of (i) and the modified tissue explant of (ii) with a first drug known to interact with the drug transporter of interest and a second drug known to interact with the drug transporter of interest;
(iii) determining adsorption of the first drug; and
(iv) comparing the absorption of the first drug in the presence and absence of the second drug in the unmodified and modified tissue explant,
thereby determining the effect of two or more drugs utilizing the drug transporter of interest on absorption of the first drug through an intestinal tissue explant.

A. Modulating Expression of Drug Transporters

In some embodiments, expression of at least one drug transporter is reduced or eliminated in an intestinal tissue explant to determine the multiplex interactions between drugs and drug transporters. In some embodiments, expression of two or more drug transporters is reduced or eliminated in an intestinal tissue explant to determine the multiplex interactions between drugs and drug transporters.

In some embodiments, expression of any of the following drug transporters is reduced or eliminated, individually or simultaneously, in an intestinal tissue explant: p-gp, BCRP, MRP2, ABCC3, MCT1, SNAT2, PEPT1, OCT1, or any combination thereof. In some embodiments, expression of p-gp, BCRP, MRP2, MCT1 and PEPT1 is reduced or eliminated in an intestinal tissue explant, individually or simultaneously. In some embodiments, expression of p-gp, BCRP and MRP2 is reduced or eliminated in an intestinal tissue explant, individually or simultaneously. In some embodiments, expression of p-gp, BCRP and MRP2 is reduced or eliminated in an intestinal tissue explant, individually and simultaneously.

In some embodiments, expression of a drug transporter is reduced or eliminated temporarily (e.g., temporary knockdown). In some embodiments, expression of a drug transporter is reduced or eliminated permanently.

In some embodiments, expression of a drug transporter is reduced or eliminated with inhibitory RNA molecules. In some embodiments, inhibitory RNA molecules utilize the RNA interference (RNAi) pathway. RNAi is a biological process of inhibiting or down regulating gene expression in a cell mediated by short interfering nucleic acid molecules (siNA molecule). The terms "inhibitory RNA molecule" and "siNA molecule" are used interchangeably herein. In some embodiments, an siNA molecule is a single-stranded or double-stranded nucleic acid molecule capable of inhibiting the expression of a target gene when transfected into or expressed within a host mammalian cell or tissue.

The inhibiting activity of a siNA molecule is achieved by mediating RNAi or gene silencing in a sequence-specific manner, including but not limited to Argonaute-mediated post-transcriptional cleavage of mRNA transcripts of the target gene. In some embodiments, the siNA molecule comprises a nucleotide sequence of about 15 to about 30 nucleotides that is substantially complementary to a sequence in the target gene. In some embodiments, the target gene is present in one or more of the coding region, the promoter region, the 3' untranslated region and the 5' untranslated region. siNA molecules useful in inhibiting a target gene include, but are not limited to, siRNA, short hairpin RNA (shRNA), double-stranded RNA (dsRNA), micro-RNA (miRNA), and circular RNA molecules. A single stranded siNA molecule may have one or more double-stranded regions and a double-stranded siNA molecule may have one or more single-stranded regions.

In some embodiments, the siNA molecule is a double-stranded nucleic acid molecule comprising self-complementary sense and antisense strands, wherein the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. In some embodiments, the siNA molecule is a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region comprises a nucleotide sequence corresponding to the target nucleic acid sequence or a portion thereof.

In some embodiments, the siNA molecule is a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region comprises a nucleotide sequence corresponding to the target nucleic acid sequence or a portion thereof, and wherein the circular polynucleotide can be processed either in vivo or in vitro to generate an active siNA molecule capable of mediating RNAi.

In some embodiments, an inhibitory RNA molecule used in the present disclosure is selected from the group:
(i) a p-gp targeting inhibitory RNA molecule comprising a sense strand comprising the nucleotide sequence set forth in SEQ ID NO: 91 and an antisense strand comprising the nucleotide sequence set forth in SEQ ID NO: 92;
(ii) a MRP2 targeting inhibitory RNA molecule comprising a sense strand comprising the nucleotide sequence set forth in SEQ ID NO: 93 and an antisense strand comprising the nucleotide sequence set forth in SEQ ID NO: 94;
(iii) a BCRP targeting inhibitory RNA molecule comprising a sense strand comprising the nucleotide sequence set forth in SEQ ID NO: 95 and an antisense strand comprising the nucleotide sequence set forth in SEQ ID NO: 96;
(iv) a SNAT2 targeting inhibitory RNA molecule comprising a sense strand comprising the nucleotide sequence set forth in SEQ ID NO: 97 and an antisense strand comprising the nucleotide sequence set forth in SEQ ID NO: 98;
(v) a PEPT1 targeting inhibitory RNA molecule comprising a sense strand comprising the nucleotide sequence set forth in SEQ ID NO: 99 and an antisense strand comprising the nucleotide sequence set forth in SEQ ID NO: 100;
(vi) a MCT1 targeting inhibitory RNA molecule comprising a sense strand comprising the nucleotide sequence set forth in SEQ ID NO: 101 and an antisense strand comprising the nucleotide sequence set forth in SEQ ID NO: 102;
(vii) an ABCC3 targeting inhibitory RNA molecule comprising a sense strand comprising the nucleotide sequence set forth in SEQ ID NO: 103 and an antisense strand comprising the nucleotide sequence set forth in SEQ ID NO: 104;
(viii) an OST-alpha targeting inhibitory RNA molecule comprising a sense strand comprising the nucleotide sequence set forth in SEQ ID NO: 105 and an antisense strand comprising the nucleotide sequence set forth in SEQ ID NO: 106; and
(ix) an OCT targeting inhibitory RNA molecule comprising a sense strand comprising the nucleotide sequence set forth in SEQ ID NO: 103 and an antisense strand comprising the nucleotide sequence set forth in SEQ ID NO: 104.

In some embodiments, an inhibitory RNA molecule used in the present disclosure is selected from the group:
(i) a p-gp targeting inhibitory RNA molecule comprising a sense strand comprising the nucleotide sequence set forth in SEQ ID NO: 91 and an antisense strand comprising the nucleotide sequence set forth in SEQ ID NO: 92;
(ii) a MRP2 targeting inhibitory RNA molecule comprising a sense strand comprising the nucleotide sequence set forth in SEQ ID NO: 93 and an antisense strand comprising the nucleotide sequence set forth in SEQ ID NO: 94;
(iii) a BCRP targeting inhibitory RNA molecule comprising a sense strand comprising the nucleotide sequence set forth in SEQ ID NO: 95 and an antisense strand comprising the nucleotide sequence set forth in SEQ ID NO: 96;
(iv) a PEPT1 targeting inhibitory RNA molecule comprising a sense strand comprising the nucleotide sequence set forth in SEQ ID NO: 99 and an antisense strand comprising the nucleotide sequence set forth in SEQ ID NO: 100; and
(v) a MCT1 targeting inhibitory RNA molecule comprising a sense strand comprising the nucleotide sequence set forth in SEQ ID NO: 101 and an antisense strand comprising the nucleotide sequence set forth in SEQ ID NO: 102.

In some embodiments, an inhibitory RNA molecule used in the present disclosure is:
(i) a p-gp targeting inhibitory RNA molecule comprising a sense strand comprising the nucleotide sequence set forth in SEQ ID NO: 91 and an antisense strand comprising the nucleotide sequence set forth in SEQ ID NO: 92;
(ii) a MRP2 targeting inhibitory RNA molecule comprising a sense strand comprising the nucleotide sequence set forth in SEQ ID NO: 93 and an antisense strand comprising the nucleotide sequence set forth in SEQ ID NO: 94; and
(iii) a BCRP targeting inhibitory RNA molecule comprising a sense strand comprising the nucleotide sequence set forth in SEQ ID NO: 95 and an antisense strand comprising the nucleotide sequence set forth in SEQ ID NO: 96.

In some embodiments, an inhibitory RNA molecule used in the present disclosure is selected from the group:
  (i) a p-gp targeting siRNA molecule comprising a sense strand comprising the nucleotide sequence set forth in SEQ ID NO: 91 and an antisense strand comprising the nucleotide sequence set forth in SEQ ID NO: 92;
  (ii) a MRP2 targeting siRNA molecule comprising a sense strand comprising the nucleotide sequence set forth in SEQ ID NO: 93 and an antisense strand comprising the nucleotide sequence set forth in SEQ ID NO: 94;
  (iii) a BCRP targeting siRNA molecule comprising a sense strand comprising the nucleotide sequence set forth in SEQ ID NO: 95 and an antisense strand comprising the nucleotide sequence set forth in SEQ ID NO: 96;
  (iv) a SNAT2 targeting siRNA molecule comprising a sense strand comprising the nucleotide sequence set forth in SEQ ID NO: 97 and an antisense strand comprising the nucleotide sequence set forth in SEQ ID NO: 98;
  (v) a PEPT1 targeting siRNA molecule comprising a sense strand comprising the nucleotide sequence set forth in SEQ ID NO: 99 and an antisense strand comprising the nucleotide sequence set forth in SEQ ID NO: 100;
  (vi) a MCT1 targeting siRNA molecule comprising a sense strand comprising the nucleotide sequence set forth in SEQ ID NO: 101 and an antisense strand comprising the nucleotide sequence set forth in SEQ ID NO: 102;
  (vii) an ABCC3 targeting siRNA molecule comprising a sense strand comprising the nucleotide sequence set forth in SEQ ID NO: 103 and an antisense strand comprising the nucleotide sequence set forth in SEQ ID NO: 104;
  (viii) an OST-alpha targeting siRNA molecule comprising a sense strand comprising the nucleotide sequence set forth in SEQ ID NO: 105 and an antisense strand comprising the nucleotide sequence set forth in SEQ ID NO: 106; and
  (ix) an OCT targeting siRNA molecule comprising a sense strand comprising the nucleotide sequence set forth in SEQ ID NO: 103 and an antisense strand comprising the nucleotide sequence set forth in SEQ ID NO: 104.

In some embodiments, an inhibitory RNA molecule used in the present disclosure is selected from the group:
  (i) a p-gp targeting siRNA molecule comprising a sense strand comprising the nucleotide sequence set forth in SEQ ID NO: 91 and an antisense strand comprising the nucleotide sequence set forth in SEQ ID NO: 92;
  (ii) a MRP2 targeting siRNA molecule comprising a sense strand comprising the nucleotide sequence set forth in SEQ ID NO: 93 and an antisense strand comprising the nucleotide sequence set forth in SEQ ID NO: 94;
  (iii) a BCRP targeting siRNA molecule comprising a sense strand comprising the nucleotide sequence set forth in SEQ ID NO: 95 and an antisense strand comprising the nucleotide sequence set forth in SEQ ID NO: 96;
  (iv) a PEPT1 targeting siRNA molecule comprising a sense strand comprising the nucleotide sequence set forth in SEQ ID NO: 99 and an antisense strand comprising the nucleotide sequence set forth in SEQ ID NO: 100; and
  (v) a MCT1 targeting siRNA molecule comprising a sense strand comprising the nucleotide sequence set forth in SEQ ID NO: 101 and an antisense strand comprising the nucleotide sequence set forth in SEQ ID NO: 102.

In some embodiments, an inhibitory RNA molecule used in the present disclosure is:
  (i) a p-gp targeting siRNA molecule comprising a sense strand comprising the nucleotide sequence set forth in SEQ ID NO: 91 and an antisense strand comprising the nucleotide sequence set forth in SEQ ID NO: 92;
  (ii) a MRP2 targeting siRNA molecule comprising a sense strand comprising the nucleotide sequence set forth in SEQ ID NO: 93 and an antisense strand comprising the nucleotide sequence set forth in SEQ ID NO: 94; and
  (iii) a BCRP targeting siRNA molecule comprising a sense strand comprising the nucleotide sequence set forth in SEQ ID NO: 95 and an antisense strand comprising the nucleotide sequence set forth in SEQ ID NO: 96.

In some embodiments, any of the siRNA molecules are formulated in a solution for ultrasound delivery to the intestinal tissue explant. Methods for formulation siRNA for ultrasound delivery are described in at least (Schoellhammer, C. M., et al. Gastroenterology, Vol. 152: 1151-1160 (2017); Schoellhammer, C. M. & Traverso, G., Expert Opin Drug Deliv, Vol. 13: 1045-1048 (2016), each of which is herein incorporated entirely by this reference).

In some embodiments, expression of a drug transporter is reduced or eliminated using a gRNA targeting a gene encoding the drug transporter, for use in a CRISPR/Cas system. Methods for identifying gRNAs that deliver a Cas endonuclease to a gene of interest are known to those of skill in the art.

In some embodiments, expression or activity of a drug transporter is reduced or eliminated using a small molecule. In some embodiments, a small molecule inhibits a drug transporter described herein. In some embodiments, a p-gp inhibitor is selected from to colchicine, irinotecan, loperamicine, nicardipine and ranitidine. In some embodiments, a BCRP inhibitor is selected from 4-methylumelliferone sulfate, daunorubicin, mitoxantrone, pitavastatin, and rosuvastatin. In some embodiments, a MRP2 inhibitor is selected from etoposide, irinotecan, olmesartan, para-aminohippurate, and valsartsn. In some embodiments, a MCT1 inhibitor is selected from paraquat, ganciclovir, and acyclovir. In some embodiments, a PEPT1 inhibitor is selected from amoxicillin, cefadroxil, enalapril, valacyclovir, and cephalexin.

Methods for determining whether expression of a protein has been reduced or eliminated are known to those of skill in the art. Methods include, but are not limited to, RT-PCR, Q-PCR, western-blotting, ELISA, and FACS.

B. Machine Learning Algorithm to Identify Drug-Drug and Drug-Transporter Interactions In some embodiments, the methods and compositions provided herein comprise a machine learning algorithm to identify drug-drug and/or drug-transporter interactions.

In some embodiments, a machine learning algorithm is generated by curating a training dataset mined from known databases. In some embodiments, the databases are DrugBank 5.0, Metrabase, and NIH screen NCI-60. In some embodiments, a random forest machine learning model is used to predict the substrate relationships within a dataset based on chemical and physiochemical features of the substrates and non-substrates.

In some embodiments, a machine learning algorithm is used to determine an interaction between a candidate drug and drug transporter. In some embodiments, the machine learning algorithm identifies whether a candidate drug is a substrate of a drug transporter. In some embodiments, a machine learning algorithm determines whether a candidate drug interacts with a group of drug transporters. In some embodiments, the machine learning algorithm identified unknown drug-drug transporter interactions not previously reported.

In some embodiments, the machine learning algorithm provides information on likely transporter-substrate relationships. In some embodiments, the machine learning algorithm predicts transporter-substrate relationships.

In some embodiments, the machine learning algorithm classified investigational drugs into categories of substrates for individual drug transporters or combinations of drug transporters.

In some embodiments, a machine learning algorithm identifies drug-drug transporter interaction(s) which can then be validated using any of the systems, methods and compositions described herein.

C. Analyzing Drug Absorption in the Intestinal Tissue Explant

In some aspects of the disclosure, absorption of a compound or drug of interest in the intestinal tissue explant is determined to investigate multiplex interactions between drugs and drug transporters. In some embodiments, absorption is determined before and/or after modulation of a drug transporter within the intestinal tissue explant.

The small intestine is an important site for the absorption of pharmacological agents. The proximal part of the small intestine has the greatest capacity for absorption of drugs. The current standard for predicting drug absorption is the CaCo-2 monolayer model. However, there are many defects in this model system. The CaCo-2 model lacks the intestinal mucus layer, metabolic enzymes, and extracellular matrix, along with the architecture and various cell types found in vivo. Moreover, CaCo-2 cells are heterogeneous human epithelial colorectal adenocarcinoma cells, which by their nature are very different compared to primary cells with regard to cell behavior (e.g., protein/gene expression, continuous cell division, and cell-cell adhesion complexes). Other systems have been developed to overcome the defects in the CaCo-2 system and are described (Dedhia, P., et al. Gastroenterology 2016; Vol. 150: 1098-1112; Ranga, A., et al. Advanced Drug Delivery Reviews 69-70 2014; 19-28; Shamir, E. and Ewald, A., Nature Reviews: Molecular Cell Biology 2014; Vol. 15: 647-664, Ootani, A., et al. Nature Medicine 2009 June; Vol. 15(6): 701-706).

However, these systems still fail to fully recapitulate the complex in vivo architecture and function of the gastrointestinal tract (e.g., small intestine). The tissue explant described herein provides significant advantages over the current model systems. For example, the tissue explant described herein maintains the in vivo architecture of the gastrointestinal tract (e.g., small intestine) from which it was derived. In addition, the tissue explant comprises the components necessary for drug absorption (e.g., drug metabolizing enzymes, drug transporters). The tissue explant described herein can also be maintained in culture for long periods of time, unlike previously developed systems. Further, the tissue explant described herein does not require exogenous factors for maintenance in culture. Moreover, as discussed infra, the tissue explant described herein can be used for high-throughput screening. These characteristics highlight the improvements over prior model systems.

The tissue explant described herein provides a model system for testing and predicting drug absorption of a compound of interest to investigate multiplex interactions between drugs and drug transporters.

In some aspects of the disclosure, drug absorption is predicted by determining the perfusion of a compound of interest through the tissue explant. Specifically, a compound of interest is added to the tissue explant followed by detection of the compound at both the basolateral and luminal surfaces of the tissue. Presence of the compound at the basolateral surface indicates the ability of the compound to perfuse through the tissue explant, thereby predicting drug absorption and oral bioavailability. A person of ordinary skill in the art can readily determine the concentration of a compound using a variety of methods, for example, spectrophotometric analysis, high performance liquid chromatography with spectrophotometric detection or liquid chromatography-mass spectrometry. In some embodiments, the candidate agent is radiolabeled, allowing for detection in the receiver chamber and within the tissue.

High-Throughput Screening

In some aspects of the disclosure, methods and culture systems are provided for investigating multiplex interactions in a high-throughput format. By "high-throughput" or "HT", it is meant the screening of large numbers of drug-drug transporter or drug-drug interactions simultaneously for an activity of interest. In some embodiments, expression of drug transporters is modulated in a high-throughput format by applying candidate agents that reduce or eliminate expression of at least one drug transporter. By large numbers, it is meant screening 20 or more candidates at a time, e.g. 40 or more candidates, e.g. 100 or more candidates, 200 or more candidates, 500 or more candidates, or 1000 candidates or more.

In some embodiments, the high throughput screen will be formatted based upon the numbers of wells of the tissue culture plates used, e.g. a 24-well format, in which 24 candidate agents (or less, plus controls) are assayed; a 48-well format, in which 48 candidate agents (or less, plus controls) are assayed; a 96-well format, in which 96 candidate agents (or less, plus controls) are assayed; a 384-well format, in which 384 candidate agents (or less, plus controls) are assayed; a 1536-well format, in which 1536 candidate agents (or less, plus controls) are assayed; or a 3456-well format, in which 3456 candidate agents (or less, plus controls) are assayed.

In some embodiments, the disclosure provides methods for high-throughput screening for analyzing absorption of candidate drugs through a modified or unmodified intestinal tissue explant. In some embodiments, the tissue explant is contacted with a substrate, wherein the substrate comprises a plurality of microwells, wherein the tissue explant is contacted with agents for reducing or eliminating expression of at least one drug transporter followed by contact with a candidate drug(s), wherein absorption of the candidate drug is determined, and wherein results of absorption are compared to identify multiplex interactions between drugs and drug transporters.

Drug Transporter Substrates

In some embodiments, the drug transporter of a candidate drug is determined, and optionally substrates for the same drug transporter are identified, to investigate drug-drug interactions and/or drug-drug transporter interactions. Drug transporter substrates are biologically active agents that encompass numerous chemical classes, organic molecules, which trmy include organometallic molecules, inorganic molecules, genetic sequences, etc, One aspect of the disclosure is to evaluate the absorption of candidate drugs and identify drug-drug or drug-drug transporter interactions.

Drug transporter substrates comprise functional groups necessary for structural interaction with proteins, particularly hydrogen bonding, and typically include at least an amine, carbonyl, hydroxyl or carboxyl group, frequently at least two of the functional chemical groups. The substrates often comprise cyclical carbon or heterocyclic structures and/or aromatic or polyaromatic structures substituted with one or more of the above functional groups. Drug transporter substrates are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. In some embodiments, drug transporter substrates include chemotherapeutic agents, anti-inflammatory agents, hormones or hormone antagonists, ion channel modifiers, and neuroactive agents.

Drug transporter substrates, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. In some embodiments, a library of drug transporter substrates comprises approved and/or experimental drugs. In some embodiments, the library comprises approved and/or experimental drugs conjugated to biologically active or inactive molecules. In some embodiments, a drug transporter substrate library is commercially available.

The tissue explant described herein is useful for investigating multiplex interactions of a variety of agent types. In some embodiments, candidate agents are small molecules (e.g., doxycycline). In some embodiments, candidate agents are small molecule drugs. In some embodiments, candidate agents are biologics, including peptide drugs (e.g., oxytocin) and protean drugs (e.g., insulin). In some embodiments, candidate agents are antisense oligonucleotides.

In some embodiments, candidate agents are known drugs classified by the FDA's Biopharmaceutics Classification System (BCS), which takes into account three major factors that govern the rate and extent of drug absorption from immediate release (IR) solid oral dosage forms: dissolution, solubility and intestinal permeability. BCS Class I refers to high solubility and high permeability. BCS Class II refers to low solubility and high permeability. BCS Class II refers to high solubility and low permeability. BCS Class IV refers to low solubility and low permeability.

Kits

In some aspects, the disclosure provides a kit comprising at least a tissue explant described herein and agents for reducing or eliminating expression of at least one drug transporter. In some embodiments, the kit comprises a substrate for the tissue explant. The kits may comprise, in a suitable container, a tissue explant described herein, and optionally a substrate, and various buffers, reagents, enzymes and other standard ingredients well known in the art.

In some aspects, the disclosure provides a kit comprising an ex vivo system described herein for use in determining multiplex interactions between a candidate drug and two or more drug transporters. In some embodiments, the kit comprises (i) an intestinal tissue explant comprising two or more drug transporters, (ii) two or more agents for use in reducing or eliminating expression of the two or more drug transporters; and (iii) instructions for use of the system to determine multiplex interactions between the candidate drug and the two or more drug transporters, wherein the instructions comprise contacting the intestinal tissue explant with the candidate drug before and after expression of the two or more drug transporters is reduced or eliminated in the intestinal tissue explant. In some embodiments, the instructions comprising contacting the intestinal tissue explant with the candidate drug before and after expression of the two or more drug transporters is reduced or eliminated individually and in combination/simultaneously.

In some aspects, the disclosure provides a kit comprising (i) an intestinal tissue explant comprising two or more drug transporters selected from the group: p-gp, BCRP and MRP2; (ii) two or more siRNA molecules selected from the group: (a) a p-gp targeting siRNA molecule comprising a sense strand comprising the nucleotide sequence set forth in SEQ ID NO: 91 and an antisense strand comprising the nucleotide sequence set forth in SEQ ID NO: 92; (b) a MRP2 targeting siRNA molecule comprising a sense strand comprising the nucleotide sequence set forth in SEQ ID NO: 93 and an antisense strand comprising the nucleotide sequence set forth in SEQ ID NO: 94; and (c) a BCRP targeting siRNA molecule comprising a sense strand comprising the nucleotide sequence set forth in SEQ ID NO: 95 and an antisense strand comprising the nucleotide sequence set forth in SEQ ID NO: 96; and (iii) instructions for contacting the intestinal tissue explant with a candidate drug before and after expression of the two or more drug transporters is reduced or eliminated in the intestinal tissue explant, individually and in combination, using the siRNA molecules.

In some embodiments, the kit comprises a tissue explant described herein and a substrate comprising plates for interfacing with the tissue explant and cover films to seal one of the plates, wherein the substrate is compatible with a robotic arm. Such containers may include injection or blow-molded plastic containers into which the desired components are retained. Containers and/or kits can include labeling with instructions for use and/or warnings.

Tissue Explant

Tissue explants described herein are useful in the method described herein as they provide features of in vivo tissue from which they are derived. Features include, without limitation, prolonged tissue expansion with proliferation, multilineage differentiation, and recapitulation of cellular and tissue architecture, including epithelial tissues, submucosal tissues, and stromal environments.

In some embodiments, tissue explants for use in the disclosure include, but are not limited to, tissues from the stomach, small intestine, duodenum, esophagus, buccal, colon or tongue.

A. Method for Obtaining Tissue Explant

The tissue explant described herein provides for culture, maintenance of in vivo architecture and recapitulation of tissue function, for example, long term or prolonged culture, maintenance of in vivo architecture and recapitulation of tissue function and use in methods described herein. The tissue explants described herein are useful for analysis of the tissue of interest (e.g., small intestine) and high-throughput screening assays.

In some embodiments, the tissue explant described herein is derived from either a human or a large, non-human mammal. In some embodiments, the large, non-human mammal, includes ungulates (i.e., hoofed mammals such as pigs, cows, goats, sheep, horses, donkeys, deer, antelopes and the like) and more generally, livestock (i.e., mammals raised for agricultural purposes such as pigs, cows, goats, sheep, horses, rabbits, and the link, and/or as beasts of burden such as donkeys, horses, elephants, camels, llamas, and the like). In some embodiments, the large, non-human mammal is a pig.

In some embodiments, the tissue of interest (e.g., small intestine) is obtained surgically. In some embodiments, the tissue of interest (e.g., small intestine) is obtained surgically post-exsanguination (i.e., draining of blood). In some embodiments, the tissue explant obtained is the length and width of the substrate of interest. In some embodiments, the tissue explant obtained is the length and width of a standard 6, 12, 24, 48, 96, 384, 1536 or 3456 well plate. In some embodiments, the tissue explant obtained is the length and half the width of a standard 6, 12, 24, 48, 96, 384, 1536 or 3456 well plate. In some embodiments, the tissue explant is about 127.8 mm in length and about 42.75 mm in width. In some embodiments, the tissue explant is about 127.8 mm in length and 85.5 mm in width.

In some embodiments, the age of the animal can have an effect on the maintenance and function of the tissue explant. In some embodiments, the animal is between 3 weeks and 12 weeks of age. In some embodiments the animal is 3 weeks of age. In some embodiments the animal is 12 weeks of age. In some embodiments the animal is 1, 2, 3, 4, 5, 6, 7, 8, 9, 10, 11, 12, 13, 14 or 15 weeks of age. In some embodiments, the animal is 1, 2, 3, 4, 5, 6 or 7 months old. In some embodiments, fetal tissue is utilized.

In some embodiments, the tissue explant is immersed in a series of saline solutions after dissection. In some embodiments, the tissue explant is immersed in 70% ethanol after dissection, followed by washing with saline solutions. In some embodiments, the saline solutions are supplemented with an antibiotic solution. In some embodiments, the saline solutions are supplemented with an antimycotic solution. In some embodiments, the saline solutions are supplemented with an antibiotic and antimycotic solution. Antibiotic and antimycotic solutions are known by those of skill in the art. For example, Gibco® Antibiotic-Antimycotic solution is useful in the methods described herein. In some embodiments, the antibiotic and/or antimycotic solution comprises penicillin, streptomycin, Gibco® amphotericin B, or combinations thereof.

In some embodiments, the tissue explant is immersed in a known preservation solution. Examples of preservation solutions include, but are not limited to, Krebs-Henseleit solution, UW solution, St. Thomas II solution, Collins solution, and Stanford solution (See, for example, U.S. Pat. Nos. 4,798,824 and 4,938,961; Southard and Belier, Ann. Rev. Med. 46:235-247 (1995); and Donnelly and Djuric. Am. J. Hosp. Pharma. 48:2444-2460 (1991)). The solution may contain one or more of sodium, potassium, calcium, magnesium, glutamate, arginine, adenosine, mannitol, allopurinol, glutathione, raffinose, and lactobionic acid. In some embodiments, the solution is maintained at physiological pH of about 7.2-7.4.

In some embodiments, the tissue is kept on ice before dissection. Therefore, in some embodiments the solutions are 4° C. before being used.

The tissue explant is subsequently mounted on the substrate of interest (e.g., multi-well plate) and cultured in culture media at 37° C. in an airtight container. In some embodiments, the culture media is free of serum. In some embodiments, the culture media comprises serum.

In some embodiments, the culture media does not contain exogenous growth factors (e.g., Wnt3a). In some embodiments, the tissue explant does not require exogenous growth factors due to the presence of the stromal layer. In some embodiments, the culture media is Dulbecco's Modified Eagle Medium (DMEM) or Advanced DMEM/F-12. In some embodiments, the culture media includes fetal bovine serum (FBS). In some embodiments, the culture media include EGF Recombinant Human Protein. In some embodiments, the presence of FBS and/or EGF does not affect the viability of the tissue explant.

In some embodiments, the tissue explant is derived from the gastrointestinal tract of a human or large, non-human mammal. The gastrointestinal tract comprises the mouth, esophagus, stomach and or rumen, intestines (small and large), cecum (plural ceca), fermentation sacs, and the anus. In some embodiments, the tissue explant is derived from the intestine. In some embodiments, the tissue explant is derived from the small intestine.

The roughly 8 meters of intestine in the adult human plays numerous roles in physiologic homeostasis including absorptive, secretory and immune functions. Commensurate with these essential roles, diseases of the intestine are a considerable source of human morbidity and mortality. Indeed, numerous pathologic conditions including cancer, inflammatory bowel diseases, mesenteric ischemia, congenital syndromes and trauma, with or without concomitant intestinal resection, result in "short-gut" syndromes resulting in severe deficiencies of physiologic intestinal function and effective intestinal failure.

The intestine is an organ with tremendous regenerative potential, whereby stem cells resident in proliferative crypt regions give rise to progenitors capable of multilineage differentiation. The intestinal stem cells (ISCs) are able to repopulate epithelium of the entire 8-meter length of the adult human intestine every 5-7 days, helping to maintain the integrity of the mucosal barrier and effecting tissue repair upon injury. It has been postulated that the ISC niche has complex architectural requirements whereby myofibroblasts enveloping the proliferative crypt provide essential signals to crypt stem and/or progenitor cells.

The small intestine has three distinct regions, the duodenum, jejunum and ileum. The duodenum is connected to the distal end of the stomach and receives bile and pancreatic juice through the pancreatic duct. The jejunum and ileum primarily absorb nutrients and water more so than the breaking down of food.

In some embodiments, the tissue explant is derived from the jejunum of the small intestine. In some embodiments, the tissue explant is derived from the ileum of the small intestine. In some embodiments, the tissue explant is derived from the duodenum of the small intestine.

B. Composition of Tissue Explant

Tissue

Intestine

Like other parts of the gastrointestinal tract, the small intestine is comprised of four basic layers: the mucosa, submucosa, muscularis externa, and serosa. It is the body's major digestive organ, the site where digestion is completed and almost all absorption occurs. The small intestine is highly adapted for nutrient absorption. Both its long length and the modifications of its inner surface provide an extraordinary large surface area and enhance absorption enormously.

The outermost layer of the intestine, the serosa, is a smooth membrane consisting of a thin layer of cells that secrete serous fluid, and a thin layer of connective tissue. The muscularis externa, adjacent to the submucosa membrane, comprises two muscle layers of an inner circular and outer longitudinal smooth muscle. It is responsible for gut movement (i.e., peristalsis). The submucosa is a layer of dense irregular connective tissue or loose connective tissue that supports the mucosa and joins it to the underlying smooth muscle. The innermost layer and lining of the small intestine is the mucosa. It is a mucous membrane that secretes digestive enzymes and hormones. The mucosa comprises intestinal villi, an epithelium and a lamina propria. The lamina propria is a thin layer of loose connective tissue, or dense irregular connective tissue, which lies beneath the epithelium and together with the epithelium constitutes the mucosa.

In some embodiments, the tissue explant described herein comprises the serosa, muscularis externa, submucosa and mucosa. In some embodiments, the tissue explant described herein comprises the muscularis externa, submucosa and mucosa. In some embodiments, the tissue explant described herein comprises the inner circular smooth muscle, the submucosa, and the mucosa. Methods for identifying these structures include visual inspection, by, for example, histological staining (e.g., haemotoxylin & eosin stain) followed by microscopic analysis. Using such methods, one of skill in the art can identify the various structures of the tissue explant.

In some embodiments, the tissue explant described herein comprises a fully intact extracellular matrix. In some embodiments, the extracellular matrix comprises the lamina propria. In some embodiments, the extracellular matrix comprises the lamina muscularis.

In some embodiments, the tissue explant described herein maintains polarity (e.g., epithelial cell polarity) as described herein. In some embodiments, the tissue explant described herein is in a planar position, thereby providing a luminal surface and a basolateral surface. In some embodiments, either surface is accessible. Methods of determining polarity are known to those of skill in the art. A review of such methods can be found in Chapter 7 of Cell Polarity and Morphogenesis (Academic Press, 2017, herein incorporated by reference in its entirety). In some embodiments, polarity of the tissue explant described herein is analyzed by visual (e.g., microscopic) inspection. For example, since the tissue explant described herein comprises two or more genetically distinct cell populations, polarity can be determined by expression of a labeled protein in only a subset of cells and subsequently visualized by microscopic techniques. In some embodiments, immunohistochemistry and live images of fluorescent reports are used to visualize proteins in their tissue context and evaluate their distribution. In some embodiments, cell polarization is quantified by analyzing protein localization in fluorescent images and calculating the ratio of fluorescence intensity between regions where the protein is present and regions where it is weakly localized or absent. The fluorescence ratio provides a quantitative measure of asymmetric protein distribution. See Marcinkevicius, E., et al. *J. Biol.* 2009, Vol. 8(12): 103, herein incorporated by reference in its entirety. In some embodiments, the fluorescence ratio is normalized by choosing appropriate analysis settings and incorporating internal controls, as described by Shimoni, R., et al. *PLoS ONE* 2014, Vol. 9(6): e99885, herein incorporated by reference in its entirety.

In some embodiments, the tissue explant described herein maintains the in vivo architecture of the intestinal tissue from which it is derived. In some embodiments, the in vivo architecture is determined by visual inspection by methods known to those of skill in the art and described infra. For example, in some embodiments, determination of the maintenance of the in vivo architecture comprises comparing freshly excised tissue with tissue explants cultured ex vivo over time.

The intestinal villi, fingerlike extensions of the inner mucosal surface, are one of the primary specializations characteristic of the intestine's absorption and digestion functions. The epithelial cells that comprise the villi are chiefly absorptive cells or enterocytes. Their capacity to secrete, absorb, and digest specific ions and nutrients, depends on their position along the length of the intestine. The enterocytes, themselves, have microvilli, giving the mucosal surface a fuzzy appearance sometimes called the "brush border." The microvilli comprise enzymes which aid in digestion, such as disaccharidases and peptidases. In some embodiments, the tissue explant described herein comprises enterocytes. In some embodiments, enterocytes are identified by the presence of villin, e-cadherin, keratin 20, and/or fatty acid binding protein 1 (FABP1). In some embodiments, the tissue explant described herein comprises villi.

The intestinal mucus layer plays an important protective role. The mucus layer is primarily comprised of mucins. Mucins are highly glycosylated large glycoproteins with protein backbone structures rich in serine and threonine, which are linked to a wide variety of O-linked oligosaccharide side chains that make up more than 70% of the weight of the molecule. Up to 20 different mucin genes have been identified, MUC1 to MUC20 according to order of their discovery. Mucin genes are expressed in tissue and cell type-specific manner and are broadly classified into two types, secretory and membrane-associated. In small and large intestine, MUC2 is the major secretory mucin synthesized and secreted by goblet cells. Intestinal mucus layers secreted by goblet cells consist mainly of compact mesh-like network of viscous, permeable, gel-forming MUC2 mucin, which provides the frontline host defense against endogenous and exogenous irritants and microbial attachment and invasion but allows the transport of nutrients. In some embodiments, the tissue explant comprises mucin secreting goblet cells. In some embodiments, the tissue explant forms a mucus layer in culture. In some embodiments, the tissue explant described herein comprises mucosubstances. In some embodiments, the mucosubstances are glycoproteins, glycolipds or mucins.

Mucin 2 (Muc 2) as well as Caudal type homeobox 2 (CDX2) are both markers for the mucin secreting goblet cells within the intestinal epithelium. In some embodiments, goblet cells are identified by the presence of Mucin 2 (Muc 2) and/or Caudal type homeobox 2 (CDX2).

In some embodiments, presence of a mucus layer in the tissue explant described herein is determined by measuring the presence of mucins and/or mucosubstances. In some embodiments, the presence of a mucus layer in the tissue explant described herein is determined by measuring the gene expression of Muc 2 and/or CDX2. In some embodiments, the presence of a mucus layer in the tissue explant described herein is determined by measuring the protein expression of Muc 2 and/or CDX2. In some embodiments, the presence of a mucus layer in the tissue explant described herein is determined by visual inspection (e.g., microscopy). In some embodiments, histological staining, such as with alcian blue tissue stain, is used for visual inspection.

Between the villi, the mucosa is studded with pits or openings which lead into tubular intestinal glands called intestinal crypts or crypts of Lieberkuhn. The epithelial cells which line the crypts secrete intestinal juice, a fluid mixture comprising mucus. Deep in the crypts are Paneth cells which produce various polypeptides, such as cryptdin, lysozyme, type II (secretory) phospholipase A2, intestinal defensin (e.g., RIP-3). In some embodiments, the tissue explant described herein comprises intact crypts. In some embodiments, intact crypts are identified by visual inspection (e.g., microscopy). Methods of visual inspection for identifying intact crypts include, but are not limited to, histological tissue staining and normal light microscopy.

The gastrointestinal tract is characterized by self-renewing epithelium fueled by adult stem cells residing at the bottom of the intestinal crypt and gastric glands. In the adult intestine, cellular division only occurs in the crypt, not in the villus. Several potential stem cell populations have been proposed in the crypt. One of them, named crypt based columnar (CBC) cells is closely associated with Paneth cells at crypt bottoms. CBCs along with Paneth cells have long been proposed to form a restricted stem cell zone within the crypt, which has been confirmed by lineage tracing experiments. Such lineage tracing experiments have revealed that single Lgr5+(leucine-rich repeat-containing G-protein coupled receptor 5) CBC cells are able to regenerate an entire crypt-villus axis. These cells are in a state of "stemness" and possess long-term self-renewal capabilities as well as multipotent differentiation abilities. In some embodiments, the tissue explant described herein comprises intestinal stem cells. In some embodiments, the intestinal stem cells are Lgr5+. In some embodiments, the presence of intestinal stem cells in the tissue explant described herein is responsible for long-term maintenance of the explant.

In addition to Lgr5+, olfactomedin-4 (OLFM4) emerged as a robust marker for intestinal stem cells based on a gene signature of Lrg5 stem cells. Therefore, in some embodiments, the tissue explant described herein comprises OLFM4+ stem cells. In some embodiments, the tissue explant described herein comprises Lrg5+ and OLFM4+ stem cells. In some embodiments, Lrg5+ and OLFM4 stem cells are detected by methods known to those of skill in the art and further described herein.

Several signaling mechanisms are also involved in maintaining the renewal capacity of the small intestine. Wnt, BMP/TGF-β, Notch and EGF are key regulators of epithelial homeostasis and self-renewal activity. While the cells move across the crypt-villus axis they are exposed to a Wnt gradient. Stem cells become loaded with Wnt mediators that are produced by adjacent Paneth cells, which bind to their cognate Frizzled receptors. Due to their local production and limited diffusion, Wnt molecules as well as their receptors are diminished through turnover by cellular division as the cells leave the stem cell zone and move away from Paneth cells. Besides Lgr5+, the CBC stem cells express a whole set of further Wnt pathway associated genes, which directly controls stemness in the intestinal crypts. The high Wnt activity in CBC stem cells is mediated by binding of secreted R-spondin family members to Lgr family members on the CBC membrane. This binding potentiates the Frizzled mediated Wnt pathway activation and results in robust activation of the Wnt pathway. Moreover, myofibroblasts play a role in maintaining the renewal capacity of the small intestine by providing signaling cues. Specifically, myofibroblasts, which surround the intestinal crypt, secrete factors such as Wnt ligands, HGF, BMP and Noggin, important in regulating differentiation (see Medema, J. and Vermeulen, L., *Nature*, Vol. 474: 318-326, 2011, herein incorporated by reference).

Prior intestinal model systems, including primary intestinal epithelial cells and/or intestinal stem cells, require exogenous addition of Wnt to maintain the systems. The tissue explants described herein do not require exogenous Wnt for culture maintenance. The presence of intact crypts and villi, along with stroma, contribute to this feature of the tissue explants described herein.

In some embodiments, the tissue explant described herein comprises intestinal endocrine cells. Intestinal endocrine cells, or enteroendocrine cells, are restricted to the mucosa and located within the intestinal crypts and villi (Moran, G., et al. Therap Adv Gastroenterol. 2008 July; Vol. 1(1): 51-60, herein incorporated by reference in its entirety). Enteroendocrine cells found in the small intestine include, but are not limited to, cholecystokinin-secreting cells, secretin-secreting S cells, gastric inhibitory polypeptide-secreting cells, motilin-secreting M cells and neurotensin secreting N cells, and neuroendocrine L cells. In some embodiments, the tissue explant described herein comprise L cells. Enteroendocrine cells are characterized by the presence of secretary vesicles. Enteroendocrine cells secrete glucagon-like peptide-1 (GLP-1). In some embodiments, secretion of GLP-1 is in response to the presence of glucose. In some embodiments, secretion of GLP-1 is in response to the presence of acetylcholine. In some embodiments, secretion of GLP-1 is in response to the presence of LiCl. In some embodiments, secretion of GLP-1 is determined by the concentration of GLP-1 7-36. In some embodiments, the tissue explant described herein is responsive to glucose, acetylcholine and/or LiCl due to the presence of enteroendocrine cells.

In some embodiments, the tissue explant described herein comprises tight junctions. In some embodiments, tight junctions are identified by the presence of claudin-1, e-cadherin, or a combination thereof, determined by methods known to those of skill in the art and further described herein. Claudin-1 is an integral membrane protein and e-cadherin is a transmembrane protein, both of which are components of tight junctions. Tight junctions represent one mode of cell-to-cell adhesion in epithelial or endothelial cell sheets, forming continuous seals around cells and serving as a physical barrier to prevent solutes and water from passing freely.

The submucosa contains individual and aggregated lymphoid patches, the latter called Peyer's patches. In the duodenum only, mucus-secreting duodenal glands (also called Brunner's glands) are found. Microfold (M) cells are found in Peyer's patches of the intestine and are specialized for the phagocytosis and transcytosis of gut lumen macromolecules. These cells play an important role in the induction of specific mucosal immune responses in the Peyer's patches, and allow for transport of microbes and particles across the epithelial cell layer from the gut lumen to the lamina propria where interactions with immune cells can take place. In some embodiments, the tissue explant described herein comprises microfold cells. Microfold cells are identified by cytoskeletal and extracellular matrix components expressed at the edge of the cells or on their cell surfaces, including actin, villin, cytokeratin and vimentin. In some embodiments, microfold cells are identified by the presence of vimentin, actin, cytokeratin, villin, or combination thereof. In some embodiments, microfold cells are identified by the presence of vimentin. In some embodiments, microfold cells are identified by the presence of actin. In some embodiments, microfold cells are identified by the presence of villin. In some embodiments, microfold cells are identified by the presence of cytokeratin.

The enteric nervous system (ENS) is the intrinsic nervous system of the gastrointestinal tract. It contains complete reflex circuits that detect the physiological condition of the gastrointestinal tract, integrate information about the state of the gastrointestinal tract, and provide outputs to control gut movement, fluid exchange between the gut and its lumen, and local blood flow. The ENS works in concert with the central nervous system (CNS) to control the digestive system in the context of local and whole body physiological demands.

The ENS originates from neural crest cells. These cells proliferate and differentiate into neurons and glial cells, and form two concentric plexuses of ganglion cells localized in the muscle layers of the gut wall (Furness, J. B. (2006). The organisation of the autonomic nervous system: peripheral connections. Auton. Neurosci. 130, 1-5. doi:10.1016/j.autneu.2006.05.003). In some embodiments, the tissue explant described herein comprises neural cells. In some embodiments, neural cells are identified by the presence of nestin. Nestin is an intermediate filament protein that is a known neural stem/progenitor cell marker.

Colon

In some embodiments, the tissue explant is derived from the colon. The colon is a part of the digestive system that functions in the absorption of water, electrolytes, and nutrients that remain after passing through the small intestine, and also in the compaction of feces. The lining of the colon, and its innermost layer, is the mucosa. The tunica serosa is the outermost covering of the digestive tube. It is comprised of an irregular dense connective tissue surrounded by a mesothelium, a type of squamous epithelium. Underneath the tunica serosa is the muscularis externa, comprising two muscle layers of an inner circular and outer longitudinal muscle. Between the layers are nervous plexus (Auberbach's myenteric). A fibroelastic connective tissue is found at the next level. Called the submucosa, it contains submucosal (Meissner) nervous plexuses, pre- and post-ganglionic parasympathetic fibers, and nonmyelinated preganglionic fibers from the vagus nerve. The innermost layer and lining of the colon is the mucosa. It comprises of an epithelium, a lamina propria, and muscularis mucosae. The epithelium is a simple columnar absorptive epithelium. The lamina propria is a loose connective tissue beneath the epithelium, and the muscularis mucosae is a thin smooth muscle cell layer surrounding the mucosa. The mucosa contains glands or crypts. The crypts comprise goblet cells and regenerative cells or enterocytes. The lamina propria (LP) fills the spaces between the crypts. The crypts are filled with large numbers of goblet cells that secrete mucus to lubricate ejection of the feces.

In some embodiments, the tissue explant described herein retains the in vivo architecture of the colon tissue from which it is derived. For example, in some embodiments, the issue explain comprises the epithelium and lamina propria of the colon. In some embodiments the tissue explant comprises the epithelium, lamina propria and muscularis mucosae of the colon. In some embodiments, the tissue explant further comprises the inner circular muscle from the muscularis externa of the colon. In some embodiments, the tissue explain comprises the inner circular and longitudinal muscle of the muscularis externa. In some embodiments, the tissue explain further comprises the submucosa of the colon. In some embodiments, the tissue explant further comprises intact crypts found in the colon. In some embodiments, the tissue explant derived from the colon comprises a mucus layer. In some embodiments, the tissue explant derived from the colon comprises a mucus layer and bowel content present on the apical side of the colon. In some embodiments, a tissue explant derived from the colon comprising a mucus layer and bowel content present on the apical side of the colon is useful for microbiome studies.

Stomach

In some embodiments, the tissue explant is derived from stomach, or gastric, tissue. The stomach is a muscular, hollow, dilated part of the alimentary canal. It comprises a mucosal layer comprising mucosal epithelium and lamina propria; which is surrounded by a submucosal layer comprising loose connective tissue; which is surrounded by a muscularis layer comprising several thick layers of muscle. The mucosal epithelium is comprised of four major types of secretory epithelial cells: mucous cells, which secrete an alkaline mucus that protects the epithelium against shear stress and acid; parietal cells, which secrete hydrochloric acid; chief cells (also called "peptic cells") which secrete the zymogen pepsinogen; and G cells, which secrete the hormone gastrin. Cells within the mucosal epithelium can be identified by methods known to those of skill in the art. The epithelium is folded into thousands of tiny pits, called gastric pits, at the base of which are gastric glands; the mucous cells reside at the neck of the pits, while the chief cells and parietal cells residue at the base of the pits, in the glandular zone. Other markers of terminal gastric epithelial differentiation include H+/K+atpase and mucin (MUC5A).

Stomach tissue also comprises a stomach-specific stem cell, a villin$^+$Lgr5$^+$ cell which is able to give rise to all gastric cell lineages. Current molecular markers for gastric progenitor cells and gastric cancer stem cells are described in J. Gastroenterol. 2011 July; 46(7):855-65, the disclosure of which is incorporated herein by reference.

In some embodiments, the tissue explain: described herein retains the in vivo architecture of the stomach tissue from which it is derived. For example, in some embodiments, the tissue explant comprises the mucosal epithelium and lamina propria from the stomach. In some embodiments, the tissue explant further comprises the muscularis layer from the stomach. In some embodiments, the tissue explant derived from the stomach comprises mucous cells, parietal cells, chief cells, G cells, or combinations thereof. In some embodiments, the tissue explant derived from the stomach comprises villin+Lgr5+ stem cells.

Esophagus

In some embodiments, the tissue explant is derived from the esophagus. The esophagus is a muscular tube connecting the throat (pharynx) with the stomach. The esophagus is about 8 inches long and lined with mucosa. The upper esophageal sphincter (UES) is a bundle of muscles at the top of the esophagus which is under conscious control. The lower esophageal sphincter (LES) is a bundle of muscles at the low end of the esophagus, where it meets the stomach, and is not under voluntary control. When closed, the LES prevents acid and stomach contents from traveling backwards.

The esophagus consists of mucosa, submucosa, layers of muscle fibers between layers of fibrous tissue, and an outer layer of connective tissue (serosa). The mucosa (innermost layer) is a stratified squamous epithelium of approximately three layers of squamous cells, which contrasts the single layer of columnar cells of the stomach. At the base of the mucosa lies the muscularis mucosa. The epithelial layer, connective tissue and muscularis mucosa comprise the mucosa.

In some embodiments, the tissue explain: described herein retains the in vivo architecture of the esophageal tissue from which it is derived. For example, in some embodiments, the tissue explant comprises the mucosa of the esophagus. In some embodiments, the tissue explant comprises the mucosa and muscularis mucosa of the esophagus. In some embodiments, the tissue explant derived from the esophagus further comprises the serosa.

Buccal and Lingual

In some embodiments, the tissue explant is derived from buccal tissue (oral mucosa; relating to the mouth or cheek). In some embodiments, the tissue explant is derived from lingual tissue (relating to the tongue).

Buccal tissue consists of two layers, the surface stratified squamous epithelium and the deeper lamina propria. The epithelium consists of the following four layers: stratum basale, stratum spinosum, stratum granulosum, and stratum corneum. Depending on the region of the mouth, the epithelium may be keratinized or nonkeratinized. Nonkeratinized squamous epithelium covers the soft palate, inner lips, inner cheeks and floor of the mouth. Keratinized squamous epithelium is present in the attached gingiva and hard palate.

In some embodiments, the tissue explant retains the in vivo architecture of the buccal tissue from which it is derived. For example, in some embodiments, the tissue explant comprises the surface stratified squamous epithelium of the buccal tissue. In some embodiments, the tissue explain comprises the stratum basale, stratum spinosum, stratum granulosum, stratum corneum, or combinations thereof. In some embodiments, the tissue explant comprises the surface stratified squamous epithelium and the lamina propria of the buccal tissue. In some embodiments, the tissue explant derived from the buccal tissue comprises keratinized epithelium. In some embodiments, the tissue explant derived from the buccal tissue comprises nonkeratinized epithelium.

The tongue is a muscular organ in the mouth covered in mucosa. It is a mass of interlacing skeletal muscle, connective tissue with some mucous and serous glands, and pockets of adipose tissue. The tongue is anchored to the mouth via webs of tough tissue and mucosa. The tether holding down the front of the tongue is called the frenum. In the back of the mouth, the tongue is anchored into the hyoid hone. The tongue consists of lingual papillae, which are the small structure on the upper surface of the tongue. Four types of papillae are found on the tongue: circumvallate papillae, fungiform papillae, filiform papillae and foliate papillae. All except the filiform papillae are associated with taste buds.

In some embodiments, the tissue explant described herein retains the in vivo architecture of the lingual tissue from which it is derived. For example, in some embodiments, the tissue explant comprises the connective tissue of the lingual tissue. In some embodiments, the tissue explain comprises mucous and serous glands present in the lingual tissue. In some embodiments, the tissue explant derived from the lingual tissue comprises intact lingual papillae. In some embodiments, the tissue explant derived from the lingual tissue comprises circumvallate fungiform papillae, filiform papillae, foliate papillae, or combinations thereof.

Culture and Activity of Tissue Explant

In some embodiments, the tissue explant described herein retains the functional characteristics of the tissue from which it is derived.

Drug transporters often work together with drug-metabolizing enzymes (DMEs) in drug absorption and eliminations. Drug metabolism has a significant effect on drug efficacy and toxicity. Drug metabolic reactions are categorized as Phase I, which functionalize the drug molecule and prepare it for further metabolism, and Phase II, which are conjugative. In general, Phase I reaction products are partially or fully inactive. However, Phase I reaction products are sometimes more active than the originally administered drug. The major classes of Phase I enzymes include, but are not limited to, cytochrome P450 and flavin-containing monooxygenase. The major classes of Phase II enzymes include, but are not limited to, UDP glucuronyltransferase, sulfotransferase, glutathione S-transferase, N-acyltransferase, and N-acetyl transferase. Therefore, in some embodiments, the tissue explant described herein comprises at least one drug-metabolizing enzyme. In some embodiments, the at least one drug-metabolizing enzyme is a Phase I enzyme. In some embodiments, the at least one drug metabolizing enzyme is CYP3A4. CYP3A4 is an isoform of cytochrome P450. In some embodiments, the at least one drug-metabolizing enzyme is a Phase II enzyme. In some embodiments, the at least one drug metabolizing enzyme is uridine 5'-diphospho glucuronosyltransferase (UGT). UGT is a drug metabolizing enzyme expressed in the intestine that catalyzes glucuronidation, wherein it adds a glucuronic acid moiety to drugs or other substances, thereby triggering their elimination via the kidneys. In some embodiments, the at least one drug metabolizing enzyme is sulfotransferase, N-acetyltransferase, S-methyltransferase, thiopurine methyltransferase, glutathione s-transferase, or glucuronyltransferase.

In some embodiments, the tissue explant described herein retains thioredoxin reductase activity. Thioredoxin reductase is a ubiquitous enzyme involved in many cellular processes such as cell growth, and protection against oxidation stress. Thioredoxin plays a crucial role in a wide number of physiological processes, which span from reduction of nucleotides to deoxyriboucleotides to the detoxification from xenobiotics, oxidants and radicals. The redox function of thioredoxin is critically dependent on thioredoxin reductase. The thioredoxin system includes thioredoxin, thioredoxin reductase and NADPH. Thioredoxins serve as electron donors for enzymes such as ribonucleotide reductases, thioredoxin peroxidases, and methionine sulfoxide reductases. Many transcription factors require thioredoxin reduction for DNA binding.

In some embodiments, thioredoxin reductase activity of the tissue explant is determined using methods known to one of skill in the art. In some embodiments, thioredoxin reductase activity of the tissue explant is determined using a commercially available kit (e.g., Thioredoxin Reductase Activity Assay Kit, Ray Biotech).

In some embodiments, the tissue explant described herein retains protease activity. Proteases represent up to 2% of the human genome, with 500-600 different proteases identified. Proteases specifically cleave proteins at their extremities (N-terminal or C-terminal regions) and are referred to as exopeptidases, or in the middle of the proteins, and are referred to as endopeptidases. Depending on the mechanism, human proteases are classified as serine, threonine, cysteine, aspartic or metalloproteases. Some proteases are secreted and released in the extracellular milieu, while others have intracellular functions and exclusively remain inside cells. Proteases are heavily present in the gastrointestinal tract, both in the lumen and deeply into the tissues. Pancreatic proteases (tyrpsins, chymotrypsin, elastase, etc.) are released into the lumen of the upper gastrointestinal tract, where they exert digestive functions. The microbiota constitutes an important source of proteases.

In some embodiments, protease activity of the tissue explant is determined using methods known to one of skill in the art. For example, protease activity of the tissue explant can be determined using a commercially available kit (e.g., Protease Activity Assay Kit, RayBiotech).

In some embodiments, the tissue explant described herein is responsive to toxins. In some embodiments, the tissue explant described herein is responsive to substances with gastrointestinal toxicity. In some embodiments, the tissue explant described herein is responsive to substances with cellular toxicity. In some embodiments, the toxin is a non-steroidal anti-inflammatory drug (NSAID), a bronchodilator, a bisphosphonate, an antibiotic, an antiviral, a vasodilator or a diuretic. In some embodiments, the NSAID is naproxen, mesalamine, ketoprofen, indomethacin or meloxicam. In some embodiments, the bronchodilator is theophylline. In some embodiments, the bisphosphonate is etidronate. In some embodiments, the antibiotic is doxycycline or cefpodoxime. In some embodiments, the antiviral is oseltamivir or tenofovir. In some embodiments, the vasodilator is tadalafil. In some embodiments, the diuretic is amiloride. In some embodiments, the toxin is doxycycline.

In some embodiments, toxicity is assayed by determining viability of the tissue explant described herein. For example, a toxic substance may reduce viability of the tissue explant. Assays for viability include, but are not limited to, Live/Dead assays which stain the cells and allow for subsequent microscopic analysis. In some embodiments, FACS analysis is used to analyze viability (e.g., Live/Dead staining). In some embodiments, toxicity is assayed by determining the difference in cell culture maintenance of the tissue explant described herein. For example, a toxic substance may reduce the time in which the tissue explant can be maintained in culture. In some embodiments, toxicity is assayed by determining the difference in architecture of the tissue explant described herein. For example, a toxic substance may alter the architecture in a way that it no longer mimics the in vivo tissue from which the tissue explant was derived. In some embodiments, toxicity is assayed by analyzing metabolic activity. In some embodiments, metabolic activity is measured via alamarBlue® staining. In some embodiments, toxicity is measured by analyzing release of cellular compounds into medium. In some embodiments, release of cellular compounds is measured via adenylate kinase. In some embodiments, toxicity is measured by analyzing necrosis and/or apoptosis markers. In some embodiments, apoptosis markers include, but are not limited to, cleaved caspase3, cleaved lamin A and pHistone H2A. A person of ordinary skill in the art can readily determine induction of apoptosis using a variety of methods, for example, caspase activation assays (e.g., caspase-3/7 activation assays), stains and dyes (e.g., CELLTOX™, MITOTRACKER® Red, propidium iodide, and YOYO3), cell viability assays, cell morphology, and PARP-1 cleavage. In some embodiments, staining of cells with necrosis and/or apoptosis markers is analyzed via FACS. In some embodiments, toxicity is measured using a TUNEL assay.

In some embodiments, the tissue explant described herein recovers from exposure to a toxin. As used herein, the terms "recovery" and "recovers" refer to an increase in viability and/or a decrease in toxicity as measured by the methods described herein, such as by alamarBlue® assay. In some embodiments, recovery occurs over 1 day, 2 days, 3 days, 4 days, 5 days, 6 days or at least 7 days after initial exposure to a toxin.

In some embodiments, the tissue explant described herein is maintained in culture. A tissue explant is considered to be maintained in culture if it is viable. In some embodiments, the tissue explant is maintained in culture for 2, 4, 6, 8, 10 or 12 hours in culture. In some embodiments, the tissue explant is maintained in culture for 24 hours. In some embodiments, the tissue explant is maintained in culture for at least 2 days. In some embodiments, the tissue explant is maintained in culture for at least 3 days. In some embodiments, the tissue explant is maintained in culture for at least 4 days. In some embodiments, the tissue explant is maintained in culture for 1 week. In some embodiments, the tissue explant is maintained in culture for at least 1 week. In some embodiments, the tissue explant is maintained in culture for 2 weeks. In some embodiments, the tissue explant is maintained in culture for at least 2 weeks. In some embodiments, the tissue explant is maintained in culture for 3 weeks. In some embodiments, the tissue explant is maintained in culture for 4 weeks. In some embodiments, the tissue explant is maintained in culture for 5 weeks. In some embodiments, the tissue explant is maintained in culture for 6 weeks. In some embodiments, the tissue explant is maintained in culture for 7 weeks. In some embodiments, the tissue explant is maintained in culture for 8 weeks. In some embodiments, the tissue explant is maintained in culture for 9 weeks. In some embodiments, the tissue explant is maintained in culture for 10 weeks. In some embodiments, the tissue explant is maintained in culture for 11 weeks. In some embodiments, the tissue explant is maintained in culture for 12 weeks. In some embodiments, the tissue explant is maintained in culture for 13 weeks. In some embodiments, the tissue explant is maintained in culture for 14 weeks. In some embodiments, the tissue explant is maintained in culture for 15 weeks. In some embodiments, the tissue explant is maintained in culture for 16 weeks. In some embodiments, the tissue explant is maintained in culture for 17 weeks. In some embodiments, the tissue explant is maintained in culture for 18 weeks. In some embodiments, the tissue explant is maintained in culture for 18 weeks or more.

Analysis of Tissue Explant

As described supra, the tissues within the gastrointestinal tract comprise distinguishing features and cell types. In some embodiments, the architecture of the tissue explant is maintained in culture. In some embodiments, architecture is analyzed via microscopic evaluation. In some embodiments, electron microscopy is used to analyze architecture of the tissue explant. Electron microscopy includes, but is not limited to, transmission electron microscopy (TEM), scanning electron microscopy (SEM) and focused ion beam (FIB) microscopy. In some embodiments, the architecture of the tissue explant is evaluated by staining the tissue explant and observing it microscopically. Methods for staining tissue are known by those of skill in the art, and include, but are not limited to immunohistochemistry assays, immunofluoresence assays, and in situ hybridization assays. In some embodiments, the tissue explant is stained with hematoxylin and eosin (H&E). In some embodiments, the tissue explant is stained with Masson's Trichrome. Masson's Trichrome stains connective tissue, nuclei and cytoplasm. In some embodiments, the tissue explant is stained with Alcian blue. Alcian blue stains acid mucosubstances and acetic mucins.

Methods for identifying specific cell types are also known to one of skill in the art. For example, staining with an antibody which recognizes a specific marker of the cell type, or using a probe such as DNA/RNA for in situ hybridization. Immunohistochemical staining of the tissue explant is used to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide or against a synthetic peptide based on the DNA sequences encoding the polypeptide or against an exogenous sequence fused to a DNA encoding a polypeptide and encoding a specific antibody epitope.

Further, expression of proteins within the tissue explant can be determined. Assays for protein expression include, but are not limited to, ELISA (enzyme linked immunosorbent assay), SPR assays, immunoprecipitation assay, affinity chromatography, Western blots, RIA, "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In some embodiments, the tissue explant is freshly isolated. In some embodiments, the tissue explant is frozen. In some embodiments, the tissue explant is formalin-fixed paraffin-embedded. In some embodiments, the tissue explant is lysed.

C. Modification of Tissue Explant

In some embodiments, the tissue explant is modified prior, or during the culture period. In some embodiments, the tissue explant is modified by exposure to viral or bacterial pathogens. In some embodiments, the tissue explant is modified by altering patterns of gene expression (e.g., by providing reprogramming factors). In some embodiments, the tissue explant is modified through genetic modification. In some embodiments, genetic modification includes, but is not limited to knocking down genes with, for example, interfering RNAs (shRNA, siRNA), and stable genetic modification with, for example, CRISPR/Cas9.

In some embodiments, the tissue explant is modified to generate a pathological condition. Examples of pathological conditions include, but are not limited to, inflammatory bowel diseases (IBD), colon cancer, mesenteric ischemia, congenital syndromes and trauma, which can produce functional loss or mandate physical resection of large sections of intestine extensive enough to compromise organ physiology. The ability to maintain tissue explants in culture is valuable for development of therapies for treating intestinal diseases and trauma induced intestinal failure.

Methods for modifying cells or tissue are known to one of skill in the art. For example, introduction of an expression vector encoding a polypeptide can be used to express the encoded product in cells lacking the sequence, or to overexpress the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; siRNA or a shRNA, encode a dominant negative mutation, or dominant or constitutively active mutations of native sequences; altered regulatory sequences, etc. Instead of being expressed from a vector transfected or transduced into the tissue explant, the oligonucleotides, siRNA or shRNA can be directly transfected or transduced into the tissue explain.

In addition to sequences derived from the host cell species, other sequences of interest include, for example, genetic sequences of pathogens, for example coding regions of viral, bacterial and protozoan genes, particularly where the genes affect the function of human or other host cells. Sequences from other species may also be introduced, where there may or may not be a corresponding homologous sequence.

A large number of public resources are available as a source of genetic sequences, e.g. for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) Nature 402, 489-495; or Deloukas et al. (1998) Science 282, 744-746.

cDNA clones corresponding to many human gene sequences are available from the IMAGE consortium. The international IMAGE Consortium laboratories develop and array cDNA clones for worldwide use. The clones are commercially available, for example from Genome Systems, Inc., St, Louis, Mo. Methods for cloning sequences by PCR based on DNA sequence information are also known in the art.

Methods that are well known to those skilled n the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques, January 2000, p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In some embodiments, methods are used that achieve a high efficiency of transfection, and therefore circumvent the need for using selectable markers. These may include physical modes of delivery including microneedles, microjets, iontophoresis, and ultrasound mediated siRNA delivery.

Substrates for the Tissue Explant

In some embodiments, the tissue explant described herein is placed on a substrate. Various culture substrates can be used in the methods and systems of the disclosure. Such substrates include, but are not limited to, glass, polystyrene, polypropylene, stainless steel, silicon and the like. In some embodiments, the substrate is poly(methyl methacrylate). In some embodiments, the substrate is a polycarbonate, acrylic copolymer, polyurethane, aluminum, carbon or Teflon (polytetrafluoroethylene). The cell culture surface can be chosen from any number of rigid or elastic supports. For example, cell culture material can comprise glass or polymer microscope slides. In some embodiments, the substrate may be selected based upon a tissue's propensity to bind to the substrate. In some embodiments, the substrate may be selected based on the potential effect of the substrate on the tissue explant (e.g., electrical stimulation/resistivity, mechanical stimulation/stress).

The cell culture surface/substrate can be made of any material suitable for culturing mammalian cells. For example, the substrate can be a material that can be easily sterilized such as plastic or other artificial polymer material, so long as the material is biocompatible. In some embodiments, the substrate is any material that allows cells and/or tissue to adhere (or can be modified to allow cells and/or tissue to adhere or not adhere at select locations). Any number of materials can be used to form the substrate/surface, including but not limited to, polyamides; polyesters; polystyrene; polypropylene; polyacrylates; polyvinyl compounds (e.g., polyvinylchloride); polycarbonate; polytetrafluoroethylene (PTFE); nitrocellulose; cotton; polyglyolic acid (PGA); cellulose; dextran; gelatin; glass; fluoropolymers; fluorinated ethylene propylene; polyvinylidene; polydimethylsiloxane; and silicon substrates (such as fused silica, polysilicon, or single silicon crystals), and the like. Also, metals (e.g., gold, silver, titanium films) can be used.

In some embodiments, the substrate may be modified to promote cellular adhesion (e.g., coated with an adherence material). For example, a glass substrate may be treated with a protein (i.e., a peptide of at least two amino acids) such as collagen or fibronectin to assist cells of the tissue in adhering to the substrate. In some embodiments, a single protein is adhered to the substrate. In some embodiments, two or more proteins are adhered to the substrate. Proteins suitable for use in modifying the substrate to facilitate adhesion include proteins to which specific cell types adhere under cell culture conditions.

The type of adherence material(s) (e.g., ECM materials, sugars, proteoglycans, etc.) deposited on the substrate will be determined, in part, by the cell type or types in the tissue explant.

In some embodiments, the substrate does not require adherence material. Prior gastrointestinal culture systems utilizing primary cells require exogenous extracellular matrix. In some embodiments, the tissue explant described herein does not require exogenous extracellular matrix.

In some embodiments, the substrate is a singular well plate. In some embodiments, the substrate is a multi-well plate or assembly. In some embodiments, the substrate comprises microwells. In some embodiments, the substrate comprises 6, 12, 24, 48, 96, 384 or 1536 microwells. In some embodiments, the substrate comprises 96 microwells. In some embodiments, the substrate comprises 384 microwells. In some embodiments, the substrate comprises 1536 microwells. In some embodiments, each microwell is completely covered by the tissue explant described herein.

In some embodiments, the tissue explant is placed between a top plate and a bottom plate, wherein the top and bottom plate have a plurality of microwells. In some embodiments, the plurality of microwells in the top plate comprises through holes. In some embodiments, the plurality of microwells in the bottom plate comprises through holes. In some embodiments, the plurality of microwells in the bottom plate comprises receiving chambers.

In some embodiments, the tissue explant described herein is placed on an interface apparatus comprising a standard plate, a thin middle plate, and an upper load plate. The tissue explant is placed over the through holes of the middle plate and the upper load plate is then placed onto the tissue explant to compress it onto the middle plate and around the through holes, while mounted on the standard plate. In some embodiments, each plate comprises 6, 12, 24, 48, 96, 384 or 1536 microwells.

In some embodiments, the upper load plate comprises posts having a diameter from 3 mm to 5 mm. In some embodiments, the upper load plate comprises posts having a diameter from about 3 mm to about 5 mm. In some embodiments, the upper load plate comprises posts having a diameter of 4 mm. In some embodiments, the upper load plate comprises posts having a diameter of about 4 mm. In some embodiments, the tissue explant placed on the middle plate is slightly recessed into each well by forces from the upper plate. In some embodiments, the middle plate thickness is 1 mm or 2 mm. In some embodiments, the middle plate thickness is about 1 mm or about 2 mm. In some embodiments, the middle plate thickness is 1 mm. In some embodiments, the middle plate thickness is about 1 mm. In some embodiments, the diameter of posts of the middle plate is larger than the diameter of the upper load plate to ensure the tissue explant rests between the upper and middle plate. In some embodiments, the middle plate comprises posts having a diameter from 6.5 mm to 8 mm. In some embodiments, the middle plate comprises posts having a diameter from about 6.5 mm to about 8 mm. In some embodiments, the middle plate comprises posts having a diameter of 6 mm. In some embodiments, the middle plate comprises posts having a diameter of about 6 mm.

In some embodiments, the pressure applied to the tissue explant minimizes well-to-well leakage. In some embodiments, the pressure applied to the tissue explant is 20N, 15N, 10N, or 5N. In some embodiments, the pressure applied to the tissue explant is about 20N, about 15N, about 10N, or about 5N. In some embodiments, the pressure applied to the tissue explant is 5N. In some embodiments, the pressure applied to the tissue explant is about 5N.

According to other aspects of the present disclosure, the substrate assembly is suitable for use in a high-throughput drug absorption screening assay system, where the tissue explant is disposed in relatively planar contact with the microwells of the plates, thereby providing a luminal surface and a basolateral surface for allowing measurement of absorption of a drug through the tissue explant. In other aspects of the present disclosure, the substrate assembly is suitable for use in a high-throughput absorption-dissolution screening assay system, where the tissue explant is disposed in relatively planar contact with the microwells of the plates, thereby providing a luminal surface and a basolateral surface for allowing measurement of absorption of a drug through the tissue explant before or after measuring the dissolution of the drug.

In further aspects of the present disclosure, the substrate assembly is suitable for use in a high-throughput toxicity screening assay system, wherein the tissue explant is disposed in relatively planar contact with the microwells of the plates, thereby allowing for measurement of toxicity on the tissue explant. In yet further aspects of the present disclosure, the substrate assembly is suitable for use in a high-throughput GLP-1 stimulation screening assay system, wherein the tissue explant is disposed in relatively planar contact with the microwells of the plates, thereby providing a luminal and a basolateral surface for allowing measurement of GLP-1 secretion from the tissue explant.

According to still other aspects, the present disclosure also provides methods for determining absorption of a test compound through the tissue explant when placed in the substrate assembly. The top surface of the tissue explant forms a luminal surface and a bottom surface of the tissue explant forms a basolateral surface. The method also includes the steps of determining absorption of the test compound by detecting the presence of the test compound at the luminal surface and at the basolateral surface. The presence of the test compound at the basolateral surface indicates the ability of the compound to be absorbed through the tissue explant. In some aspects, detecting the presence of the test compound comprises determining concentration of the compound at the luminal and basolateral surfaces. A similar methodology can also be used to determine the perfusion rate of the test compound over time. In some aspects, the method further comprises determining the dissolution of the test compound.

Methods of Making Systems and Compositions

In some aspects, the disclosure provides compositions and/or systems comprising a substrate as described herein, and a tissue explant as described herein, wherein the tissue explant is contacted with the substrate. The systems and compositions are useful in the methods described herein, e.g., determining multiplex interactions.

In some embodiments, the tissue explant is in planar contact with the substrate. Planar contact can be determined by standard methods known to those of skill in the art. For example, a solution comprising a marker (e.g., fluorophore or colored compound) is added to the tissue explant when in contact with the substrate. The solution stains the surface of the tissue and enables detection of the tissue via photographic inspection, spectrophotometrics, or via laser scanner based techniques. If there is no significant difference in variability of the stain within the tissue explant in contact with the substrate, compared to an equivalent area of non-mounted tissue completely immersed in the solution, then the tissue explant is in planar contact with the substrate. In some embodiments, the substrate comprises a plurality of microwells. Accordingly, the solution comprising a marker can be placed within the microwells and a comparison between stain within the microwell and non-mounted tissue is carried out.

In some embodiments, planar contact is determined by coating the surface of a substrate with a marker prior to contacting it with the tissue explant, and analyzing the distribution of the marker. For example, the entire area of the substrate facing the tissue is coated with a marker that forms a uniform layer on the surface of the substrate. This coating stains the tissue when placed in close contact, and the resulting stain on the tissue remains intact after the substrate and tissue are separate. The resulting stain is analyzed by visual inspection, and if a regular pattern of markings corresponding to the substrate set-up is observed, the tissue explant is in planar contact with the substrate. In some embodiments, the substrate comprises a plurality of microwells and therefore the stain on the tissue can correlate with the microwell set-up.

In some embodiments, the substrate comprises a plurality of microwells, and upon contact with the tissue explant, each microwell is completely covered by the tissue explant. In some embodiments, well-to-well leakage is minimized. In some embodiments, complete coverage of the tissue explant by each microwell in a substrate minimizes well-to-well leakage.

In some embodiments, there is low sample variability between microwells when an intestinal tissue contact is in planar contact with a substrate comprising a plurality of microwells. Sample variability can be determined by standard methods known to those of skill in the art. For example, analysis of the perfusion of a drug can be determined in each microwell of the substrate and compared to determine sample variability.

In some embodiments, the tissue explant is contacted to the substrate immediately after it is excised from the gastrointestinal tract. In some embodiments, the tissue explant is kept in a first container (e.g., a cell strainer) for a period of time before being contacted to the substrate. In some embodiments, the properties of the tissue explant described herein are maintained when kept in a first container prior to contact with the substrate.

In some embodiments, the tissue explant is maintained for 24 hours, 2 days, 3 days, 1 week, 2 weeks, 3 weeks, 4 weeks or more, prior to being used in the methods described herein.

Definitions

Terms used in the claims and specification are defined as set forth below unless otherwise specified.

It must be noted that, as used in the specification and the claims, the singular forms "a," "an," and "the" include plural referents unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, "agent" refers to a molecule capable of reducing protein or RNA expression of a polypeptide of interest (e.g., drug transporter). In some embodiments, an agent interferes with transcription of a nucleic acid molecule encoding the polypeptide of interest. In some embodiments, an agent interferes with translation of a nucleic acid molecule encoding the polypeptide of interest. In some embodiments, an agent binds to the polypeptide of interest to reduce or inhibit function of the polypeptide. In some embodiments, an agent induces a temporary reduction or elimination of the polypeptide of interest. In some embodiments, an agent induces a permanent reduction or elimination of the polypeptide of interest. In some embodiments, an agent acts directly or indirectly on a nucleic acid molecule encoding the polypeptide of interest. In some embodiments, an agent acts directly or indirectly on the polypeptide of interest (e.g., binding to the polypeptide of interest vs interfering upstream).

As used herein, "architecture" refers to a tissue structure including the specific cell types within the tissue and the extracellular matrix surrounding the cells. In some embodiments, a tissue explant comprising intestinal epithelium from a large, non-human, mammalian gastrointestinal tract or a human gastrointestinal tract, wherein the intestinal epithelium comprises epithelial cells having a polarity in the tissue explant and the explant substantially maintains all or a substantial portion of the source architecture (e.g., the in vivo architecture) of the tissue from which it was derived (e.g., small intestine). For example, when the tissue explant comprises intestinal epithelium comprising epithelial cells having a polarity in the tissue explant, the polarity of the epithelial cells in the tissue explant is substantially maintained as in the source architecture of the tissue from which it was derived (e.g., small intestine). In some embodiments, the tissue explant described herein mimics in vivo architecture. In some embodiments, the tissue explant described herein mimics the in vivo architecture of the small intestine. In some embodiments, a tissue explant mimics in vivo architecture wherein it comprises one or more physical structures representative of the in vivo tissue from which it was derived. For example, wherein the tissue explant is derived from the small intestine, it mimics the in vivo architecture of the small intestine by comprising at least one structure of the small intestine from the tissue from which it was derived, for example, by comprising intact crypts, intestine epithelium, circular muscular layer and/or villi, or any combination of the foregoing. In some embodiments, a tissue explant mimics in vivo architecture by comprising one or more or a majority of the structures of the tissue from which it was derived, for example by comprising intact crypts, intestine epithelium, circular muscular layer and/or villi, or any combination of the foregoing. In some embodiments the tissue explant comprises intact crypts, intestine epithelium, circular muscular layer, and villi from the tissue from which it was derived (e.g., a large, non-human, mammalian gastrointestinal tract or a human gastrointestinal tract). In some embodiments, determination of the architecture of the tissue explant and whether it mimics the in vivo architecture of the tissue from which it is derived can be determined by standard techniques known in the art, for example, by comparing the structure of the tissue explant by methods described herein (e.g., histological staining) with images or information available to those of skill in the art (e.g., previously obtained images of the tissue from which the explant is derived). In some embodiments, comparisons are made between tissue explants cultured ex vivo and tissue explants freshly excised.

As used herein, "a basolateral surface" refers to the orientation of the tissue explant when contacted with a substrate, such that the tissue explant comprises apical/luminal-basolateral polarity. In some embodiments, the basolateral surface is opposite of the apical surface, i.e., the luminal surface.

As used herein, "breast cancer resistance protein" or "BCRP" refers to a polypeptide in the ATP-binding cassette (ABC) superfamily of transporter proteins and acts as an efflux pump.

As used herein, "contacting" refers to either placing a substrate on a tissue explant described herein (or causing a tissue explant to come in contact with a substrate), or placing a compound of interest on an intestinal tissue explant described herein (or causing a compound of interest to come in contact with an intestinal tissue explant).

As used herein, "detecting", "detect" and "detection" refer to the identification and/or quantification of a compound of interest (e.g., candidate drug) in a sample. In some embodiments, detecting comprises determining the absence or presence of a compound of interest in a sample. In some embodiments, detecting comprises quantifying a compound of interest in a sample. In some embodiments, detecting comprises identifying and/or quantifying a compound of interest in a sample at different time points. In some embodiments, detecting comprises identifying and/or quantifying a compound of interest in a first sample and in a second sample.

As used herein, "drug absorption" or "drug perfusion" refers to the movement of drug into the bloodstream and through tissues following administration, as well as movement of drug through the tissue explant following contact of drug with the tissue explant. Drug absorption or perfusion is determined by the drug's physicochemical properties, formulation, and route of administration.

As used herein, "drug dissolution" refers to the rate a dosage form (e.g., tablet) of a drug dissolves in the fluids of the gastrointestinal tract prior to absorption into the systemic circulation.

As used herein, "drug transporter" refers to proteins that move drugs across the cell membrane. In general, drug transporters are divided into two major superfamilies: ATP-binding cassette (ABC) family and solute carrier (SLC) family. The ABC transporters are primary active transporters that utilize the energy from ATP hydrolysis to transport substrates (e.g., drugs) across the membrane. SLC transporters can either be facilitative transporters, which transport their substrates down the gradient across the membrane, or secondary active transporters, which transport their substrates against the gradient across the membrane by coupling a downhill transport of another substrate.

As used herein, "drug-drug transporter interaction" refers to the association between a candidate drug and at least one drug transporter.

As used herein, "drug-drug interaction" refers to an association between two or more drugs that utilize at least one of the same drug transporters.

As used herein, "exogenous" refers to molecules or compositions originating or produced from outside an organism, tissue or cell.

As used herein, the "extracellular matrix" refers to a complex non-cellular three-dimensional macromolecular network composed of collagens, proteoglycans/glycosaminoglycans, elastin, fibronectin, laminins, and several other glycoproteins. These molecules are secreted locally by cells and remain closely associated with them to provide structural, adhesive and biochemical signaling support.

As used herein, "ex vivo" refers to a condition that takes place outside an organism. In some embodiments, ex vivo refers to experimentation or measurements done in or on a tissue from an organism in an external environment.

As used herein, "gastrointestinal tract" refers to the complete system of organs and regions that are involved with ingestion, digestion, and excretion of food and liquids. This system generally consists of, but is not limited to, the mouth, esophagus, stomach and or rumen, intestines (small and large), cecum (plural ceca), fermentation sacs, and the anus.

As used herein, "high-throughput" refers to the parallelization of experiments. Specifically, several experiments can be run simultaneously as opposed to single experiments carried out one after another. In some embodiments, high-throughput experiments are carried out using automated techniques.

As used herein, "intestinal cells" refers to cells that make up the mammalian intestinal epithelium. The mammalian intestinal epithelium of the gastrointestinal tract has a well-defined organizational structure. The epithelium can be divided into two regions, a functional region that houses differentiated cells (villi) and a proliferative region (crypts of Lieberkuhn) that represents the epithelium stem cell niche. Multipotent epithelium stem cells reside in the crypts and give rise to four principal epithelial lineages: absorptive enterocytes, mucin secreting goblet cells, peptide hormone secreting enteroendocrine cells, and Paneth cells.

As used herein, "intestine" refers to the mammalian small intestine and mammalian large intestine.

As used herein, "intestinal stem cells," used interchangeably with "epithelial stem cells" refers to stem cells that have the potential to proliferate and differentiate into intestinal epithelial cells. Multipotent epithelial stem cells give rise to various epithelial lineages, and may give rise to all intestinal epithelial lineages, which include: absorptive enterocytes, mucin secreting goblet cells, peptide hormone secreting enteroendocrine cells, and Paneth cells.

As used herein, "in vitro" refers to processes performed or taking place outside of a living organism. In some embodiments, the processes are performed or take place in a culture dish.

As used herein, "in vivo" refers to processes that occur in a living organism.

As used herein, "lamina propria" refers to a thin layer of loose connective tissue, or dense irregular connective tissue, which lies beneath the epithelium and together with the epithelium constitutes the mucosa.

As used herein, "lamina muscularis," "lamina muscularis mucosae" and "muscularis mucosae" refer to a thin layer of muscle of the gastrointestinal tract located outside the lamina propria and separating it from the submucosa.

As used herein, "large mammal" refers to a species in which normal mature adults of either sex may attain a body mass of at least one kilogram. In some embodiments, a large mammal is an ungulate (i.e., hoofed mammals such as pigs, cows, goats, sheep, horses, donkeys, deer, antelopes and the like). In some embodiments, a large mammal is livestock (i.e., mammals raised for agricultural purposes such as pigs, cows, goats, sheep, horses, rabbits, and the link, and/or as beasts of burden such as donkeys, horses, elephants, camels, llamas, and the like). In some embodiments, a large mammal is a human.

As used herein, "luminal surface" refers to the orientation of the tissue explant when contacted with a substrate, such that the tissue explant comprises apical/luminal-basolateral polarity. In some embodiments, the luminal surface is opposite of the basolateral surface.

As used herein, "maintained in culture" refers to the continued application of conditions that are required for the growth or survival of a specific cell type in an artificial environment. In some embodiments the artificial environment includes substrate or medium that supplies the essential nutrients (e.g., amino acids, carbohydrates, vitamins, minerals), growth factors, hormones, gases (e.g., $O_2$, $CO_2$), and physicochemical environment (e.g., pH, osmotic pressure, temperature). In some embodiments, the tissue explant described herein is maintained in culture for up to 1 week. In some embodiments, the tissue explant described herein is maintained in culture for up to 2 weeks. In some embodiments, the tissue explant described herein is maintained in culture for up to 3, 4, 5, 6, 7, 8, 9, 10, 11, 12, 13, 14, 15, 16 or 17 weeks. In some embodiments, the tissue explant described herein is maintained in culture for up to 18 weeks.

As used herein, "drug metabolizing enzyme", "DME" and "metabolizing enzyme" refer to polypeptides responsible for metabolizing a vast array of xenobiotic chemicals, including drugs, carcinogens, pesticides, pollutants and food toxicants, as well as endogenous compounds, such as steroids, prostaglandins and bile acids. Metabolic biotransformation of chemicals by DMEs form more hydrophilic, polar entities, which enhance their elimination from the body and lead to compounds that are generally pharmacologically inactive and relatively nontoxic. In some embodiments, metabolic biotransformation can lead to the formation of metabolites with pharmacological activity. Xenobiotics are metabolized by four different reactions: oxidation, reduction, hydrolysis and conjugation. Oxidation, reduction and hydrolysis are referred to as Phase I reactions, and conjugation is referred to as a Phase II reaction. Oxidative Phase I DMEs include cytochrome P450s (CYPs or P450s), Flavin-containing monooxygenases (FMOs), monoamine oxidase (MAOs), and xanthine oxidase/aldehyde oxidase (XO/AO). Conjugative Phase II DMEs include uridine 5'-diphospho (UDP)-glucuronosyltransferases (UGTs), sulfotransferases (SULTs), glutathione S-transferases (GSTs), N-acetyltransferase (NATs), and methyl (N-methyl-, thiomethyl-, and thiopurinemethyl-) taransferases. Of the DMEs involves in the metabolism of drugs, the dominant players are P450 enzymes, followed by UGTs and esterases. Accordingly, in some embodiments, the tissue explant described herein comprises Phase I and Phase II metabolizing enzymes. In some embodiments, the tissue explant described herein comprises a cytochrome P450 enzyme and a UGT enzyme.

As used herein, "modulation of gene expression" refers to changes in the induction or repression of a gene. Mechanisms that are involved with the gene regulation include structural and chemical changes to the genetic material, binding of proteins to specific DNA elements to regulate transcription, and/or mechanisms that modulate translation of mRNA. In some embodiments, gene expression of the tissue explant described herein is modulated. In some embodiments, gene expression of at least one drug transporter present in the tissue explant described herein is modulated. In some embodiments, gene expression of at least one metabolizing enzyme present in the tissue explant described herein is modulated.

As used herein, "monocarboxylate transporter 1" and "MCT1" is a member of the family of monocarboxylate transporters having 12 transmembrane domains, and is a proton-coupled transporter that cotransports a monocarboxylate molecule and a proton.

As used herein, "mucus" refers to a viscid secretion that is usually rich in mucins and is produced by mucous membranes which it moistens and protects. In some embodiments, the tissue explant described herein produces mucus.

As used herein, "multiplex interaction" refers to a particular way in which more than one drug and/or more than one drug transporter affects one another. In some embodiments, a multiplex interaction is an association between a candidate drug and two or more drug transporters. In some embodiments, a multiplex interaction is an association between a drug transporter of interest and two or more substrates (e.g., drugs). In some embodiments, a multiplex interaction is an association between multiple drug transporters and multiple substrates.

As used herein, "multidrug resistance protein 2" and "MRP2" refer to a member of the ABCC subfamily of the ATP-binding cassette transporter superfamily, and acts as an efflux pump.

As used herein, "muscularis externa" refers to the circular muscle layer and the longitudinal muscle layer, which separate the submucosa from the subserous layer. In some embodiments, the tissue explant described herein comprises an intact muscularis externa. In some embodiments, the tissue explant described herein comprises only the circular muscle layer.

As used herein, "oral bioavailability" refers to the degree to which a drug or other substance becomes available to a target tissue after oral administration. Bioavailability is related to the physiochemical properties of a drug or other substance, e.g., dissolution, membrane transport, chemical stability, etc., as well as the interactions with the host, e.g., metabolic fate, distribution and clearance. In some embodiments, the tissue explant described herein predicts the oral bioavailability of a drug or other substance of interest.

As used herein, "p-glycoprotein" and "p-gp" refers to a transmembrane protein member of the ATP-binding cassette (ABC) family and acts as an efflux pump to eject drugs from a cell or tissue.

As used herein, "Pearson product-moment correlation coefficient" or "Pearson correlation coefficient" refers to a measurement of the strength of a linear association between two variables and is denoted by "r".

As used herein, "peptide transporter 1" or "PEPT1" refers to a proton-driven peptide transporter having 12-transmembrane domains.

As used herein, "planar contact" refers to the placement of the tissue explant on a substrate, such that the tissue explant interacts with a two-dimensional surface of the substrate. Planar contact can be determined by methods known to those of skill in the art. For example, a method for analyzing planar contact comprises (i) contacting a tissue explant with a solution comprising a marker (e.g., dye) to stain the tissue and (ii) detecting the stain on the surface of the tissue by photographic inspection, spectrophotometrically or by laser scanner. The tissue explant is considered to be in planar contact with the substrate if there is no significant difference in variability of the marker within the area contacted with the substrate compared to an equivalent area of non-mounted tissue completely immersed in the solution comprising the marker. In another example, planar contact is determined by (i) coating the substrate with a marker that forms a uniform layer on the surface of the substrate; (ii) contacting the substrate with the tissue explant; and (iii) analyzing the resulting stain on the tissue explant once it is separated from the substrate by visual inspection. The tissue explant is considered to be in planar contact with the substrate if the tissue shows a regular pattern of markings across the entire tissue that correlate with the pattern of the substrate.

As used herein "polarity" refers to the organization of the cell membrane with associated proteins, along with the arrangement of the cytoskeleton and organelles within the cytoplasm. For example, epithelial cells are organized along a cellular axis that extends from the apical side facing an external lumen to the basal side facing either the extracellular matrix or adjacent cells. In addition to the apical-basal axis of polarity, epithelial cells are often oriented within the plane of the tissue along a proximal-distal axis, referred to as "tissue polarity" or "planar polarity". In some embodiments, the apical-basal axis of polarity of epithelial cells is maintained in the tissue explant following removal from the source tissue. In some embodiments, the apical-basal axis of polarity of epithelial cells is maintained in the tissue explant following contact with the substrate. In some embodiments, the apical-basal axis of polarity of epithelial cells is maintained in the intestinal tissue explant following use in the methods as described herein. In some embodiments, the proximal-distal axis of polarity is maintained in the tissue explant following removal from the source tissue. In some embodiments, the proximal-distal axis of polarity of epithelial cells is maintained in the tissue explant following contact with the substrate. In some embodiments, the proximal-distal axis of polarity of epithelial cells is maintained in the intestinal tissue explant following use in the methods as described herein. In some embodiments, both the apical-basal axis and proximal-distal axis of polarity are maintained in the tissue explant following contact with the substrate. In some embodiments, the apical-basal axis and the proximal-distal axis of polarity of epithelial cells is maintained in the tissue explant following contact with the substrate. In some embodiments, the apical-basal axis and proximal-distal axis of polarity of epithelial cells is maintained in the intestinal tissue explant following use in the methods as described herein. Methods of determining polarity are known to those of skill in the art. A review of such methods can be found in Chapter 7 of Cell Polarity and Morphogenesis (Academic Press, 2017, herein incorporated by reference in its entirety). In some embodiments, polarity of the tissue explant described herein is analyzed by visual (e.g., microscopic) inspection. For example, in some embodiments, the tissue explant described herein comprises two or more genetically distinct cell populations and polarity can be determined by expression of a labeled protein in only a subset of cells and subsequently visualized by microscopic techniques. In some embodiments, immunohistochemistry and live images of fluorescent reports are used to visualize proteins in their tissue context and evaluate their distribution. In some embodiments, cell polarization is quantified by analyzing protein localization in fluorescent images and calculating the ratio of fluorescence intensity between regions where the protein is present and regions where it is weakly localized or absent. The fluorescence ratio provides a quantitative measure of asymmetric protein distribution. See Marcinkevicius, E., et al. *J. Biol.* 2009, Vol. 8(12): 103, herein incorporated by reference in its entirety. In some embodiments, the fluorescence ratio is normalized by choosing appropriate analysis settings and incorporating internal controls, as described by Shimoni, R., et al. *PLos ONE* 2014, Vol. 9(6): e99885, herein incorporated by reference in its entirety.

As used herein, "reusable" refers to the ability of a tissue explant to be subjected to more than one experiment in succession.

As used herein, "responsive" refers to a reaction elicited by a stimulus. In some embodiments, the tissue explants described herein are responsive to a stimulus. In some embodiments, the tissue explant described herein is responsive to glucose. In some embodiments, increased GLP-1 activity (e.g., increased concentration of active GLP-1 7-36) indicates the tissue explant is responsive to glucose. In some embodiments, when the apical side of the tissue explant is contacted with glucose, GLP-1 activity is increased. In some embodiments, modulation of gut hormones and/or tissue behavior indicates the tissue explant is responsive to glucose. Methods for measuring gut hormones and tissue behavior are described herein.

As used herein, "substrate" refers to a surface or layer that underlies something, for example, a cell, cell culture, cell culture material, etc., or on which processes occur. In some embodiments, a substrate is a surface or material on which an organism lives, grows, and/or optionally obtains nourishment. The term "substrate" also refers to a surface or layer, e.g., a base surface or layer, on which another material is deposited. Exemplary substrates include, but are not limited to, glass, silicon, polymeric material, plastic (e.g., tissue culture plastic), etc. Substrates can be slides, chips, wells and the like.

As used herein, "tissue explant" refers to an isolated piece or pieces of tissue. In some embodiments, the tissue explant is isolated from the gastrointestinal tract.

EXAMPLES

Materials and Methods:
Cell Culture and shRNA/siRNA Transfection

The *Sus scrofa* kidney epithelial cell line PK15 was provided by Prof. George Church's lab at Harvard University and cultured in Dulbecco's modified Eagle's medium (DMEM, Invitrogen), high glucose supplemented with 10% fetal bovine serum (Invitrogen), and 1% penicillin/streptomycin (Invitrogen), as suggested by the commercial protocol. Cells were maintained in 37° C. incubator with 5% $CO_2$ supplement. shRNA/siRNA transfection was delivered into PK15 cell by standard lipofectamine 2000 kit (Invitrogen) according to the manufacture's protocol.
Tissue Dissection and Preparation Pig tissue was freshly sourced from local slaughter houses (i.e., Leman & Sons, Hilltown Pork, and Blood Farm). Small intestinal tissue was isolated from intact gastrointestinal tract immediately after euthanasia, and dissected longitudinally. A series of washes with PBS supplemented with 5% Antibiotic-Antimycotic solution (Thermo Fisher Scientific) was applied to the tissue until clean under sterile conditions. Then, the tissue was mounted on a device filled with PBS (5% Antibiotic-Antimycotic) solution and cultured at 37° C. incubation with 5% $CO_2$ supplement. Further description of the device and tissue explant is described in US 2019-0064153, herein incorporated by reference.
Transportome Interaction Graph DrugBank 5.0 was downloaded in XML format and all DrugBank entries with at least one known transporter were extracted in Python 2.6. For every such entry, the list of known transporters per entry was extracted and stored in a numpy array. These lists were then processed to identify the total number of substrates per transporter and the number of shared substrates per transporter pair, which were converted into an adjacency matrix and imported into Gephi 0.9.2. In this graph, every node corresponds to a drug transporter and two nodes are connected if and only if the corresponding two drug transporters share at least one known substrate according to DrugBank 5.0. The node size was determined from the total number of known substrates per transporter, using a logarithmic interpolation to ensure visibility of all nodes. Edge thickness was determined from the number of shared substrates and scaled linearly. Node position was determined using the Fruchterman Reingold layout algorithm. Chord charts to highlight the substrate sets for P-gp, BCRP, and MRP2 were generated using the R library circlize and further processed in Inkscape.
Transport Database Data was extracted from Drugbank 5.0, Metrabase 1.0, and from the NIH screen NCI-60. Drugbank and Metrabase compounds were filtered for compounds that were annotated to be substrates or non-substrates for P-gp, BCRP, and MRP2. Annotations were removed if contradicting information was present within one database. For the NIH screening data, previously published and validated protocols were followed to correlate treatment efficacy of various cytotoxic drugs against different cell lines with drug transporter expression levels for these cell lines. Briefly, if there is a sufficient anti-correlation between transporter expression level and cytotoxic effect of a drug (Pearson correlation coefficient <−0.2), the drug is assumed to be a substrate of the transporter under investigation, otherwise it can be assumed not to be transported by the specific transporter. To reflect the confidence in the annotations, annotations in DrugBank were prioritized over Metrabase annotations and DrugBank and Metrabase annotations were prioritized over data extracted from the NIH screen NCI-60. Compound identity was determined using a Morgan fingerprint (2048 bits, radius 4) with a Tanimoto similarity threshold of 0.95. This workflow provided a database of 2261 small molecule structures and their 4414 annotations as substrates and non-substrates for P-gp (648 and 1166), BCRP (395 and 991), and MRP2 (305 and 909). A Random Forest machine learning model was used based on this data to predict the missing annotations, i.e. substrate relationships for compounds that were included because of their relationship to other transporters (447 for P-gp, 875 for BCRP, and 1047 for MRP2). Manual literature research for randomly selected predictions showed that 70% of the high confidence predictions (substrate probability score >60% or <40%) were correct, while only half of the low confidence predictions (50%<substrate probability score <60%) were correct. This encouraged following of an active learning strategy to manually augment the dataset for these low confidence predictions by comprehensively scanning the literature for more information on compounds that were predicted with low confidence and annotate them in the dataset. This led to a larger training dataset with a total of 4554 annotations and 682 and 1183 annotations for P-gp, 424 and 1013 annotations for BCRP, and 323 and 929 annotations for MRP2.
Machine Learning Model Compounds from the training database were described using Morgan fingerprints (radius 4, 2048 bits). The machine learning model was a Random Forest Classifier (scikit-learn) using 500 tree estimators and no threshold on the number of included descriptors. Model quality was estimated retrospectively using 10-fold cross validation with pre-shuffling to ensure randomization of training and test sets. Investigational drugs were extracted from DrugBank by selecting compounds categorized as investigational but not in any of the other categories (e.g. approved or withdrawn), and compounds that were part of the training set were eliminated. This led to a total number of 1594 investigational drugs with unknown transport profile. Using the machine learning platform, the confidence score for each of these compounds to be transported by P-gp ($s_1$), BCRP ($s_2$), or MRP2 ($s_3$) was predicted. This resulted in three confidence scores $s_1$, $s_2$, $s_3$ each ranging from 0.0 to 1.0. Compounds were ranked according to how closely their predicted transport profile ($s_1$, $s_2$, $s_3$) would resemble any of the 2 3=8 different idealized profiles, specifically drugs that would not be transported by any of the three transporters (0, 0, 0), selectively transported drugs (1, 0, 0), (0, 1, 0), (0, 0, 1), drugs that would be transported by any pair of investigated transporters (1, 1, 0), (1, 0, 1), (1, 1, 0) and drugs that were predicted to be transported by all three transporters (1, 1, 1). By utilizing the Euclidean distance between the predicted profile ($s_1$, $s_2$, $s_3$) and any of these idealized profiles, a total of 1594×8=12,752 rank scores were generated.

Ultrasound siRNA Delivery siRNA duplex solution was diluted into PBS solution to a final concentration of 1 µM. For a 48-well magnet device, 300 µL of siRNA solution was added into each well, and the siRNA was delivered to tissue through a 12-head 40 kHz ultrasound device by applying 5s intervals for 1 minute with 30% amplitude as previously described (Schoellhammer, C. M., et al. Gastroenterology, Vol. 152: 1151-1160 (2017); Schoellhammer, C. M. & Traverso, G., Expert Opin Drug Deliv, Vol. 13: 1045-1048 (2016)). Tissue was cultured for 24 hours before the perfusion assay.

Western-Blotting

Tissue was dissected and snap frozen in liquid nitrogen. Every 1 mg of tissue sample was homogenized in 100 µL of RIPA buffer supplied with protease inhibitor (Roche) by Berkin 24-cycle homogenizer. After centrifugation, the protein concentration from the supernatant was determined by BCA assay (Pierce) according to manufactory protocol. A total of 100 µg of protein was loaded on each lane for western-blotting. The primary and secondary antibody working concentration is summarized in Table 1. Blots were imaged with Bio-rad universal Hood Ii Molecular Imager (1312M) with Chemiluminescence method. Contrast setting was set for auto-contrast for all images.

TABLE 1

List of antibody, suppliers and working concentration

| Target | Supplier | Concentration | Species |
|---|---|---|---|
| P-gp | LSBio | 1:250 | Rb |
| BCRP | abcam | 1:1000 | Rb |
| MRP2 | abcam | 1:500 | Rb |
| MCT1 | abcam | 1:500 | Rb |
| SNAT2 | abcam | 1:1000 | Rb |
| OST-a | abcam | 1:500 | Rb |
| PEPT1 | santa curze | 1:1000 | Ms |
| OCT1 | abcam | 1:500 | Rb |
| ABCC3 | sigma aldrich; LSBio; abcam | 1:250-1:1000 | Rb |
| GAPDH | abcam | 1:2000 | Ms |
| Actin | abcam | 1:2000 | Rb |
| anti-mouse (HRP) | abcam | 1:3000 | Rb |
| anti-rabbit (HRP) | abcam | 1:1000 | Gt |

Macro-Organoid Device Design and Manufacture

A 48-well device for interfacing with explanted porcine small intestine was designed and fabricated based on modifications from prior work (von Erlach, T. et al. Nat Biomed Eng (2020)). The device consists of a bottom reservoir plate and an upper load plate. Both plates were made by laser cutting (Universal Laser Systems VLS6.60) a standard 48-well plate outline and well pattern (Corning 48 well plate, transparent) as well as magnet holes onto an acrylic sheet (McMaster-Carr 1/4" thickness). Neodymium magnets (K&J Magnetics Cylinder, 3/16"×3/16", N52, NI) were press fitted into the magnet holes of both plates. Seal film (Thermo) was applied to seal the bottoms of the wells of the reservoir plate, and PBS solution was loaded into each well. Then, tissue was placed on top of the reservoir plate and the upper load plate was laid on top of the tissue. The magnets were oriented to align and attract the two plates together, ensuring a strong seal between the wells. Design details are provided in FIG. 1.

Drug Preparation and Detection

For ex vivo perfusion study, the detection of each drug is based on either fluorescent or absorbance measurements according to the literature. A 1 mg/mL drug stock was prepared for each drug in PBS (pH 7.4). For water-insoluble drugs, a final concentration of DMSO in PBS was used to solubilize drugs. A detailed drug list, preparation methods, and detection parameters is summarized in Table 2.

TABLE 2

List of name, preparation method and detection method for each model drug

| Drug Name | Target | CAS ID | Concentration mg/mL | Solute | Detection Wavelength (nm) |
|---|---|---|---|---|---|
| Colchicine | Pgp specific | 64-86-8 | 1 | PBS | U:350 |
| Irinotecan | Pgp specific | 100286-90-6 | 1 | PBS | F:370/470 |
| Loperamide | Pgp specific | 53179-11-6 | 1 | PBS | U:415 |
| Nicardipine | Pgp specific | 55985-32-5 | 1 | 5% methanol | U:415 |
| Ranitidine | Pgp specific | 66357-35-5 | 1 | PBS | U:312 |
| 4-methylumbelliferone sulfate | BCRP specific | 15220-11-8 | 1 | PBS | F:245/420 |
| Pitavastatin | BCRP specific | 147511-69-1 | 1 | 5% DMSO | F:315/375 |
| Rosuvastatin | BCRP specific | 287714-41-4 | 1 | 5% DMSO | F:280/534 |
| Mitoxantrone | BCRP specific | 65271-80-9 | 0.1 | PBS | F:660/685 |
| Daunorubicin | BCRP specific | 20830-81-3 | 0.5 | PBS | F:400/590 |
| Etoposide | MRP2 specific | 33419-42-0 | 1 | 10% DMSO | F:285/320 |
| Irinotecan | MRP2 specific | 100286-90-6 | 1 | PBS | F:370/470 |

TABLE 2-continued

List of name, preparation method and detection method for each model drug

| Drug Name | Target | CAS ID | Concentration mg/mL | Solute | Detection Wavelength (nm) |
|---|---|---|---|---|---|
| Olmesartan | MRP2 specific | 144689-63-4 | 1 | 10% DMSO | F:260/370 |
| p-aminohippurate acid | MRP2 specific | 61-78-9 | 1 | PBS | F:290/350 |
| Valsartan | MRP2 specific | 137862-53-4 | 1 | 5% ethanol | F:230/295 |
| Amoxicillin | PEPT1 specific | 26787-78-0 | 0.5 | PBS | F:260/370 |
| Cefadroxil | PEPT1 specific | 66592-87-8 | 0.5 | PBS | F:360/460 |
| Valacyclovir | PEPT1 specific | 124832-27-5 | 0.2 | PBS | F:345/420 |
| Enalapril | PEPT1 specific | 75847-73-3 | 0.5 | 5% DMSO | U:272 |
| Cephalexin | PEPT1 specific | 15686-71-2 | 1 | 20 mM NH4OH | F:268/314 |
| Paraquat | MCT1 specific | 4685-14-7 | 0.5 | PBS | U:267 |
| Ganciclovir | MCT1 specific | 82410-32-0 | 1 | PBS | F:257/374 |
| Acyclovir | MCT1 specific | 59277-89-3 | 1 | PBS | F:250/410 |
| Carbamazepine | Pgp non specific | 298-46-4 | 0.2 | 5% DMSO | F:300/357 |
| Chlorpheniramine | Pgp non specific | 132-22-9 | 1 | PBS | F:350/500 |
| Doxorubicin | BCRP non specific | 23214-92-8 | 1 | PBS | F:308/592 |
| LysoTracker Green ® | BCRP non specific | NA | 50 μM | 5% DMSO | F:504/511 |
| Rhodamine 123 | BCRP non specific | 62669-70-9 | 0.1 | 5% DMSO | F:507/530 |
| Colchicine | MRP2 non specific | 64-86-8 | 1 | PBS | U:350 |
| Digoxin | MRP2 non specific | 20830-75-5 | 1 | 5% ethanol | F:318/374 |
| Nitrofurantoin | MRP2 non specific | 67-20-9 | 0.1 | 5% DMSO | F:378:546 |
| Lanreotide | PEPT1 non specific | 108736-35-2 | 0.1 | 4% Tween-80 | F:295/352 |
| Gonadorelin | PEPT1 non specific | 33515-09-2 | 1 | PBS | U:278 |
| Glyoxylate | MCT1 non specific | 918149-31-2 | 1 | PBS | U:350 |
| Glycopyrrolate | MCT1 non specific | 596-51-0 | 1 | 5% DMSO | U:545 |

In Vivo Pharmacokinetic Analysis of Predicted Drug Transporter Substrates

All animal procedures were conducted in accordance with protocols approved by the Massachusetts Institute of Technology Committee on Animal Care. For in vivo pharmacokinetic evaluation, male Balb/c mice between 10-12 weeks were used in this study. For each studied drug, two groups were included, and three time points (15, 30, and 60 minutes)—each time point contained 5 mice for each group. The control group was designed to obtain a baseline of absorption for the investigated drug where no specific drug transporter inhibitor was used. For the experimental group, drug transporter-specific inhibitors were pre-administered through oral gavage 15 mins before the administration of the investigated drugs. For each time point, 1 ml of blood was drained from the mice after oral gavage administration. The blood was further treated by centrifugation, then by protein precipitation with acetonitrile in preparation for LC-MS/MS analysis. A detailed oral gavage drug list, preparation, administration concentration and volume can be found in Table 3.

TABLE 3

List of name, preparation method and detection method of each in-house drug for mock screening

| Drug Name | CAS ID | Concentration mg/mL | Solute | Detection Wavelength |
|---|---|---|---|---|
| Dihydroergotamine (+)-tartrate salt | 5989-77-5 | 1 | 5% Methanol | F:277/348 |
| ±)-Verapamil hydrochloride | 152-11-4 | 1 | PBS | F:280/360 |
| Ibuprofen | 15687-27-1 | 1 | 5% DMSO | F:231/295 |
| Curcumin | 458-37-7 | 0.2 | 5% DMSO | F:420/470 |
| Atorvastatin calcium salt trihydrate | 344423-98-9 | 0.2 | 5% DMSO | F:282/400 |
| Candesartan cilexetil | 139481-59-7 | 0.2 | 5% DMSO | F:310/400 |
| Warfarin | 81-81-2 | 1 | PBS | F:331/382 |
| Quinine | 130-95-0 | 1 | 5% Ethanol | F:331/382 |
| Quinidine | 56-54-2 | 1 | 5% DMSO | F:331/380 |
| Coumarin | 91-64-5 | 1 | PBS | F:320/380 |
| Pamidronate disodium salt hydrate | 57248-88-1 | 1 | PBS | F:395/480 |
| Acyclovir | 59277-89-3 | 1 | PBS | F:250/410 |

TABLE 3-continued

List of name, preparation method and detection method of each in-house drug for mock screening

| Drug Name | CAS ID | Concentration mg/mL | Solute | Detection Wavelength |
|---|---|---|---|---|
| Furosemide | 54-31-9 | 1 | PBS in pH 8.0 | F:237/415 |
| Chlorotetracycline | 57-62-5 | 1 | PBS | F:392/536 |
| Doxycycline | 564-25-0 | 1 | PBS | F:400/590 |
| Ergotamine D-tartrate | 379-79-3 | 1 | 0.15M citric acid-NaOH in acetate buffer, pH 5.5 | F:250/430 |
| Labetalol hydrochloride | 32780-64-6 | 1 | 5% Na2CO3 in pH 7.3 | U:302 |
| Danazol | 17230-88-5 | 1 | 5% DMSO | U:300 |
| Ketoprofen | 22071-15-4 | 1 | 5% DMSO wit 1% Tween-80 | U:290 |
| Piroxicam | 36322-90-4 | 1 | PBS | U:312 |
| Ranitidine | 66357-35-5 | 1 | PBS | U:280 |
| Carbamazepine | 298-46-4 | 1 | 5% DMSO | U:280 |
| Terbutaline | 23031-25-6 | 1 | PBS | U:282 |
| L-phenylalanine | 63-91-2 | 1 | PBS | U:280 |
| Narpoxen | 22204-53-1 | 1 | 5% DMSO | U:331 |
| S)-(−)-Propranolol hydrochloride | 4199-10-4 | 1 | PBS | U:290 |
| Loperamide | 53179-11-6 | 1 | PBS in pH 7.0 | U:300 |
| Nadolol | 42200-33-9 | 1 | PBS | U:280 |

RT-PCR and Q-PCR

RNA from cell and tissue were extracted with the Trizol extraction method and converted into cDNA according to the manufacturer's protocol (Qiagen RNA extraction kit and AB high fidelity cDNA synthesis kit), followed by UV-vis quantification. The detection of each target was achieved by PCR, agarose electrophoresis and SYBR Green Q-PCR detection method with specific primers listed in the Tables 4 & 5. All gels were detected with Bio-rad Universal Ii Molecular imager and processed with ImageJ for any quantitative analysis.

TABLE 4

RT-PCR and Q-PCR primers

| Name | Sequence |
|---|---|
| P-gp_F | CCGAATCGAAAGAGCAGGGAA (SEQ ID NO: 1) |
| P-gp_R | ATCTCCTGCCGCATGATAGC (SEQ ID NO: 2) |
| MRP2_F | AACACCCATAGGCCGGATTG (SEQ ID NO: 3) |
| MRP2_R | AAAGGCACGGATAACAGGCA (SEQ ID NO: 4) |
| BCRP_F | AAAGGAACACCAATGGCCTG (SEQ ID NO: 5) |
| BCRP_R | GGGTCCCAGAATGGCATTGA (SEQ ID NO: 6) |
| SNAT2_F | TGTGGGCAGTGGAATCCTTG (SEQ ID NO: 7) |
| SNAT2_R | GGCCACTGGTGTATCCCAAA (SEQ ID NO: 8) |
| PET1_F | TTGTGGCTCTGTGCTACCTG (SEQ ID NO: 9) |
| PET1_R | ACACACAGGGCTTTATCCCG (SEQ ID NO: 10) |
| MCT1_F | TGGGGGCTTGCTGTTAAACT (SEQ ID NO: 11) |
| MCT1_R | ATGGTCACCAATCCCACAGC (SEQ ID NO: 12) |
| ABCC3_F | ACCAGCAAGGCTACATCGTC (SEQ ID NO: 13) |
| ABCC3_R | GATCACGCACAGGAACCAGA (SEQ ID NO: 14) |
| OCT1_F | CGTTCTTAGACCTGTTCCGCA (SEQ ID NO: 15) |
| OCT1_R | AAGCGGTCGATGATGAGGAG (SEQ ID NO: 16) |

TABLE 4-continued

RT-PCR and Q-PCR primers

| Name | Sequence |
|---|---|
| OSTa_F | AGCTTCTGAGAGCATTGGGC (SEQ ID NO: 17) |
| OSTa_R | TGCACATCGCGAAAAACGAG (SEQ ID NO: 18) |
| Pgp_qPCR_F | TGCTGGTTGCTGCTTACA (SEQ ID NO: 19) |
| Pgp_qPCR_R | GCCTATCTCCTGTCGCATTATAG (SEQ ID NO: 20) |
| MRP2_qPCR_F | CCTTGGTCTACACACGGTAATC (SEQ ID NO: 21) |
| MRP2_qPCR_R | GGACAAGTGGATCTGACATGAG (SEQ ID NO: 22) |
| BCRP_qPCR_F | TCCGACCACCATGACAAATC (SEQ ID NO: 23) |
| BCRP_qPCR_R | CCAGACACACCACGGATAAA (SEQ ID NO: 24) |
| SNAT2_qPCR_F | CGCAGCCGTAGAAGAATGAT (SEQ ID NO: 25) |
| SNAT2_qPCR_R | CGTCTCAACGTGGTCGTAAA (SEQ ID NO: 26) |
| PEPT1_qPCR_F | TGCAGATCCCGCAGTATTTC (SEQ ID NO: 27) |
| PEPT1_qPCR_R | GTTGGAAGGAGCCTGAGAATAG (SEQ ID NO: 28) |
| MCT1_qPCR_F | TACTGGGCATGTGGCATAATC (SEQ ID NO: 29) |
| MCT1_qPCR_R | CTGCTGCTTCTCTGCTTTCT (SEQ ID NO: 30) |
| ABCC3_qPCR_F | GTCCTGGACAAAGGGACAATAG (SEQ ID NO: 31) |
| ABCC3_qPCR_R | TTTAGGCAAGTCCAGCATCTC (SEQ ID NO: 32) |
| OST-a_qPCR_F | GATCCAGACAGGACTCAGATAAAG (SEQ ID NO: 33) |
| OST-a_qPCR_R | GATATGCAGTGGGAGGGTAAG (SEQ ID NO: 34) |
| OCT1_qPCR_F | GTCAGTATGGCTGGGTGTATG (SEQ ID NO: 35) |
| OCT1_qPCR_R | GTTCACACAGGACTGGAAGAG (SEQ ID NO: 36) |

TABLE 5 shRNA and siRNA sequences

| Name | Sequence |
|---|---|
| P-gp_shRNA_334_F | CCGGATGACAGTGTACGCCTATTATCTCGAGATAATAGGCGTACACTGTCATTTTTTG (SEQ ID NO: 37) |
| P-gp_shRNA_334_R | AATTCAAAAAATGACAGTGTACGCCTATTATCTCGAGATAATAGGCGTACACTGTCAT (SEQ ID NO: 38) |
| P-gp_shRNA_962_F | CCGGTGGTCCTCTCAAATGAATATACTCGAGTATATTCATTTGAGAGGACCATTTTTG (SEQ ID NO: 39) |
| P-gp_shRNA_962_R | AATTCAAAAATGGTCCTCTCAAATGAATATACTCGAGTATATTCATTTGAGAGGACCA (SEQ ID NO: 40) |
| P-gp_shRNA_1391_F | CCGGTAAGGTATCTGCGGGAAATTACTCGAGTAATTTCCCGCAGATACCTTATTTTTG (SEQ ID NO: 41) |
| P-gp_shRNA_1391_R | AATTCAAAAATAAGGTATCTGCGGGAAATTACTCGAGTAATTTCCCGCAGATACCTTA (SEQ ID NO: 42) |
| MRP2_shRNA_292_F | CCGGGGCAGCTTATTCATGTATATACTCGAGTATATACATGAATAAGCTGCCTTTTTG (SEQ ID NO: 43) |
| MRP2_shRNA_292_R | AATTCAAAAAGGCAGCTTATTCATGTATATACTCGAGTATATACATGAATAAGCTGCC (SEQ ID NO: 44) |
| MRP2_shRNA_1681_F | CCGGGGATCAAGATCCTGAAATATTCTCGAGAATATTTCAGGATCTTGATCCTTTTTG (SEQ ID NO: 45) |
| MRP2_shRNA_1681_R | AATTCAAAAAGGATCAAGATCCTGAAATATTCTCGAGAATATTTCAGGATCTTGATCC (SEQ ID NO: 46) |
| MRP2_shRNA_3239_F | CCGGGGGATTAGCACAAGGTATATTCTCGAGAATATACCTTGTGCTAATCCCTTTTTG (SEQ ID NO: 47) |
| MRP2_shRNA_3239_R | AATTCAAAAAGGGATTAGCACAAGGTATATTCTCGAGAATATACCTTGTGCTAATCCC (SEQ ID NO: 48) |
| BCRP_shRNA_1268_F | CCGGGCGTCCGTAGCCCAGATAATTCTCGAGAATTATCTGGGCTACGGACGCTTTTTG (SEQ ID NO: 49) |
| BCRP_shRNA_1268_R | AATTCAAAAAGCGTCCGTAGCCCAGATAATTCTCGAGAATTATCTGGGCTACGGACGC (SEQ ID NO: 50) |
| BCRP_shRNA_1436_F | CCGGGTGGAGAAGAAACTCTTTATACTCGAGTATAAAGAGTTTCTTCTCCACTTTTTG (SEQ ID NO: 51) |
| BCRP_shRNA_1436_R | AATTCAAAAAGTGGAGAAGAAACTCTTTATACTCGAGTATAAAGAGTTTCTTCTCCAC (SEQ ID NO: 52) |
| BCRP_shRNA_960_F | CCGGACTTCTTCCTGGACGTCATTACTCGAGTAATGACGTCCAGGAAGAAGTTTTTTG (SEQ ID NO: 53) |
| BCRP_shRNA_960_R | AATTCAAAAAACTTCTTCCTGGACGTCATTACTCGAGTAATGACGTCCAGGAAGAAGT (SEQ ID NO: 54) |
| SNAT2_shRNA_251_F | CCGGCCTTTGGAATGTCAGTATTTACTCGAGTAAATACTGACATTCCAAAGGTTTTTG (SEQ ID NO: 55) |
| SNAT2_shRNA_251_R | AATTCAAAAACCTTTGGAATGTCAGTATTTACTCGAGTAAATACTGACATTCCAAAGG (SEQ ID NO: 56) |
| SNAT2_shRNA_625_F | CCGGTTGTCACTGCTGAGGAATTTACTCGAGTAAATTCCTCAGCAGTGACAATTTTTG (SEQ ID NO: 57) |
| SNAT2_shRNA_625_R | AATTCAAAAATTGTCACTGCTGAGGAATTTACTCGAGTAAATTCCTCAGCAGTGACAA (SEQ ID NO: 58) |
| SNAT2_shRNA_738_F | CCGGTGTGGAAGTTGCTATAATAATCTCGAGATTATTATAGCAACTTCCACATTTTTG (SEQ ID NO: 59) |
| SNAT2_shRNA_738_R | AATTCAAAAATGTGGAAGTTGCTATAATAATCTCGAGATTATTATAGCAACTTCCACA (SEQ ID NO: 60) |

TABLE 5-continued shRNA and siRNA sequences

| Name | Sequence |
|---|---|
| PEPT1_shRNA_787_F | CCGGGACTGGGCCAAGGAGAAATATCTCGAGATATTTCTCCTTGGCCCAGT CTTTTTG (SEQ ID NO: 61) |
| PEPT1_shRNA_787_R | AATTCAAAAAGACTGGGCCAAGGAGAAATATCTCGAGATATTTCTCCTTGG CCCAGTC (SEQ ID NO: 62) |
| PEPT1_shRNA_1296_F | CCGGCAACAAACTGACAAGTATAAACTCGAGTTTATACTTGTCAGTTTGTTG TTTTTG (SEQ ID NO: 63) |
| PEPT1_shRNA_1296_R | AATTCAAAAACAACAAACTGACAAGTATAAACTCGAGTTTATACTTGTCAG TTTGTTG (SEQ ID NO: 64) |
| PEPT1_shRNA_1968_F | CCGGCCTCGCCGTCTGCATAATATTCTCGAGAATATTATGCAGACGGCGAG GTTTTTG (SEQ ID NO: 65) |
| PEPT1_shRNA_1968_R | AATTCAAAAACCTCGCCGTCTGCATAATATTCTCGAGAATATTATGCAGAC GGCGAGG (SEQ ID NO: 66) |
| MCT1_shRNA_256_F | CCGGAGTATCCTGGTGAATAAATATCTCGAGATATTTATTCACCAGGATACT TTTTTG (SEQ ID NO: 67) |
| MCT1_shRNA_256_R | AATTCAAAAAAGTATCCTGGTGAATAAATATCTCGAGATATTTATTCACCA GGATACT (SEQ ID NO: 68) |
| MCT1_shRNA_631_F | CCGGCCAACCACTGCAGACAAATATCTCGAGATATTTGTCTGCAGTGGTTG GTTTTTG (SEQ ID NO: 69) |
| MCT1_shRNA_631_R | AATTCAAAAACCAACCACTGCAGACAAATATCTCGAGATATTTGTCTGCAG TGGTTGG (SEQ ID NO: 70) |
| MCT1_shRNA_1130_F | CCGGGGTGGCTCAGCTCAGTATTATCTCGAGATAATACTGAGCTGAGCCAC CTTTTTG (SEQ ID NO: 71) |
| MCT1_shRNA_1130_R | AATTCAAAAAGGTGGCTCAGCTCAGTATTATCTCGAGATAATACTGAGCTG AGCCACC (SEQ ID NO: 72) |
| ABCC3_shRNA_1095_F | CCGGCAGCATCCTGATCAGATTTATCTCGAGATAAATCTGATCAGGATGCT GTTTTTG (SEQ ID NO: 73) |
| ABCC3_shRNA_1095_R | AATTCAAAAACAGCATCCTGATCAGATTTATCTCGAGATAAATCTGATCAG GATGCTG (SEQ ID NO: 74) |
| ABCC3_shRNA_2329_F | CCGGATTGGAGAGAAGGGCATTAATCTCGAGATTAATGCCCTTCTCTCCAA TTTTTTG (SEQ ID NO: 75) |
| ABCC3_shRNA_2329_R | AATTCAAAAAATTGGAGAGAAGGGCATTAATCTCGAGATTAATGCCCTTCT CTCCAAT (SEQ ID NO: 76) |
| ABCC3_shRNA_1098_F | CCGGCATCCTGATCAGATTTATTTCCTCGAGGAAATAAATCTGATCAGGATG TTTTTG (SEQ ID NO: 77) |
| ABCC3_shRNA_1098_R | AATTCAAAAACATCCTGATCAGATTTATTTCCTCGAGGAAATAAATCTGATC AGGATG (SEQ ID NO: 78) |
| OST-a_shRNA_273_F | CCGGGAAGATATTGGAAGTCAATTACTCGAGTAATTGACTTCCAATATCTTC TTTTTG (SEQ ID NO: 79) |
| OST-a_shRNA_273_R | AATTCAAAAAGAAGATATTGGAAGTCAATTACTCGAGTAATTGACTTCCAA TATCTTC (SEQ ID NO: 80) |
| OST-a_shRNA_818_F | CCGGTCATCCCTGACGGCATCTATACTCGAGTATAGATGCCGTCAGGGATG ATTTTTG (SEQ ID NO: 81) |
| OST-a_shRNA_818_R | AATTCAAAAATCATCCCTGACGGCATCTATACTCGAGTATAGATGCCGTCA GGGATGA (SEQ ID NO: 82) |
| OST-a_shRNA_988_F | CCGGCTATTCCAGGTGCTCCTTATTCTCGAGAATAAGGAGCACCTGGAATA GTTTTTG (SEQ ID NO: 83) |
| OST-a_shRNA_988_R | AATTCAAAAACTATTCCAGGTGCTCCTTATTCTCGAGAATAAGGAGCACCT GGAATAG (SEQ ID NO: 84) |
| OCT1_shRNA_956_F | CCGGGAGAAACACTCAAGCAATAAACTCGAGTTTATTGCTTGAGTGTTTCTC TTTTTG (SEQ ID NO: 85) |

TABLE 5-continued shRNA and siRNA sequences

| Name | Sequence |
|---|---|
| OCT1_shRNA_956_R | AATTCAAAAAGAGAAACACTCAAGCAATAAACTCGAGTTTATTGCTTGAGT GTTTCTC (SEQ ID NO: 86) |
| OCT1_shRNA_739_F | CCGGACACACTGATCACAGAATTTGCTCGAGCAAATTCTGTGATCAGTGTG TTTTTTG (SEQ ID NO: 87) |
| OCT1_shRNA_739_R | AATTCAAAAAACACACTGATCACAGAATTTGCTCGAGCAAATTCTGTGATC AGTGTGT (SEQ ID NO: 88) |
| OCT1_shRNA_1688_F | CCGGGCCCAGAGACAACATGATTTACTCGAGTAAATCATGTTGTCTCTGGG CTTTTTG (SEQ ID NO: 89) |
| OCT1_shRNA_1688_R | AATTCAAAAAGCCCAGAGACAACATGATTTACTCGAGTAAATCATGTTGTC TCTGGGC (SEQ ID NO: 90) |
| Pgp_sense | AUGACAGUGUACGCCUAUUAU[dT][dT] (SEQ ID NO: 91) |
| Pgp_anti | AUAAUAGGCGUACACUGUCAU[dT][dT] (SEQ ID NO: 92) |
| MRP2_sense | GGCAGCUUAUUCAUGUAUAUA[dT][dT] (SEQ ID NO: 93) |
| MRP2_anti | UAUAUACAUGAAUAAGCUGCC[dT][dT] (SEQ ID NO: 94) |
| BCRP_sense | ACUUCUUCCUGGACGUCAUUA[dT][dT] (SEQ ID NO: 95) |
| BCRP_anti | UAAUGACGUCCAGGAAGAAGU[dT][dT] (SEQ ID NO: 96) |
| SNAT2_sense | UUGUCACUGCUGAGGAAUUUA[dT][dT] (SEQ ID NO: 97) |
| SNAT2_anti | UAAAUUCCUCAGCAGUGACAA[dT][dT] (SEQ ID NO: 98) |
| PEPT1_sense | CAACAAACUGACAAGUAUAAA[dT][dT] (SEQ ID NO: 99) |
| PEPT1_anti | UUUAUACUUGUCAGUUUGUUG[dT][dT] (SEQ ID NO: 100) |
| MCT1_sense | GGUGGCUCAGCUCAGUAUUAU[dT][dT] (SEQ ID NO: 101) |
| MCT1_anti | AUAAUACUGAGCUGAGCCACC[dT][dT] (SEQ ID NO: 102) |
| ABCC3_sense | CAGCAUCCUGAUCAGAUUUAU[dT][dT] (SEQ ID NO: 103) |
| ABCC3_anti | AUAAAUCUGAUCAGGAUGCUG[dT][dT] (SEQ ID NO: 104) |
| OST-a_sense | GAAGAUAUUGGAAGUCAAUUA[dT][dT] (SEQ ID NO: 105) |
| OST-a_anti | UAAUUGACUUCCAAUAUCUUC[dT][dT] (SEQ ID NO: 106) |
| OCT1_sense | ACACACUGAUCACAGAAUUUG[dT][dT] (SEQ ID NO: 107) |
| OCT1_anti | CAAAUUCUGUGAUCAGUGUGU[dT][dT] (SEQ ID NO: 108) |

Liquid Chromatograph and Mass Spectrometry Analysis

Samples were analyzed via Ultra Performance Liquid Chromatography Tandem Mass Spectrometry (UPLC-MS/MS). For each time point, 500 uL of mice serum was collected and underwent standard liquid extrusion before LC-MS/MS analysis (see details in Supporting Information). Analysis was performed on a Waters® ACQUITY UPLC®-I-Class System aligned with a Waters® Xevo-TQ-S mass spectrometer (Waters Corp., Milford, MA). Liquid chromatographic separation was performed on an Acquity® UPLC Charged Surface Hybrid C18 (50 mm×2.1 mm, 1.7 µm particle size) column at 50° C. The mobile phase consisted of aqueous 0.1% formic acid, 10 mM ammonium formate solution (Mobile Phase A) and acetonitrile containing 10 mM ammonium formate in a 0.1% formic acid solution (95:5 v/v) (Mobile Phase B). The mass spectrometer was operated in the multiple reaction monitoring (MRM) mode. Sample introduction and ionization was done by electrospray ionization (ESI) in the positive ionization mode for all compounds except atorvastatin and aspirin, which were operated in negative ionization mode. MassLynx® 4.1 software was used for data acquisition and analysis. The drug concentration for each sample was calculated from a standard linear curve generated by standard sample and internal standard. The mobile phase had a continuous flow rate of 0.60 mL/min using a time and solvent gradient composition.

Clinical Trial Design and Data Analysis

Institutional Review Board (IRB) approval from Partners Healthcare was obtained prior to any work. Using the Partners Research Patient Data Registry (RPDR), patients on warfarin, tacrolimus, digoxin and levetiracetam therapy who received a short course of doxycycline therapy for an acute infection were retrospectively identified. All patients were treated at Massachusetts General Hospital or Brigham and Women's Hospital between January 2010 and December 2019. For patients on warfarin therapy, PT-INR values were recorded for the following time periods: 3 months prior to doxycycline therapy to establish a stable baseline, during doxycycline therapy and 3 days post-doxycycline therapy, and 3 months post-doxycycline therapy. For patients on tacrolimus therapy, serum tacrolimus trough levels were recorded for the following time periods: 3 months prior to doxycycline therapy to establish a stable baseline, during doxycycline therapy and 1 day post-doxycycline therapy, and 3 months post-doxycycline therapy. For patients on digoxin therapy, serum digoxin levels were recorded for the following periods: 1 year prior to doxycycline therapy to establish a stable baseline, during doxycycline therapy and 1 day post-doxycycline therapy, and 1 year post-doxycycline therapy. Lastly, for patients on levetiracetam therapy, serum levetiracetam levels were recorded for the following periods: 1 year prior to doxycycline therapy to establish a stable baseline, during doxycycline therapy and 1 day post-doxycycline therapy, and 1 year post-doxycycline therapy. The means values for these cohorts were calculated and compared using a paired T-test between cohorts.

Example 1: Establishment of Transportome Inter-Connectivity

To understand the potential for a drug to be transported by multiple transporters, the incidence of known drug transporter pairs with shared substrates was first evaluated. To this end, all drug transporter data from the DrugBank (Wishart, D. S. et al, Nucleic Acids Res, vol 46: D1074-D1082 (2018)) database was extracted and individual transporters according to their shared substrates was analyzed. DrugBank 5.0 contains 149 distinct drug transporters that have a total of 917 annotated substrates. The three transporters with the highest number of annotated substrates are the three efflux transporters P-glycoprotein (P-gp, 186 substrates), breast cancer resistance protein (BCRP, 70 substrates), and multidrug resistance 2 (MRP2, 43 substrates) and a total of 106 substrates are partially or fully shared between them. Overall, the DrugBank dataset contains a total of 1891 transporter-tranporter interactions, i.e. pairs of transporters that have at least one shared substrate. This corresponds to 17% of the possible number of interactions, which shows that shared substrates are a common phenomenon but at the same time do not impact every possible transporter pair. This further demonstrates that transporters possess a complex molecular recognition mechanism of substrates as well as a need to develop an advanced platform that enables the rapid and accurate profiling of these transporter-drug interactions.

Figure 2A:
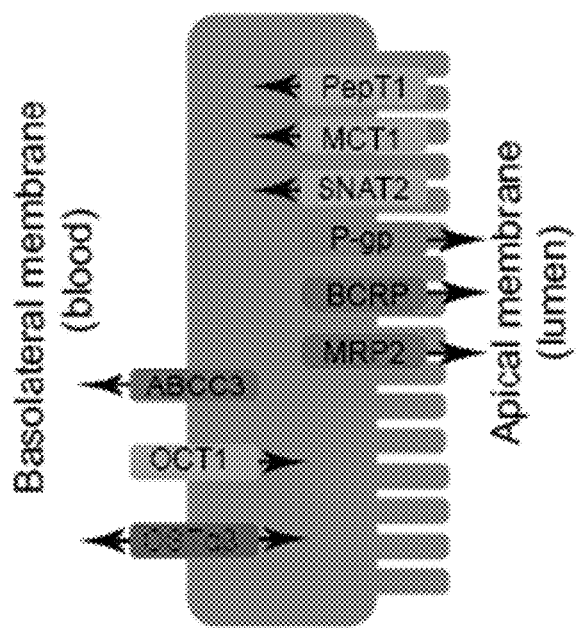
FIG. 2A is a schematic showing location of known drug transporters within intestinal tissue and the direction in which the transporters act.
Figure 2B:
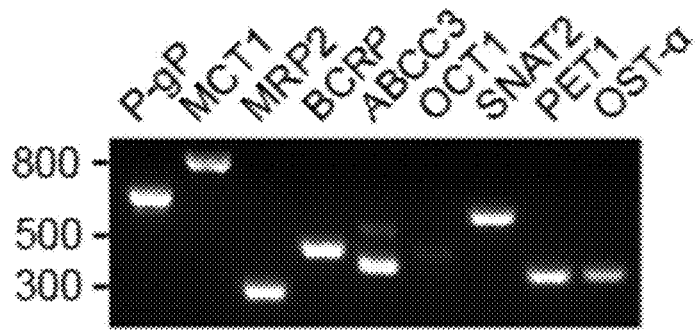
FIGS. 2B-2C show expression of various drug transporters within the intestinal tissue explant as measured by RT-PCR (FIG. 2B) and western-blot (FIG. 2C).
Figure 2C:
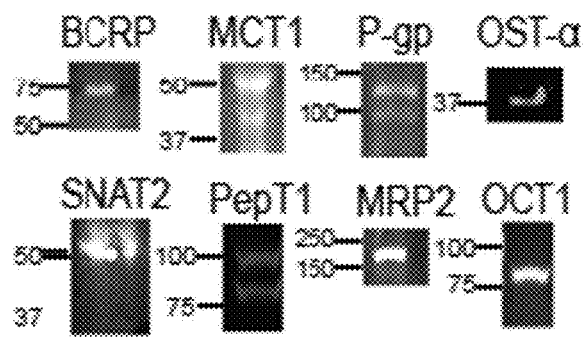

Example 2: A siRNA-Engineered Ex Vivo Platform Enables the Characterization of Substrate Transport in Response to Modulation of Drug Transporter Expression The drug transporters expressed within the small intestine have been studied extensively (International Tranpsorter, C. Nat Rev Drug Discov, vol 9: 215-236 (2015); Englund, G. et al. Eur J Pharm Sci, vol 29: 269-277 (2006); Kunta, J. R. & Sink, P. J., Curr Drug Metab, vol 5: 109-124 (2004)). Briefly, three efflux transporters (PgP, BCRP, and MRP2) and three influx transporters (MCT1, SNAT2, and PEPT1) are expressed on the luminal side. The basolateral side contains one efflux (ABCC3), one influx (OCT1), and one bi-directional transporter (OSTα/β) (FIG. 2A). It was hypothesized that porcine tissue could be a viable model system to study these drug transporters given the similarity in gastrointestinal physiology between humans and pigs (Henze, L. J. et al. J Pharm Pharmacol (2018)) and the large degree of genetic homology between their drug transporters. A high similarity in the transporter expression levels between porcine and human small intestine tissue was confirmed through reverse transcription polymerase chain reaction (RT-PCR) and western-blotting (FIGS. 2B-2C), except for ABCC3 and OSTα/β for which lack of available antibodies prohibited further analysis. Additionally, other researchers have shown that first-pass metabolic enzymes are similarly expressed in humans and pigs, (Van Peer, E., et al. Basic Clin Pharacol Toicol, vol 114: 387-394 (2014); Tang, H. et al. J Biochem Mol Toxicol, vol 18: 18-22 (2004); Mouly, S. & Paine, M. F., Pharm Res, vol 20: 1595-1599 (2003)) which has established native porcine intestinal tissue as a workhorse in oral drug delivery research (Westerhout, J. et al. Eur J Pharm Sci, vol 63: 167-177 (2014); Tang, H. & Mayersohn, M., Drug Metab Dispos, vol 46 1712-1724 (2018)).

Figure 3A:
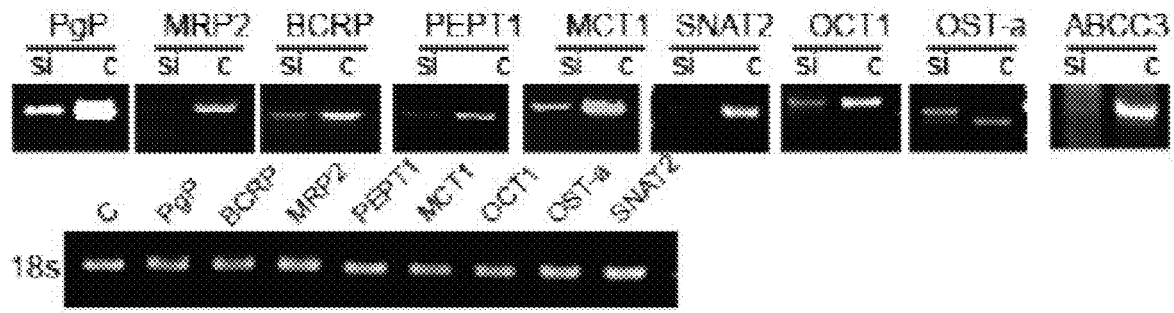
FIGS. 3A-3B show knock-down of expression of various drug transporters within an intestinal tissue explant 24 hours after siRNA delivery as measured by RT-PCR (FIG. 3A) and western-blot (FIG. 3B).
Figure 3B:
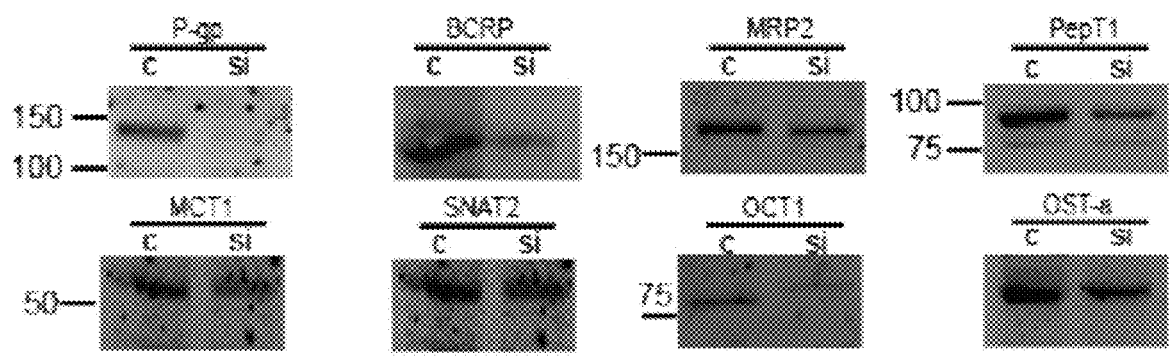
Figures 4A, 4B, 4C:
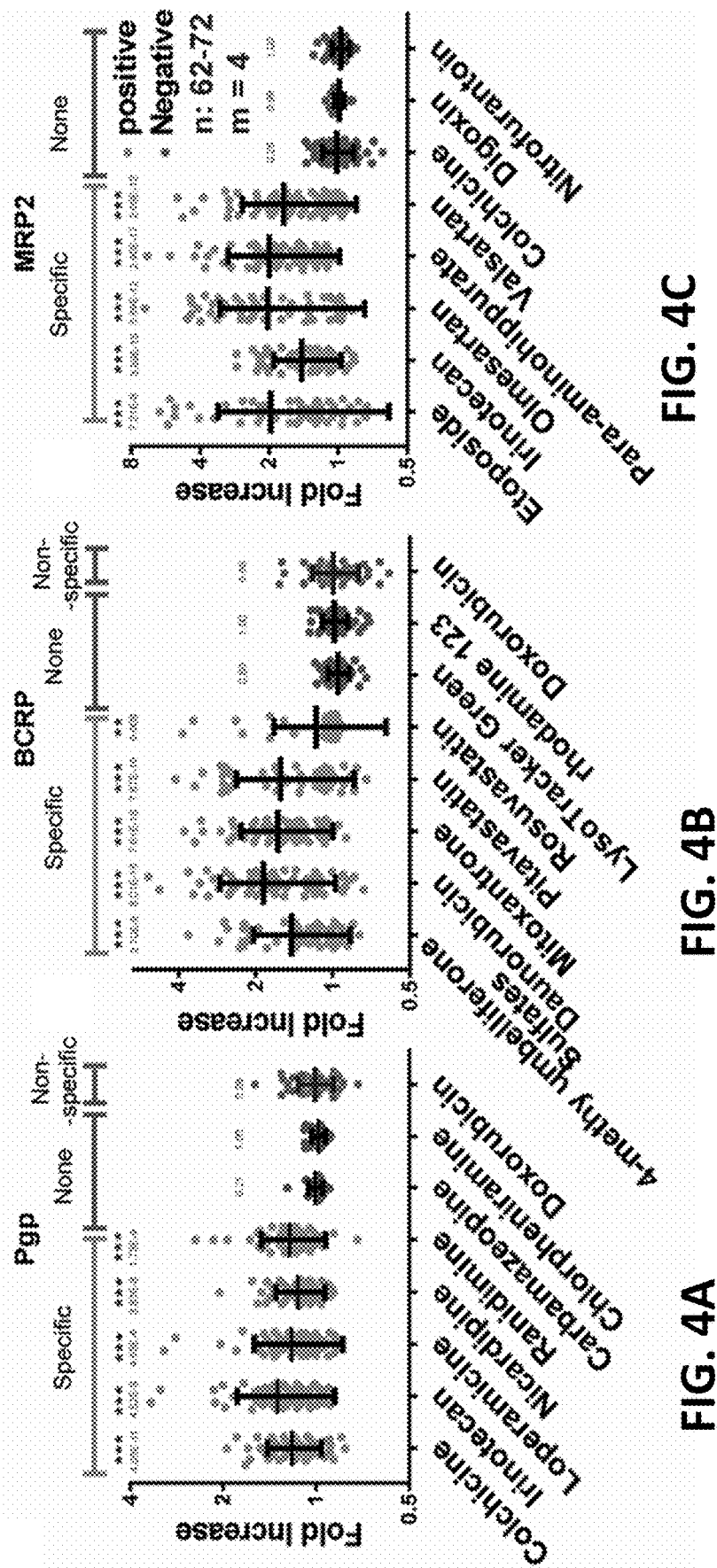
FIGS. 4A-4C provide graphs showing perfusion of indicated drugs in intestinal tissue explants after delivery is siRNA targeting p-glycoprotein (FIG. 4A), BCRP (FIG. 4B) or MRP2 (FIG. 4C). Drugs were either specific for the knocked-down drug transporter, non-specific, or did not have transporter (i.e., passively transported). The fold increase of drug absorption was measured by either fluorescent reading or UV-vis absorption. For each drug, the data was collected from 62-72 trials (n=62-72) of tissue in four different pigs (m=4). P values were determined by one-tailed z-test. Lines indicate mean value and error bars correspond to one standard deviation.

To establish a drug transporter model using porcine small intestine tissue, an siRNA knockdown protocol for each transporter in the ex vivo culture system was developed. siRNA was designed to target all major intestinal transporters and validated their knockdown capacity and specificity in the porcine PK15 cell line and in the ex vivo organ culture system using ultrasound-mediated delivery (data not shown). This workflow enabled specific targeting of each drug transporter in the pig small intestine with a knockdown efficiency of 2 to 10-fold while not impacting the expression of other transporters as validated through quantitative PCR (Q-PCR) and western-blotting (FIGS. 3A-3B).

Since the ex vivo system retained the intestinal submucosa, basal transporters could not be studied directly; therefore, further investigation on the luminal drug transporters P-gp, BCRP, MRP2, PEPT1, and MCT1 was carried out. If a molecule is transported by a specific transporter, its diffusion across the tissue should be impacted by selectively down regulating that transporter. To validate that the platform accurately captures this behavior, a total of 23 known transporter-drug relationships was tested. All investigated drugs exhibited a significant increase in perfusion when their respective transporter was knocked down (FIGS. 4A-4C and 6A-6B; $p<0.05$, one-tailed Z-test; $p<0.01$, two-tailed T test with the exception of Rosuvastatin $p=2\%$). As a control experiment, the change in perfusion for 11 drugs that are known to not be transported by these transporters was measured and found that none of their perfusions was significantly affected (FIGS. 4A-4C and 6A-6B; $p>0.05$, one-tailed Z-test) as expected.

Figure 5A:
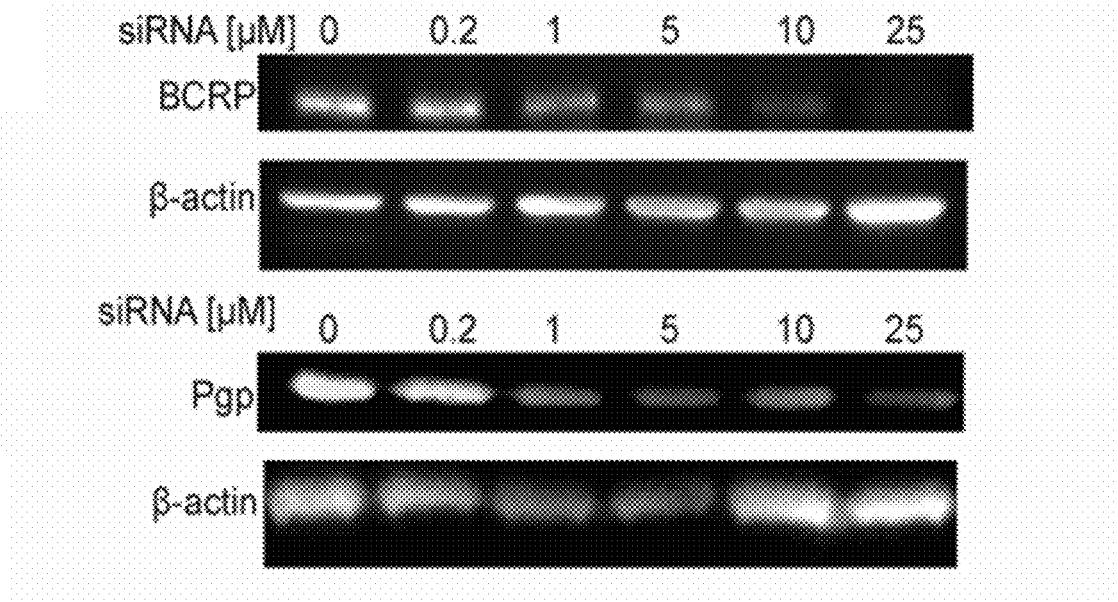
FIGS. 5A-5B show the level of reduction in P-gp and BCRP drug transporter expression depends on the dose of siRNA (0 to 25 µM) administered to the intestinal tissue explant.
Figure 5B:
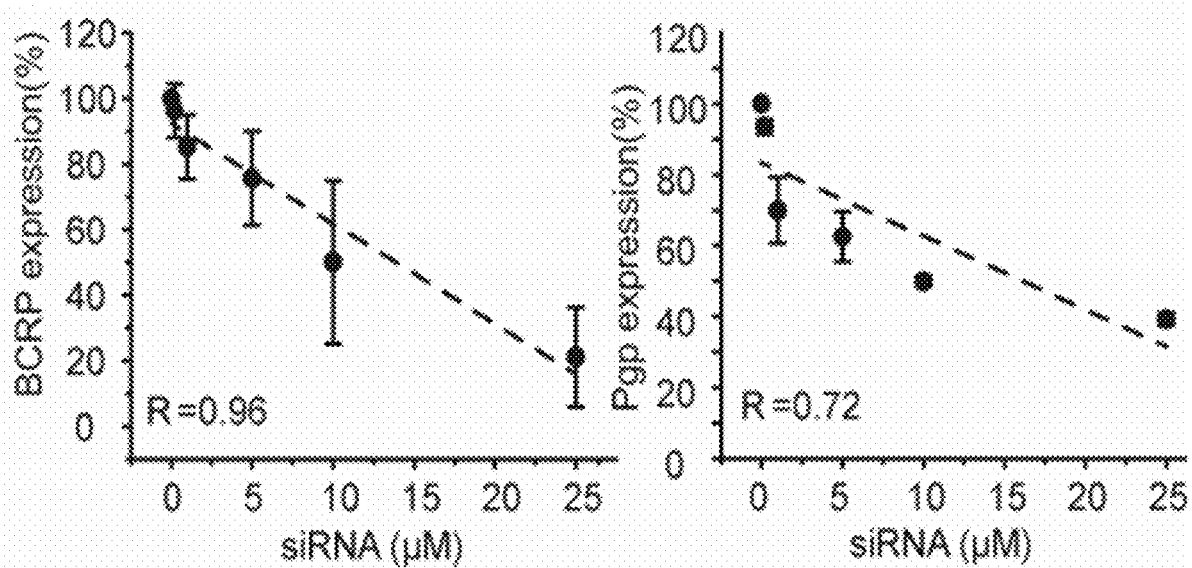
Figure 5C:
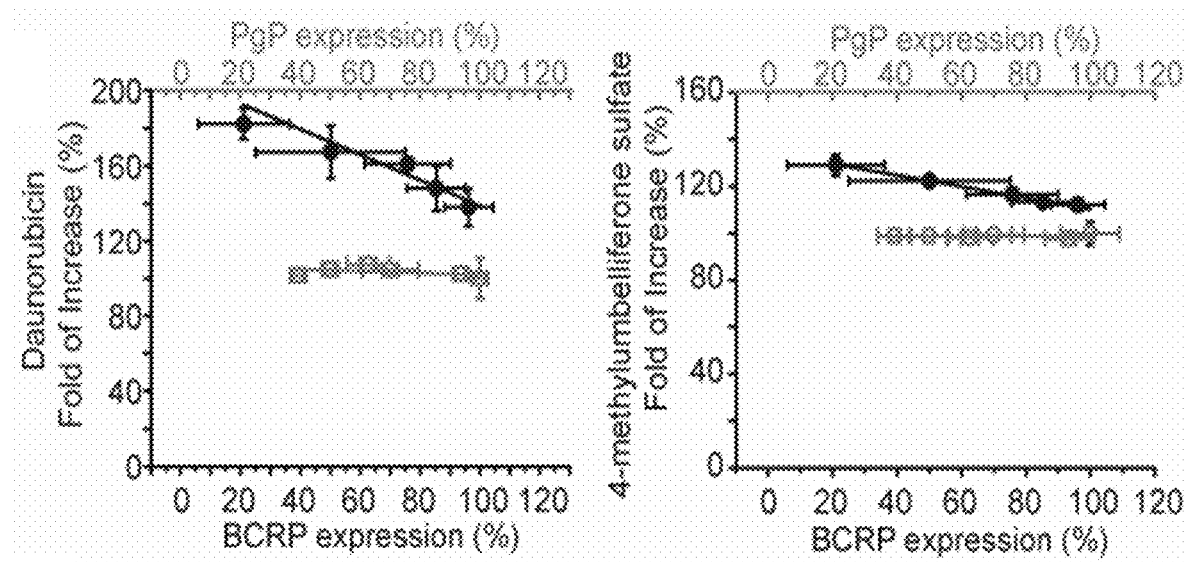
FIG. 5C is a graph showing the relationship between fold increase in perfusion for BCRP-specific substrates daunorubicin and 4-methylumbebeliferone sulfate and the level of BCRP expression.
Figure 5D:
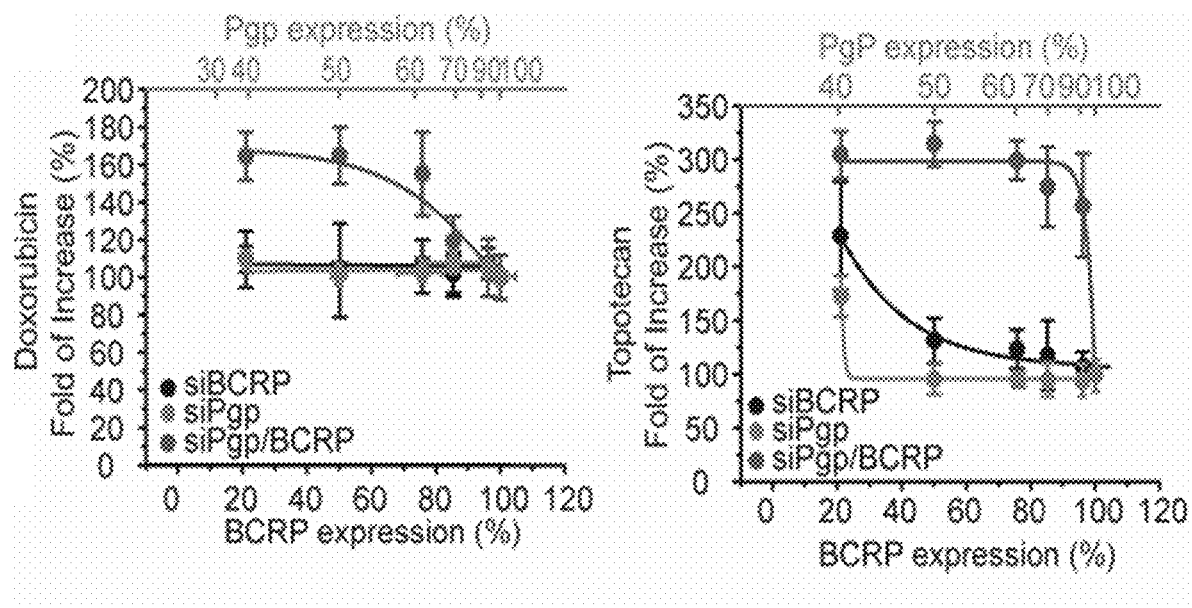
FIG. 5D is a graph showing the relationship between fold of increase in perfusion of substrates (doxorubicin and topotecan) that are transported by two efflux transporters (P-gp and BCRP) and the expression level of each individual drug transporter when dosed with single siRNA. The top line (medium gray) line indicates the relationship between fold increase of doxorubicin and topotecan to the expression level of Pgp and BCRP when co-dosing siPgp and siBCRP with different concentrations.
Figures 6A, 6B:
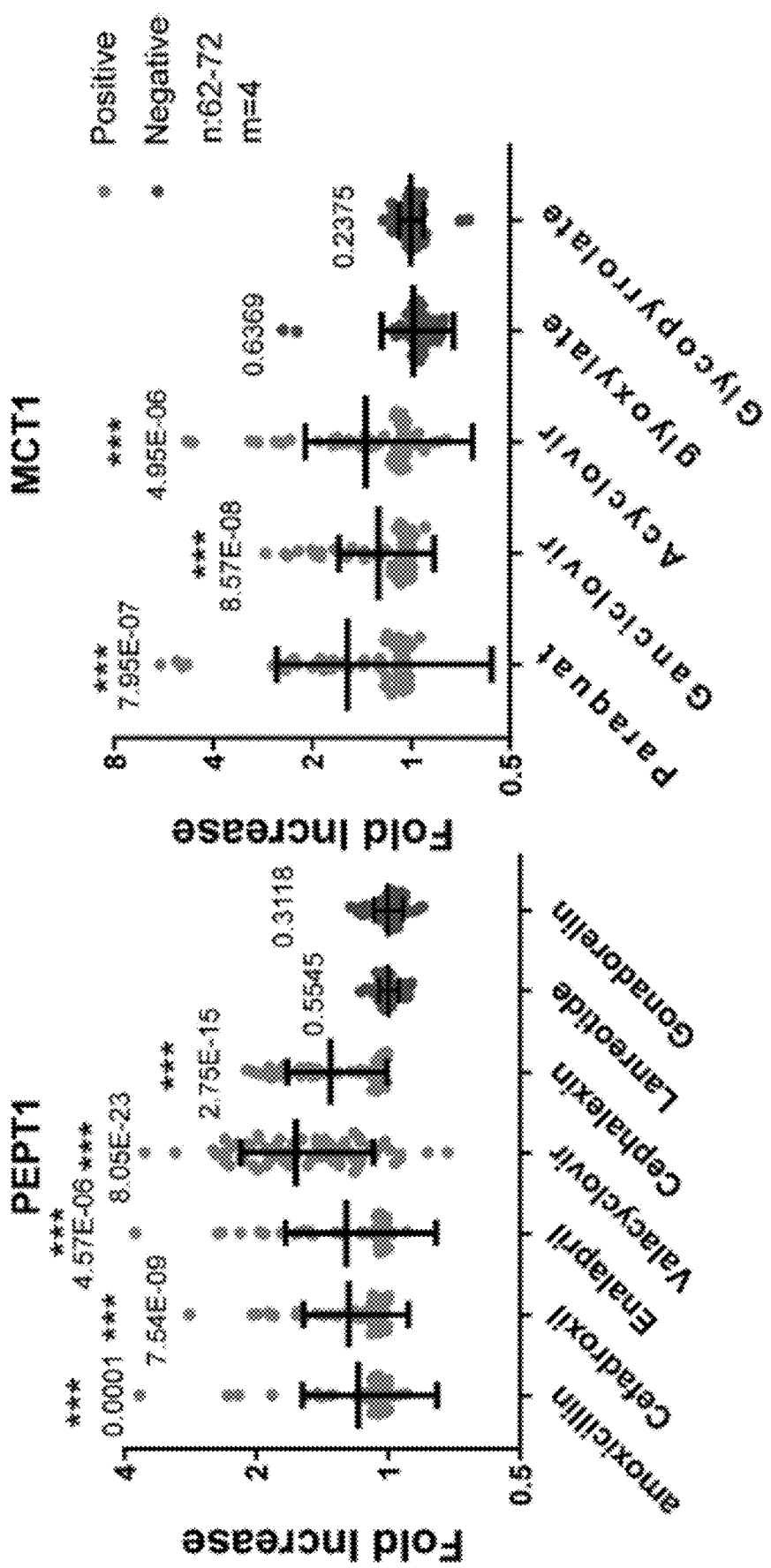
FIGS. 6A-6B provide graphs showing perfusion of substrates and non-substrates of PEPT1 (FIG. 6A) and MCT1 (FIG. 6B) drug transporters after knocking-down of the drug transporters.

Next perfusion of drugs that are known to be substrates for multiple transporters was studied. Down regulating a single transporter did not impact drug perfusion in this case (FIGS. 5A-5D), hinting at potentially synergistic and compensatory effects in the transportome network. To be able to delineate such effects, it was aimed to down regulate multiple transporters simultaneously. Two siRNAs targeting P-gp and BCRP were co-delivered with varying concentrations of each siRNA and noted that expression levels could be fine-tuned in a dose-dependent, linear fashion (Pearson $r=0.79$ and $0.96$, FIG. 5C). Next, how the simultaneous and gradual down regulation of transporter expression impacts drug perfusion was studied. Perfusion of BCRP-specific substrates increased linearly with reduced BCRP-expression (dauricine $R=0.7$, hymecromone sulfate $R=0.81$) but were not affected by altering P-gp expression ($p>0.28$ one-tailed Z test at maximum siPgp concentration; FIG. 5C). For substrates of both transporters, down regulation of either individual transporter did not impact perfusion or only marginally at maximal siRNA concentration (FIG. 5D). Even slight down regulation of both transporters strongly increased drug perfusion up to 160% or 300% (FIG. 5D). This data highlights the ability of this platform to capture the dynamic interplay and synergistic effects of multiple transporters that can compensate the loss of one of the two transporters.

Figure 7:
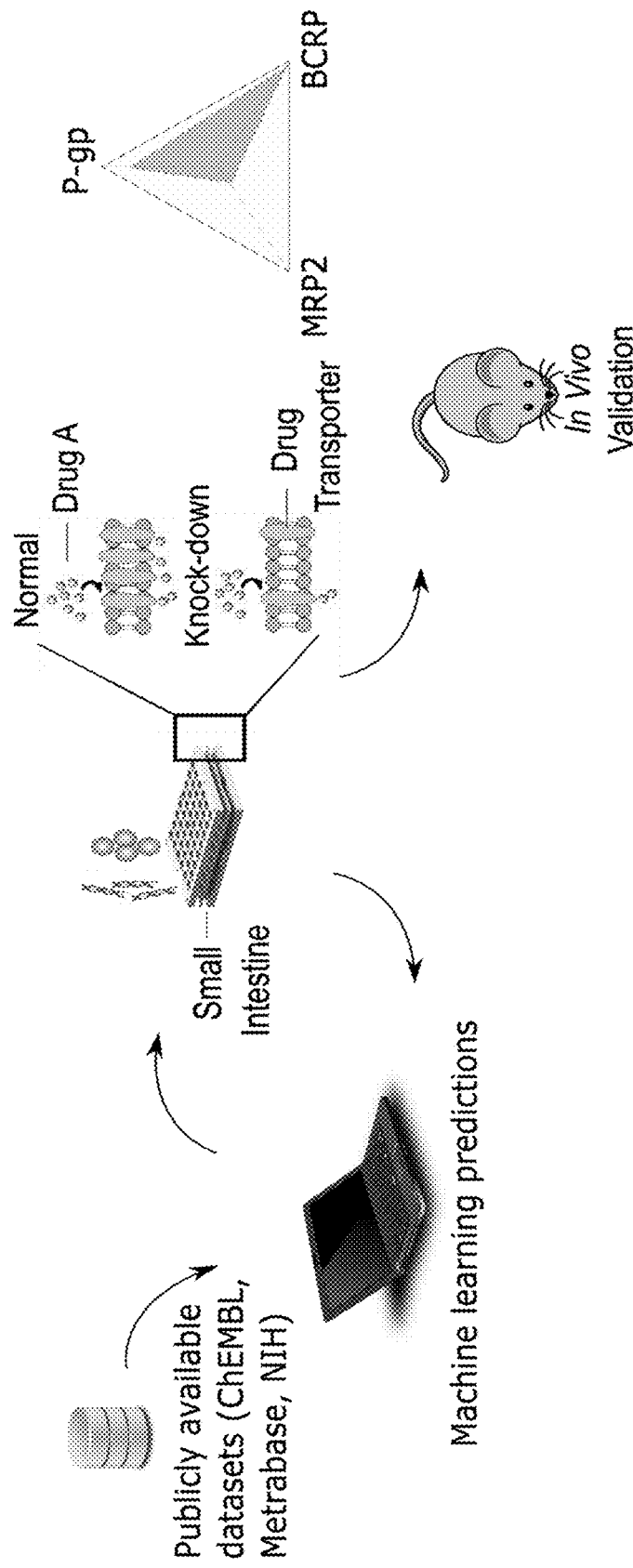
FIG. 7 is a schematic showing the process of generating a database of drug transport interactions with small molecule drugs an screening compounds using three individual data sources (DrugBank, Metrabase, NCI-60) and machine learning-guided literature research to build a random forest machine learning model. The physical and chemical properties of a new potential drug are then incorporated into a random forest-based machine learning algorithm to generate predictions of the potential substrate relationship with various drug transporters. Based on the prediction report, a series of siRNA induced drug transporter knock-downs are performed on an ex vivo porcine small intestine tissue screening platform. This ex vivo data was fed back into the machine learning algorithm to further modify the database and improve the predictive performance. Identified substrate relationships were subsequently validated in vivo.

Example 3: Development of a Machine Learning Platform for Rapid Prediction of Transporter-Substrate Profiles While the above data indicated the ability to knock down a set of transporters to study the transporter profile of clinically relevant drug molecules, the combinatorial explosion of necessary experiments prohibits exhaustive profiling. For example, investigating the full transportome profile for a single drug by creating all possible knockdown combinations of the 149 known drug transporters would require more than seven hundred tredecillion ($7 \times 10^{44}$) experiments. It was hypothesized that machine learning can be used to streamline experiments and focus knockdown experiments only on the most likely transporter-substrate relationships. Machine learning efforts were concentrated on the three efflux transporters P-gp, BCRP, and MRP2 given their significance for clinical drug transport as supported by having the greatest number of annotated substrates. A training dataset mined from DrugBank (Wishart, D. S. et al., Nucleic Acids Res, vol 46: D1074-D1082 (2018)), Metrabase (Mak, L. et al., J Cheminform, vol 7: 31 (2015)), and the NIH screen NCI-60 (Szakacs, G. et al. Cancer Cell, vol 6: 129-137 (2004); Wallqvist, A., et al. Bioinformatics, vol 19: 2212-2224 (2003)) was manually curated. See FIG. 7 for an exemplary workflow. A random forest machine learning model accurately predicts the substrate relationships in this dataset based on chemical and physicochemical features of the substrates and non-substrates, with 81% correct predictions in ten-fold cross validations. It was confirmed that the random forest architecture outperforms six alternative, state-of-the-art machine learning models (Table 6). It was also refuted that the high performance is exclusively driven by analog identification by showing that the model retained high accuracy of 75% in cluster-based cross validations (Table 7).

TABLE 6

Performance of different machine learning models to predict transporter-drug relationships

| | Model | | | | | |
|---|---|---|---|---|---|---|
| | MDR1 | | BCRP | | MRP2 | |
| | Mean MCC | p value | Mean MCC | p value | Mean MCC | p value |
| Random Forest | 0.56 | — | 0.49 | — | 0.51 | — |
| Naïve Bayes | 0.0 | 1e-31 | -0.01 | 3e-24 | -0.01 | 2e-19 |
| kNN | 0.15 | 1e-24 | 0.04 | 6e-24 | 0.05 | 5e-24 |
| Decision Tree | 0.35 | 3e-16 | 0.29 | 6e-16 | 0.31 | 2e-13 |
| MLP | -0.16 | 4e-25 | -0.00 | 1e-18 | 0.02 | 3e-21 |
| LinearSVC | 0.1 | 3e-22 | 0.05 | 2e-23 | 0.04 | 1e-23 |
| ExtraTrees | 0.5 | 2e-10 | 0.41 | 4e-11 | 0.45 | 3e-09 |
| Gaussian Process | 0.16 | 6e-26 | 0.08 | 3e-24 | 0.02 | 3e-26 |

TABLE 7

Leave-one-cluster-out validation for random forest machine learning model

| | MDR1 | BCRP | MRP2 |
|---|---|---|---|
| Accuracy | 0.72 | 0.75 | 0.79 |
| MCC | 0.36 | 0.30 | 0.33 |

To assess the performance of our model on external data, unknown transport-substrate relationships for the training molecules was predicted, thereby completing the transporter profiles for compounds that are only partially annotated in the data. Then the literature was manually screened to validate or refute these predictions. Overall, 70% of these predictions were validated to be correct, where 58% were correct drug-substrate interactions while 42% were correct predictions of non-substrates—highlighting the capability of the model to correctly identify both substrates and non-substrates. It was noted that accuracy correlated with predictive confidence, with 80% of the high confidence predictions being correct while only 50% of low confidence predictions were correct. Accordingly, it was decided to specifically focus the data completion campaign on these low confidence predictions, since these would be most relevant to augment the predictive scope of our model. Through this, an augmented dataset of 4554 transporter-drug relationships was generated that we used to train a refined random forest model to predict unknown transporter profiles.

Example 4: Machine Learning and Tissue Engineering Streamline Substrate Relationships for Approved Drugs and Investigational Compounds It was first aimed to assess whether the workflow could generate useful insights for approved drugs. To this end, the machine learning model described above was applied to a panel of 28 model drugs that form a representative set of molecular structures with a wide range of intestinal perfusion abilities. Transporter interactions with P-gp, BCRP, and MRP2 was exhaustively screened through knockdown experiments. Overall, it was found that machine learning and the experimental results agreed in 76.2% of the experiments, indicating that the rapid in silico predictions enable experimental streamlining. Since these approved drugs are established medications that have undergone ample preclinical and clinical investigation, it was noted that half (57.1%) of their transporter interactions can be found in the literature. This attests to the ability of the workflow to identify relationships that can also be identified via classical experimental and clinical workflows. Notwithstanding these significant previous efforts, the focused screen of 28 model drugs discovered 13 currently unknown transporter-drug interactions that had not been reported previously (Table 8), suggesting that the platform can generate new transporter knowledge even for highly scrutinized molecules. Importantly, these findings could have immediate implications for patients receiving these medications.

TABLE 8

Summary of mock screening result compared with previous literature reports

| Drug Name | CAS ID | Literature Target | Platform Target | Pubmed ID |
|---|---|---|---|---|
| ±)-Verapamil hydrochloride | 152-11-4 | Pgp | Pgp | 62969 |
| Ibuprofen | 15687-27-1 | Pgp | Pgp | 3672 |
| Curcumin | 458-37-7 | BCRP | BCRP | 969516 |
| Atorvastatin calcium salt trihydrate | 344423-98-9 | Pgp & MRP2 | Pgp & MRP2 | 71311905 |
| Warfarin | 81-81-2 | Pgp & BCRP | Pgp & BCRP | 54678486 |
| Quinine | 130-95-0 | Pgp & BCRP | Pgp & BCRP | 3034034 |
| Coumarin | 91-64-5 | Pgp | Pgp | 323 |
| Acyclovir | 59277-89-3 | no target | no target | 135398513 |
| Furosemide | 54-31-9 | MRP2 | MRP2 | 3440 |
| Chlorotetracycline | 57-62-5 | no target | no target | 54675777 |
| Ergotamine D-tartrate | 379-79-3 | Pgp | Pgp & BCRP & MRP2 | 9787 |
| Labetalol hydrochloride | 32780-64-6 | no target | no target | 71412 |
| Danazol | 17230-88-5 | no target | no target | 28417 |
| Ketoprofen | 22071-15-4 | no target | no target | 3825 |
| Piroxicam | 36322-90-4 | no target | no target | 54676228 |
| Ranitidine | 66357-35-5 | Pgp & BCRP | Pgp & BCRP & MRP2 | 3001055 |
| Carbamazepine | 298-46-4 | Pgp | Pgp & BCRP | 2554 |
| Terbutaline | 23031-25-6 | no target | no target | 5403 |
| L-phenylalanine | 63-91-2 | no target | no target | 6140 |
| Naproxen | 22204-53-1 | no target | no target | 156391 |
| Loperamide | 53179-11-6 | no target | no target | 3955 |
| Dihydroergotamine (+)-tartrate salt | 5989-77-5 | Pgp | MRP2 | 71171 |
| Candesartan cilexetil | 139481-59-7 | Pgp | no target | 2540 |
| S)-(−)-Propranolol hydrochloride | 4199-10-4 | Pgp | Pgp | 165193 |
| Pamidronate disodium salt hydrate | 57248-88-1 | no target | Pgp | 16078998 |
| Doxycycline | 564-25-0 | no target | BCRP & MRP2 | 54671203 |
| Nadolol | 42200-33-9 | no target | BCRP | 39147 |

Figure 8A:
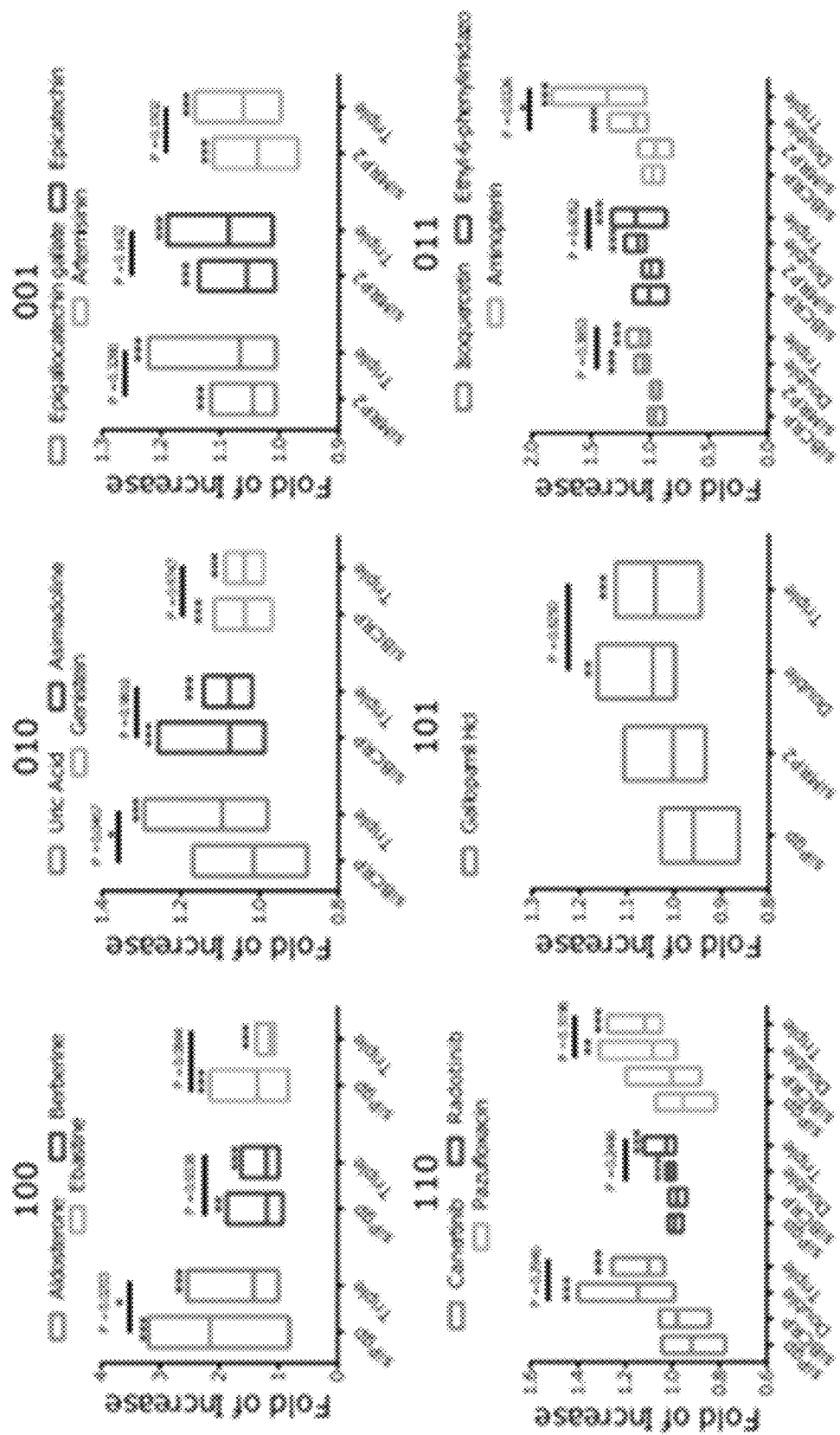
FIGS. 8A-8B provides graphs showing fold increase in perfusion of top drug hits that were predicted to interact with (i) only one drug transporter when dosing predicted single siRNA, or triple siRNAs (FIG. 8A top); (ii) two drug transporters when dosing single siRNA, two siRNA combined and triple siRNAs (FIG. 8A bottom); or (iii) all three or none of the drug transporters when dosing single siRNA and combined triple siRNAs (FIG. 8B). For all plots the data was collected from 12 trials (n=12) of tissue extracted from three different pigs (n=3). P values for each condition were determined by one-tailed z-test. P values for comparison between groups was determined by student t-test with multiple test correction. Lines indicate mean value and error bars correspond to one standard deviation.
Figure 8B:
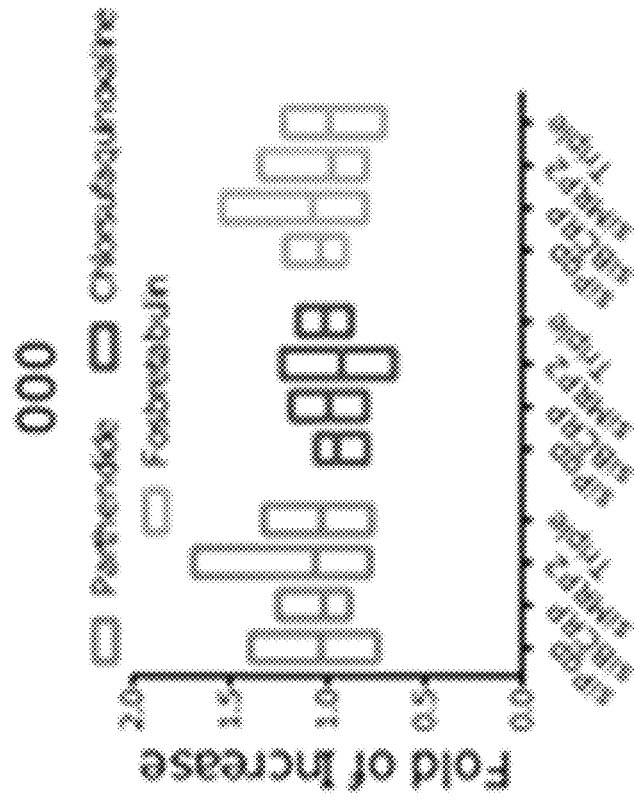
Figure 8B:
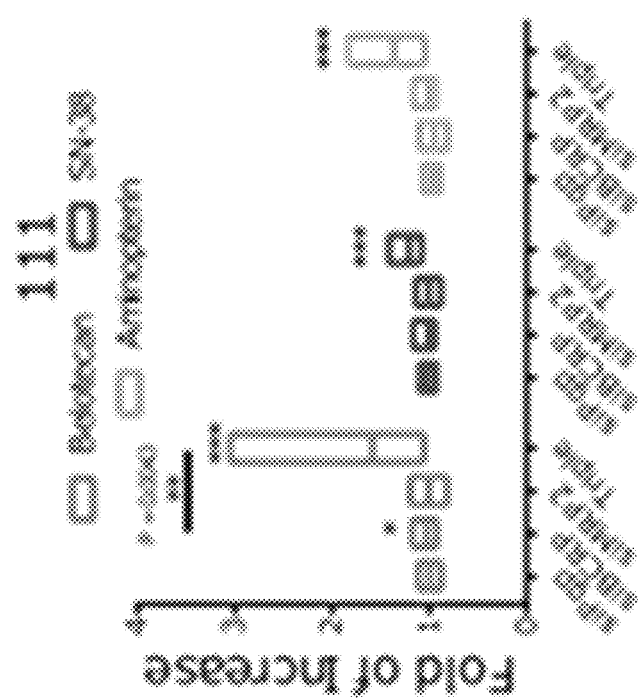

Given these promising results for established medications, it was explored whether the platform could also discover transporter profiles for investigational drugs. To this end, the platform predicted the transporter profile of 1595 investigational, small molecular drugs (DrugBank 5.0). Using these predictions, all investigational drugs were classified into 9 categories: selective substrates for either P-gp, BCRP, or MRP2; dual substrates for either P-gp/BCRP, P-gp/MRP2, or BCRP/MRP2; "super substrates" for all three drug transporters; and "super drugs" with no predicted interaction and therefore no transport liability. The top three hits were selected from each of these nine categories (with the exception of the P-gp/MRP2 dual substrate gallopamil, given the commercial unavailability of the other top candidates), resulting in a validation set of 25 compounds that were tested experimentally for their predicted transporter interactions. To fully characterize the potential transporter-transporter interactions, the next step was to investigate their perfusion after individual knockdowns as well as possible combinations of anticipated transporters. Results are shown in FIGS. 8A-8B. 91% of the predictions were validated ex vivo, covering all possible classes of transporter profiles. This confirmed the applicability of the workflow to preclinical drug development and also further attests to the ability of the platform to identify distinct types of transporter profiles.

Example 5: In Vivo Validation of Novel Transport Associations

Figure 9:
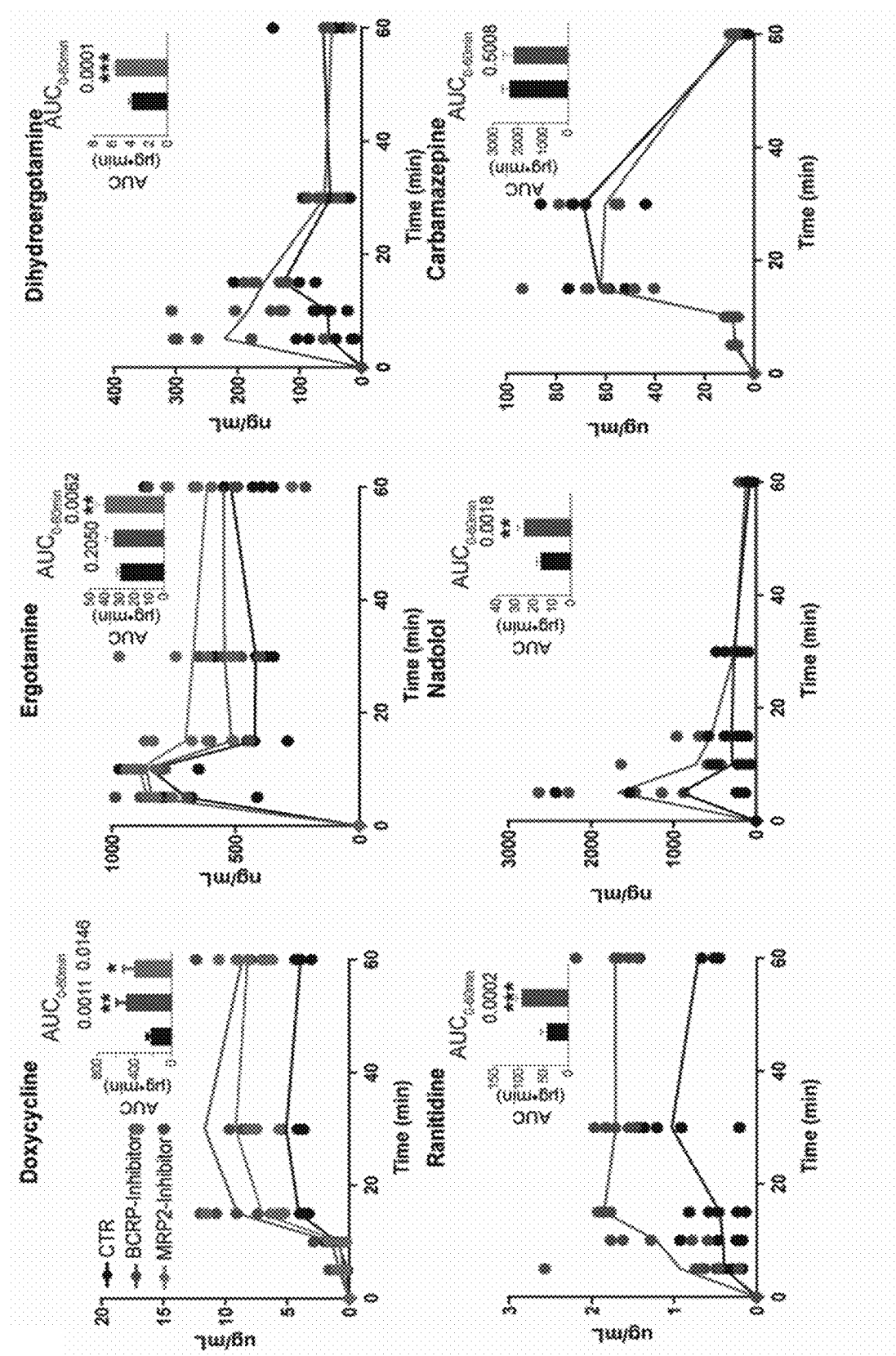
FIG. 9 provides graphs showing in vivo pharmacokinetics of potential substrates identified from FIG. 8 on B al b/c mice. Drug transporter inhibitor (Verapamil for Pgp, Imatinib for MRP2 and Probenecid for BCRP) was administered 15 minutes prior to drug via oral gavage, while for the control group, PBS was administered instead. The serum drug level was determined through LC-MS/MS, HPLC, and/or GC/MS. n=5 for each time point. Inserts show AUC comparison within 60 minutes time window after drug oral administration for potential substrate. p-value was calculated based on One-way ANOVA analysis. *p<0.05, p<0.01, *p<0.001.

To validate the physiological relevance of the newly identified substrate relationships, an in vivo pharmacokinetic study was performed in Balb/c mice. Candidate drugs were delivered by oral gavage and the resulting drug concentration in blood serum was determined for the following 60 minutes—fully capturing the absorption phase of the pharmacokinetic curve. The area under the concentration-time curve (AUC) when administering the candidate drugs was compared to naïve mice compared to mice where the function of specific drug transporters were reduced by pre-treating the mouse through oral administration of known transport inhibitors (verapamil for P-gp, imatinib for BCRP, or probenecid for MRP2). Analysis of relative AUC revealed a significant increase in drug absorption for seven out of the eight tested candidate drugs (p<0.05, two-tail student T-test, FIG. 9). Only carbamazepine did not show the expected effect, which might be explained by increased glucoronidation of carbamazepine induced by our transport inhibitor probenecid. These results support the significant predictive capacity of the approach described herein, the transferability of acquired results into complex in vivo conditions and showcase the ability to generate actionable knowledge of drug transport liabilities for approved drugs. For example, doxycycline is a known substrate of P-gp and OAT1, but the newly discovered interactions with BCRP and MRP2 doubles the number of known transporters for this drug.

Example 6: Identifying Transporter Induced Drug-Drug Interactions

Finally, it was hypothesized that newly identified transporter substrate profiles might not only be relevant to understand and improve drug absorption, but could also be the cause for clinically relevant drug-drug interactions when two medications compete for the same transporter. To gauge the potential magnitude of this challenge, the P-gp, BCRP, and MRP2 substrate profiles for all small molecules found in DrugBank 5.0 was predicted. Potential drug-drug interactions were then defined as pairs of drugs that share at least one known or predicted transporter, given that an overlapping substrate or inhibitor relationship might alter transport kinetics for both substrates. By this definition, newly predicted transporter-drug relationships could cause up to 1,810,270 potential novel drug-drug interactions that were not known based on previously known transporter-drug relationships.

While these numbers are staggering, it is unknown whether these calculated substrate profiles are indeed predictive of altered uptake during co-administration of the identified pairs of drugs. Accordingly, the next goal was to validate some of the predicted interactions experimentally. Doxycycline was chosen as the primary test compound given its broad clinical use and that it was identified here and in vivo validated it as a novel BCRP and MRP2 substrate. Four candidate drugs that are known substrates of BCRP and MRP2 were manually selected to study whether they could potentially interact with doxycycline. Warfarin, tacrolimus, digoxin, and levetiracetam were chosen as candidates for the following reasons: (i) close monitoring of warfarin through PT-INR levels and tacrolimus, digoxin, and levetiracetam levels in the clinic enables the direct identification of potential interactions from clinical data, (ii) they have narrow therapeutic windows which makes the identification of potential interacting drugs critical, (iii) a significant patient population receives these combinations to treat their co-morbidities, and (iv) while for tacrolimus there have been previous suggestions of potential interactions without a clearly identified mechanism (Gupta, A. et al. Cancer Chemother Pharmacol, vol. 58: 374-383 (2006)), the other three (warfarin, digoxin, levetiracetam) represent unknown interactions.

Figure 10:
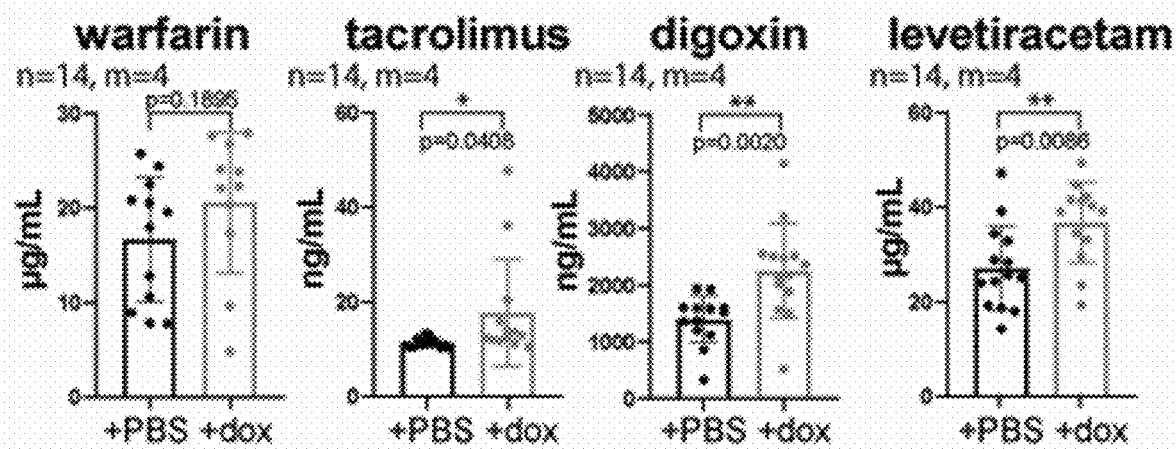
FIG. 10 provides graphs showing ex vivo validation (top) and clinical data analysis (bottom) of doxycycline interactions with warfarin, tacrolimus, digoxin and levetiracetam. Boxes indicate mean value and error bars correspond to one standard deviation.
Figure 10:
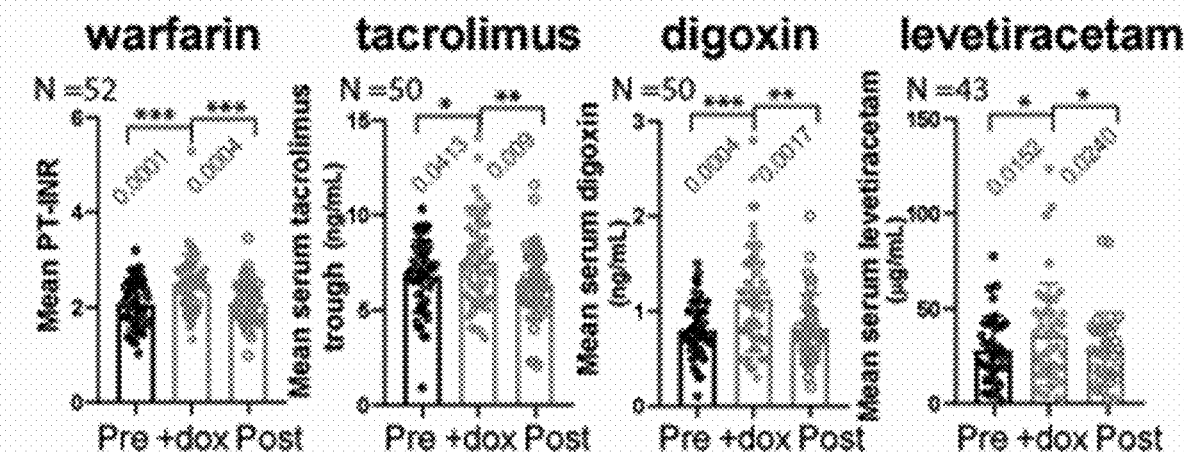

As a first-line test (FIG. 10), ex vivo perfusion experiments were conducted to test for changes in absorption when co-administering the candidates with doxycycline. Table 9 shows the preparation and detection method for the drugs tested. All drugs except warfarin showed a significant increase in perfusion upon co-treatment with doxycycline ($p<0.05$). To assess the clinical relevance of these findings, patients (n=43-50) were identified from the Partners Research Patient Data Registry for which data on their drug levels before, during, and after doxycycline exposure were acquired. A significant increase of all four tested drugs when co-administrated with doxycycline ($p<0.05$) was found, while levels returned back to baseline after completion of doxycycline therapy ($p<0.05$). While warfarin and tacrolimus are also metabolized through cytochrome P450 3A4, which might at least in part explain this interaction, digoxin and levetiracetam are not cytochrome substrates and therefore provide good evidence for transporter-driven interactions. Importantly, with the exception of a moderate clinical warning for doxycycline-warfarin, none of the other combinations are currently recognized as known drug-drug interactions. Therefore, these cases highlight the potential of the platform to identify clinically-relevant and previously unknown drug-drug interactions with immediate implications for clinical practice.

TABLE 9

Name, preparation and detection method of drug-drug interactions validated ex vivo

| Drug Name | CAS ID | Concentration mg/mL | Solute | Detection Method |
|---|---|---|---|---|
| Warfarin | 81-81-2 | 1 | PBS | LC-MS/MS |
| Tacrolimus | 104987-11-3 | 1 | 3% DMSO + 15% PEG300 | LC-MS/MS |
| Digoxin | 20830-75-5 | 1 | 5% DMSO + 20% PEG300 | LC-MS/MS |
| Levetiracetam | 102767-28-2 | 1 | PBS | LC-MS/MS |
| Doxycycline | 564-25-0 | 1 | PBS | LC-MS/MS |

What is claimed:

1. An ex vivo system for use in determining multiplex interactions between a candidate drug and two or more drug transporters in an intestinal tissue explant, the system comprising:
   (i) an intestinal tissue explant in planar contact with a substrate, wherein the intestinal tissue explant comprises intestinal epithelium from a large, non-human, mammalian gastrointestinal tract, wherein the intestinal epithelium comprises epithelial cells having a polarity in the tissue explant and two or more drug transporters, and wherein the tissue explant provides a luminal surface and a basolateral surface; and
   (ii) two or more agents for use in reducing or eliminating expression of the two or more drug transporters in the intestinal tissue explant, wherein the two or more drug transporters are on the luminal surface of the tissue explant and selected from: p-glycoprotein (p-gp), breast cancer resistance protein (BCRP), multidrug resistance 2 (MRP2), monocarboxylate transporter 1 (MCT1), and peptide transporter 1 (PEPT1), wherein the two or more agents are two or more siRNA molecules selected from the group consisting of:
      (1) a p-gp targeting siRNA molecule comprising a sense strand comprising the nucleotide sequence set forth in SEQ ID NO: 91 and an antisense strand comprising the nucleotide sequence set forth in SEQ ID NO: 92;
      (2) a MRP2 targeting siRNA molecule comprising a sense strand comprising the nucleotide sequence set forth in SEQ ID NO: 93 and an antisense strand comprising the nucleotide sequence set forth in SEQ ID NO: 94;
      (3) a BCRP targeting siRNA molecule comprising a sense strand comprising the nucleotide sequence set forth in SEQ ID NO: 95 and an antisense strand comprising the nucleotide sequence set forth in SEQ ID NO: 96;
      (4) a PEPT1 targeting siRNA molecule comprising a sense strand comprising the nucleotide sequence set forth in SEQ ID NO: 99 and an antisense strand comprising the nucleotide sequence set forth in SEQ ID NO: 100; and
      (5) a MCT1 targeting siRNA molecule comprising a sense strand comprising the nucleotide sequence set forth in SEQ ID NO: 101 and an antisense strand comprising the nucleotide sequence set forth in SEQ ID NO: 102,
   wherein the system provides for multiplex interactions between the candidate drug and the two or more drug transporters to be determined by contacting the intestinal tissue explant with the candidate drug before and after expression of the two or more drug transporters is reduced or eliminated in the intestinal tissue explant.

2. The ex vivo system of claim 1, wherein the two or more drug transporters comprise (i) p-gp and BCRP; (ii) p-gp and MRP2; (iii) BCRP and MRP2; or (iv) p-gp, BCRP and MRP2.

3. The ex vivo system of claim 1, wherein the substrate comprises a plurality of microwells.

4. The ex vivo system of claim 1, wherein the substrate comprises a first plate comprising the plurality of microwells and a second plate, wherein the tissue explant is between the first and second plates.

5. The ex vivo system of claim 4, wherein the second plate comprises a plurality of microwells.

6. The ex vivo system of claim 5, wherein the plurality of microwells of the first plate are through holes, and wherein the plurality of microwells of the second plate are receiving chambers.

7. A kit comprising an ex vivo system for use in determining multiplex interactions between a candidate drug and two or more drug transporters in an intestinal tissue explant, the kit comprising:
   (i) an intestinal tissue explant comprising intestinal epithelium from a large, non-human, mammalian gastrointestinal tract, wherein the intestinal epithelium comprises epithelial cells having a polarity in the tissue explant and two or more intact drug transporters, wherein the tissue explant provides a luminal surface and a basolateral surface, and wherein the polarity of the epithelial cells is maintained in the tissue explant;
   (ii) two or more agents for use in reducing or eliminating expression of at least two drug transporters selected from: p-gp, BCRP, MRP2, MCT1, and PEPT1, wherein the two or more agents are two or more siRNA molecules selected from the group consisting of:
      (1) a p-gp targeting siRNA molecule comprising a sense strand comprising the nucleotide sequence set forth in SEQ ID NO: 91 and an antisense strand comprising the nucleotide sequence set forth in SEQ ID NO: 92;
      (2) a MRP2 targeting siRNA molecule comprising a sense strand comprising the nucleotide sequence set forth in SEQ ID NO: 93 and an antisense strand comprising the nucleotide sequence set forth in SEQ ID NO: 94;
      (3) a BCRP targeting siRNA molecule comprising a sense strand comprising the nucleotide sequence set forth in SEQ ID NO: 95 and an antisense strand comprising the nucleotide sequence set forth in SEQ ID NO: 96;
      (4) a PEPT1 targeting siRNA molecule comprising a sense strand comprising the nucleotide sequence set forth in SEQ ID NO: 99 and an antisense strand comprising the nucleotide sequence set forth in SEQ ID NO: 100; and
      (5) a MCT1 targeting siRNA molecule comprising a sense strand comprising the nucleotide sequence set forth in SEQ ID NO: 101 and an antisense strand comprising the nucleotide sequence set forth in SEQ ID NO: 102; and
   (iii) instructions for use of the system to determine multiplex interactions between the candidate drug and the two or more drug transporters, wherein the instructions comprise contacting the intestinal tissue explant with the candidate drug before and after expression of the two or more drug transporters is reduced or eliminated in the intestinal tissue explant.

8. A method for determining multiplex interactions between a candidate drug and two or more drug transporters, comprising:
   (i) contacting the tissue explant of claim 1 with the candidate drug;
   (ii) determining adsorption of the candidate drug by detecting the presence of the drug at the luminal surface and at the basolateral surface, wherein presence of the drug at the basolateral surface indicates ability of the drug to be absorbed through the tissue explant; and
   (iii) comparing absorption between the tissue explant before and after expression of the two or more drug transporters is reduced or eliminated in the intestinal tissue explant, thereby determining multiplex interactions between the candidate drugs and the two or more drug transporters.

9. A method for investigating known multiplex interactions between a candidate drug and two or more drug transporters, comprising:
  (i) contacting the tissue explant of claim 1 with the candidate drug;
  (ii) determining adsorption of the candidate drug by detecting the presence of the drug at the luminal surface and at the basolateral surface, wherein presence of the drug at the basolateral surface indicates ability of the drug to be absorbed through the tissue explant; and
  (iii) comparing absorption between the tissue explant before and after expression of the two or more drug transporters is reduced or eliminated in the intestinal tissue explant,
  thereby investigating the known multiplex interactions between the candidate drug and two or more drug transporters.

10. The method of claim 9, further comprising using a machine learning algorithm to determine the known multiplex interaction.

* * * * *